(12) United States Patent
Cain

(10) Patent No.: US 11,712,342 B2
(45) Date of Patent: *Aug. 1, 2023

(54) EXPANDABLE INTERVERTEBRAL IMPLANT

(71) Applicant: DePuy Synthes Products, Inc., Raynham, MA (US)

(72) Inventor: Christopher Marden John Cain, Denver, CO (US)

(73) Assignee: DePuy Synthes Products, Inc., Raynham, MA (US)

( * ) Notice: Subject to any disclaimer, the term of this patent is extended or adjusted under 35 U.S.C. 154(b) by 267 days.

This patent is subject to a terminal disclaimer.

(21) Appl. No.: 17/017,872

(22) Filed: Sep. 11, 2020

(65) Prior Publication Data

US 2020/0405500 A1 Dec. 31, 2020

Related U.S. Application Data

(63) Continuation of application No. 16/593,430, filed on Oct. 4, 2019, which is a continuation of application (Continued)

(51) Int. Cl.
*A61F 2/44* (2006.01)
*A61F 2/46* (2006.01)
(Continued)

(52) U.S. Cl.
CPC ............ *A61F 2/4425* (2013.01); *A61F 2/442* (2013.01); *A61F 2/447* (2013.01); *A61F 2/4611* (2013.01);
(Continued)

(58) Field of Classification Search
CPC .. A61F 2/44; A61F 2/46; A61F 2/4425; A61F 2/442; A61F 2/447; A61F 2/4611
See application file for complete search history.

(56) References Cited

U.S. PATENT DOCUMENTS

| 1,802,560 A | 4/1931 | Kerwin |
| 1,924,695 A | 8/1933 | Olson |

(Continued)

FOREIGN PATENT DOCUMENTS

| AU | 2006279558 A1 | 2/2007 |
| AU | 2005314079 B2 | 7/2012 |

(Continued)

OTHER PUBLICATIONS

U.S. Appl. No. 09/558,057, filed Apr. 26, 2000, entitled Bone Fixation System.

(Continued)

*Primary Examiner* — Christopher J Beccia
(74) *Attorney, Agent, or Firm* — BakerHostetler

(57) ABSTRACT

An expandable intervertebral implant is provided for insertion into an intervertebral space defined by adjacent vertebrae. The expandable intervertebral implant includes a pair of outer sleeve portions and an inner core disposed between the outer sleeve portions. Movement of the inner core relative to the outer sleeve portions causes the outers sleeve portions to deflect away from each other, thereby engaging the expandable intervertebral implant with the vertebrae and adjusting the height of the intervertebral space.

17 Claims, 24 Drawing Sheets

Related U.S. Application Data

No. 15/926,247, filed on Mar. 20, 2018, now Pat. No. 10,449,056, which is a continuation of application No. 15/235,160, filed on Aug. 12, 2016, now Pat. No. 9,931,223, which is a continuation of application No. 14/565,611, filed on Dec. 10, 2014, now Pat. No. 9,414,934, which is a continuation of application No. 12/936,466, filed as application No. PCT/US2009/039501 on Apr. 3, 2009, now Pat. No. 8,936,641.

(60) Provisional application No. 61/042,724, filed on Apr. 5, 2008.

(51) Int. Cl.
*A61F 2/28* (2006.01)
*A61F 2/30* (2006.01)

(52) U.S. Cl.
CPC . *A61F 2002/2835* (2013.01); *A61F 2002/305* (2013.01); *A61F 2002/3052* (2013.01); *A61F 2002/3055* (2013.01); *A61F 2002/30405* (2013.01); *A61F 2002/30462* (2013.01); *A61F 2002/30471* (2013.01); *A61F 2002/30495* (2013.01); *A61F 2002/30537* (2013.01); *A61F 2002/30538* (2013.01); *A61F 2002/30579* (2013.01); *A61F 2002/30601* (2013.01); *A61F 2002/30616* (2013.01); *A61F 2002/30841* (2013.01); *A61F 2002/30884* (2013.01); *A61F 2002/443* (2013.01); *A61F 2002/448* (2013.01); *A61F 2002/4415* (2013.01); *A61F 2002/4485* (2013.01); *A61F 2002/4627* (2013.01); *A61F 2002/4628* (2013.01); *A61F 2220/0025* (2013.01); *A61F 2220/0075* (2013.01); *A61F 2220/0091* (2013.01); *A61F 2250/0006* (2013.01); *A61F 2310/00023* (2013.01)

(56) References Cited

U.S. PATENT DOCUMENTS

| | | |
|---|---|---|
| 1,965,653 A | 7/1934 | Kennedy |
| 2,077,804 A | 4/1937 | Morrison |
| 2,115,250 A | 4/1938 | Bruson |
| 2,121,193 A | 6/1938 | Hanicke |
| 2,170,111 A | 8/1939 | Bruson |
| 2,173,655 A | 9/1939 | Neracher et al. |
| 2,229,024 A | 1/1941 | Bruson |
| 2,243,717 A | 5/1941 | Moreira |
| 2,381,050 A | 8/1945 | Hardinge |
| 2,388,056 A | 10/1945 | Hendricks |
| 2,485,531 A | 10/1949 | William et al. |
| 2,489,870 A | 11/1949 | Dzus |
| 2,570,465 A | 10/1951 | Lundholm |
| 2,677,369 A | 5/1954 | Knowles |
| 2,706,701 A | 4/1955 | Hans et al. |
| 2,710,277 A | 6/1955 | Shelanski et al. |
| 2,826,532 A | 3/1958 | Hosmer |
| 2,900,305 A | 8/1959 | Siggia |
| 2,977,315 A | 3/1961 | Scheib et al. |
| 3,091,237 A | 5/1963 | Skinner |
| 3,112,743 A | 12/1963 | Cochran et al. |
| 3,115,804 A | 12/1963 | Johnson |
| 3,228,828 A | 1/1966 | Romano |
| 3,312,139 A | 4/1967 | Di Cristina |
| 3,486,505 A | 12/1969 | Morrison |
| 3,489,143 A | 1/1970 | Halloran |
| 3,648,294 A | 3/1972 | Shahrestani |
| 3,698,391 A | 10/1972 | Mahony |
| 3,717,655 A | 2/1973 | Godefroi et al. |
| 3,760,802 A | 9/1973 | Fischer et al. |
| 3,800,788 A | 4/1974 | White |
| 3,805,775 A | 4/1974 | Fischer et al. |
| 3,811,449 A | 5/1974 | Gravlee et al. |
| 3,842,825 A | 10/1974 | Wagner |
| 3,848,601 A | 11/1974 | Ma et al. |
| 3,855,638 A | 12/1974 | Pilliar |
| 3,867,728 A | 2/1975 | Stubstad et al. |
| 3,875,595 A | 4/1975 | Froning |
| 3,889,665 A | 6/1975 | Ling et al. |
| 3,964,480 A | 6/1976 | Froning |
| 3,986,504 A | 10/1976 | Avila |
| 4,013,071 A | 3/1977 | Rosenberg |
| 4,052,988 A | 10/1977 | Doddi et al. |
| 4,091,806 A | 5/1978 | Aginsky |
| 4,105,034 A | 8/1978 | Shalaby et al. |
| 4,130,639 A | 12/1978 | Shalaby et al. |
| 4,140,678 A | 2/1979 | Shalaby et al. |
| 4,141,087 A | 2/1979 | Shalaby et al. |
| 4,175,555 A | 11/1979 | Herbert |
| 4,205,399 A | 6/1980 | Jamiolkowski et al. |
| 4,236,512 A | 12/1980 | Aginsky |
| 4,249,435 A | 2/1981 | Smith et al. |
| 4,262,665 A | 4/1981 | Roalstad et al. |
| 4,262,676 A | 4/1981 | Jamshidi |
| 4,274,163 A | 6/1981 | Malcom et al. |
| 4,275,717 A | 6/1981 | Bolesky |
| 4,312,337 A | 1/1982 | Donohue |
| 4,312,353 A | 1/1982 | Shahbabian |
| 4,313,434 A | 2/1982 | Segal |
| 4,341,206 A | 7/1982 | Perrett et al. |
| 4,349,921 A | 9/1982 | Kuntz |
| 4,350,151 A | 9/1982 | Scott |
| 4,351,069 A | 9/1982 | Ballintyn et al. |
| 4,352,883 A | 10/1982 | Lim |
| 4,369,790 A | 1/1983 | McCarthy |
| 4,399,814 A | 8/1983 | Pratt et al. |
| 4,401,112 A | 8/1983 | Rezaian |
| 4,401,433 A | 8/1983 | Luther |
| 4,409,974 A | 10/1983 | Freedland |
| 4,440,921 A | 4/1984 | Allcock et al. |
| 4,449,532 A | 5/1984 | Storz |
| 4,451,256 A | 5/1984 | Weikl et al. |
| 4,456,005 A | 6/1984 | Lichty |
| 4,462,394 A | 7/1984 | Jacobs |
| 4,463,753 A | 8/1984 | Gustilo |
| 4,466,435 A | 8/1984 | Murray |
| 4,467,479 A | 8/1984 | Brody |
| 4,488,543 A | 12/1984 | Tornier |
| 4,488,549 A | 12/1984 | Lee et al. |
| 4,494,535 A | 1/1985 | Haig |
| 4,495,174 A | 1/1985 | Allcock et al. |
| 4,532,660 A | 8/1985 | Field |
| 4,537,185 A | 8/1985 | Stednitz |
| 4,538,612 A | 9/1985 | Patrick, Jr. |
| 4,542,539 A | 9/1985 | Rowe et al. |
| 4,545,374 A | 10/1985 | Jacobson |
| 4,562,598 A | 1/1986 | Kranz |
| 4,573,448 A | 3/1986 | Kambin |
| 4,595,006 A | 6/1986 | Burke et al. |
| 4,601,710 A | 7/1986 | Moll |
| 4,625,722 A | 12/1986 | Murray |
| 4,625,725 A | 12/1986 | Davison et al. |
| 4,627,434 A | 12/1986 | Murray |
| 4,628,945 A | 12/1986 | Johnson, Jr. |
| 4,629,450 A | 12/1986 | Suzuki et al. |
| 4,630,616 A | 12/1986 | Tretinyak |
| 4,632,101 A | 12/1986 | Freedland |
| 4,640,271 A | 2/1987 | Lower |
| 4,641,640 A | 2/1987 | Griggs |
| 4,645,503 A | 2/1987 | Lin et al. |
| 4,646,741 A | 3/1987 | Smith |
| 4,651,717 A | 3/1987 | Jakubczak |
| 4,653,489 A | 3/1987 | Tronzo |
| 4,665,906 A | 5/1987 | Jervis |
| 4,667,663 A | 5/1987 | Miyata |
| 4,686,973 A | 8/1987 | Frisch |
| 4,686,984 A | 8/1987 | Bonnet |
| 4,688,561 A | 8/1987 | Reese |
| 4,697,584 A | 10/1987 | Haynes |
| 4,706,670 A | 11/1987 | Andersen et al. |

(56) References Cited

U.S. PATENT DOCUMENTS

| | | |
|---|---|---|
| 4,714,469 A | 12/1987 | Kenna |
| 4,714,478 A | 12/1987 | Fischer |
| 4,721,103 A | 1/1988 | Freedland |
| 4,723,544 A | 2/1988 | Moore et al. |
| 4,743,256 A | 5/1988 | Brantigan |
| 4,743,257 A | 5/1988 | Toermaelae et al. |
| 4,759,766 A | 7/1988 | Buettner-Janz et al. |
| 4,760,843 A | 8/1988 | Fischer et al. |
| 4,772,287 A | 9/1988 | Ray et al. |
| 4,790,304 A | 12/1988 | Rosenberg |
| 4,790,817 A | 12/1988 | Luther |
| 4,796,612 A | 1/1989 | Reese |
| 4,802,479 A | 2/1989 | Haber et al. |
| 4,815,909 A | 3/1989 | Simons |
| 4,827,917 A | 5/1989 | Brumfield |
| 4,834,069 A | 5/1989 | Umeda |
| 4,834,757 A | 5/1989 | Brantigan |
| 4,838,282 A | 6/1989 | Strasser et al. |
| 4,858,601 A | 8/1989 | Glisson |
| 4,862,891 A | 9/1989 | Smith |
| 4,863,476 A | 9/1989 | Shepperd |
| 4,870,153 A | 9/1989 | Matzner et al. |
| 4,871,366 A | 10/1989 | Von et al. |
| 4,873,976 A | 10/1989 | Schreiber |
| 4,878,915 A | 11/1989 | Brantigan |
| 4,880,622 A | 11/1989 | Allcock et al. |
| 4,888,022 A | 12/1989 | Huebsch |
| 4,888,024 A | 12/1989 | Powlan |
| 4,889,119 A | 12/1989 | Jamiolkowski et al. |
| 4,892,550 A | 1/1990 | Huebsch |
| 4,896,662 A | 1/1990 | Noble |
| 4,898,186 A | 2/1990 | Ikada et al. |
| 4,898,577 A | 2/1990 | Badger et al. |
| 4,903,692 A | 2/1990 | Reese |
| 4,904,261 A | 2/1990 | Dove et al. |
| 4,911,718 A | 3/1990 | Lee et al. |
| 4,917,554 A | 4/1990 | Bronn |
| 4,932,969 A | 6/1990 | Frey et al. |
| 4,940,467 A | 7/1990 | Tronzo |
| 4,941,466 A | 7/1990 | Romano |
| 4,946,378 A | 8/1990 | Hirayama et al. |
| 4,959,064 A | 9/1990 | Engelhardt |
| 4,961,740 A | 10/1990 | Ray et al. |
| 4,963,144 A | 10/1990 | Huene |
| 4,966,587 A | 10/1990 | Baumgart |
| 4,968,317 A | 11/1990 | Toermaelae et al. |
| 4,969,888 A | 11/1990 | Scholten et al. |
| 4,978,334 A | 12/1990 | Toye et al. |
| 4,978,349 A | 12/1990 | Frigg |
| 4,981,482 A | 1/1991 | Ichikawa |
| 4,988,351 A | 1/1991 | Paulos et al. |
| 4,994,027 A | 2/1991 | Farrell |
| 4,995,200 A | 2/1991 | Eberhart |
| 5,002,557 A | 3/1991 | Hasson |
| 5,006,121 A | 4/1991 | Hafeli |
| 5,011,484 A | 4/1991 | Breard |
| 5,013,315 A | 5/1991 | Barrows |
| 5,013,316 A | 5/1991 | Goble et al. |
| 5,015,247 A | 5/1991 | Michelson |
| 5,015,255 A | 5/1991 | Kuslich |
| 5,019,082 A | 5/1991 | Frey et al. |
| 5,030,233 A | 7/1991 | Ducheyne |
| 5,051,189 A | 9/1991 | Farrah |
| 5,053,035 A | 10/1991 | McLaren |
| 5,055,104 A | 10/1991 | Ray |
| 5,059,193 A | 10/1991 | Kuslich |
| 5,062,849 A | 11/1991 | Schelhas |
| 5,071,435 A | 12/1991 | Fuchs et al. |
| 5,071,437 A | 12/1991 | Steffee |
| 5,080,662 A | 1/1992 | Paul |
| 5,084,043 A | 1/1992 | Hertzmann et al. |
| 5,092,891 A | 3/1992 | Kummer et al. |
| 5,098,241 A | 3/1992 | Aldridge et al. |
| 5,098,433 A | 3/1992 | Freedland |
| 5,098,435 A | 3/1992 | Stednitz et al. |
| 5,102,413 A | 4/1992 | Poddar |
| 5,108,404 A | 4/1992 | Scholten et al. |
| 5,114,407 A | 5/1992 | Burbank |
| 5,116,336 A | 5/1992 | Frigg |
| 5,120,171 A | 6/1992 | Lasner |
| 5,122,130 A | 6/1992 | Keller |
| 5,122,133 A | 6/1992 | Evans |
| 5,122,141 A | 6/1992 | Simpson et al. |
| 5,123,926 A | 6/1992 | Pisharodi |
| 5,133,719 A | 7/1992 | Winston |
| 5,133,755 A | 7/1992 | Brekke |
| 5,134,477 A | 7/1992 | Knauer et al. |
| 5,139,486 A | 8/1992 | Moss |
| 5,147,366 A | 9/1992 | Arroyo et al. |
| 5,158,543 A | 10/1992 | Lazarus |
| 5,163,939 A | 11/1992 | Winston |
| 5,163,989 A | 11/1992 | Campbell et al. |
| 5,167,663 A | 12/1992 | Brumfield |
| 5,167,664 A | 12/1992 | Hodorek |
| 5,169,400 A | 12/1992 | Muehling et al. |
| 5,169,402 A | 12/1992 | Elloy |
| 5,171,278 A | 12/1992 | Pisharodi |
| 5,171,279 A | 12/1992 | Mathews |
| 5,171,280 A | 12/1992 | Baumgartner |
| 5,176,651 A | 1/1993 | Allgood et al. |
| 5,176,683 A | 1/1993 | Kimsey et al. |
| 5,176,692 A | 1/1993 | Wilk et al. |
| 5,176,697 A | 1/1993 | Hasson et al. |
| 5,178,501 A | 1/1993 | Carstairs |
| 5,183,052 A | 2/1993 | Terwilliger |
| 5,183,464 A | 2/1993 | Dubrul et al. |
| 5,188,118 A | 2/1993 | Terwilliger |
| 5,192,327 A | 3/1993 | Brantigan |
| 5,195,506 A | 3/1993 | Hulfish |
| 5,201,742 A | 4/1993 | Hasson |
| 5,217,462 A | 6/1993 | Asnis et al. |
| 5,217,475 A | 6/1993 | Kuber |
| 5,217,486 A | 6/1993 | Rice et al. |
| 5,224,952 A | 7/1993 | Deniega et al. |
| 5,228,441 A | 7/1993 | Lundquist |
| 5,234,431 A | 8/1993 | Keller |
| 5,241,972 A | 9/1993 | Bonati |
| 5,242,410 A | 9/1993 | Melker |
| 5,242,447 A | 9/1993 | Borzone |
| 5,242,448 A | 9/1993 | Pettine et al. |
| 5,242,879 A | 9/1993 | Abe et al. |
| 5,246,441 A | 9/1993 | Ross et al. |
| 5,250,049 A | 10/1993 | Michael |
| 5,250,061 A | 10/1993 | Michelson |
| 5,257,632 A | 11/1993 | Turkel et al. |
| 5,263,953 A | 11/1993 | Bagby |
| 5,269,797 A | 12/1993 | Bonati et al. |
| 5,280,782 A | 1/1994 | Wilk |
| 5,285,795 A | 2/1994 | Ryan et al. |
| 5,286,001 A | 2/1994 | Rafeld |
| 5,290,243 A | 3/1994 | Chodorow et al. |
| 5,290,312 A | 3/1994 | Kojimoto et al. |
| 5,300,074 A | 4/1994 | Frigg |
| 5,303,718 A | 4/1994 | Krajicek |
| 5,304,142 A | 4/1994 | Liebl et al. |
| 5,306,307 A | 4/1994 | Senter et al. |
| 5,306,308 A | 4/1994 | Gross et al. |
| 5,306,309 A | 4/1994 | Wagner et al. |
| 5,306,310 A | 4/1994 | Siebels |
| 5,308,327 A | 5/1994 | Heaven et al. |
| 5,308,352 A | 5/1994 | Koutrouvelis |
| 5,312,410 A | 5/1994 | Miller et al. |
| 5,312,417 A | 5/1994 | Wilk |
| 5,314,477 A | 5/1994 | Marnay |
| 5,320,644 A | 6/1994 | Baumgartner |
| 5,322,505 A | 6/1994 | Krause et al. |
| 5,324,261 A | 6/1994 | Amundson et al. |
| 5,330,429 A | 7/1994 | Noguchi et al. |
| 5,331,975 A | 7/1994 | Bonutti |
| 5,334,184 A | 8/1994 | Bimman |
| 5,334,204 A | 8/1994 | Clewett et al. |
| 5,342,365 A | 8/1994 | Waldman |
| 5,342,382 A | 8/1994 | Brinkerhoff et al. |
| 5,344,252 A | 9/1994 | Kakimoto |

(56) References Cited

U.S. PATENT DOCUMENTS

| | | |
|---|---|---|
| 5,361,752 A | 11/1994 | Moll et al. |
| 5,364,398 A | 11/1994 | Chapman et al. |
| 5,370,646 A | 12/1994 | Reese et al. |
| 5,370,647 A | 12/1994 | Graber et al. |
| 5,370,661 A | 12/1994 | Branch |
| 5,370,697 A | 12/1994 | Baumgartner |
| 5,372,660 A | 12/1994 | Davidson et al. |
| 5,374,267 A | 12/1994 | Siegal |
| 5,382,248 A | 1/1995 | Jacobson et al. |
| 5,383,932 A | 1/1995 | Wilson et al. |
| 5,385,151 A | 1/1995 | Scarfone et al. |
| 5,387,213 A | 2/1995 | Breard et al. |
| 5,387,215 A | 2/1995 | Fisher |
| 5,390,683 A * | 2/1995 | Pisharodi .............. A61F 2/4455 606/279 |
| 5,395,317 A | 3/1995 | Kambin |
| 5,395,371 A | 3/1995 | Miller et al. |
| 5,397,364 A | 3/1995 | Kozak et al. |
| 5,401,269 A | 3/1995 | Buettner-Janz et al. |
| 5,407,430 A | 4/1995 | Peters |
| 5,410,016 A | 4/1995 | Hubbell et al. |
| 5,415,661 A | 5/1995 | Holmes |
| 5,423,816 A | 6/1995 | Lin |
| 5,423,817 A | 6/1995 | Lin |
| 5,423,850 A | 6/1995 | Berger |
| 5,424,773 A | 6/1995 | Saito |
| 5,425,773 A | 6/1995 | Boyd et al. |
| 5,431,658 A | 7/1995 | Moskovich |
| 5,441,538 A | 8/1995 | Bonutti |
| 5,443,514 A | 8/1995 | Steffee |
| 5,449,359 A | 9/1995 | Groiso |
| 5,449,361 A | 9/1995 | Preissman |
| 5,452,748 A | 9/1995 | Simmons et al. |
| 5,454,365 A | 10/1995 | Bonutti |
| 5,454,790 A | 10/1995 | Dubrul |
| 5,454,815 A | 10/1995 | Geisser et al. |
| 5,454,827 A | 10/1995 | Aust et al. |
| 5,456,686 A | 10/1995 | Klapper et al. |
| 5,458,641 A | 10/1995 | Ramirez Jimenez |
| 5,458,643 A | 10/1995 | Oka et al. |
| 5,462,563 A | 10/1995 | Shearer et al. |
| 5,464,427 A | 11/1995 | Curtis et al. |
| 5,464,929 A | 11/1995 | Bezwada et al. |
| 5,468,245 A | 11/1995 | Vargas, III |
| 5,470,333 A | 11/1995 | Ray |
| 5,472,426 A | 12/1995 | Bonati et al. |
| 5,474,539 A | 12/1995 | Costa et al. |
| 5,480,400 A | 1/1996 | Berger |
| 5,484,437 A | 1/1996 | Michelson |
| 5,486,190 A | 1/1996 | Green |
| 5,496,318 A | 3/1996 | Howland et al. |
| 5,498,265 A | 3/1996 | Asnis et al. |
| 5,501,695 A | 3/1996 | Anspach et al. |
| 5,505,710 A | 4/1996 | Dorsey, III |
| 5,507,816 A | 4/1996 | Bullivant |
| 5,509,923 A | 4/1996 | Middleman et al. |
| 5,512,037 A | 4/1996 | Russell et al. |
| 5,514,143 A | 5/1996 | Bonutti et al. |
| 5,514,153 A | 5/1996 | Bonutti |
| 5,514,180 A | 5/1996 | Heggeness et al. |
| 5,520,690 A | 5/1996 | Errico et al. |
| 5,520,896 A | 5/1996 | De et al. |
| 5,522,398 A | 6/1996 | Goldenberg et al. |
| 5,522,790 A | 6/1996 | Moll et al. |
| 5,522,846 A | 6/1996 | Bonutti |
| 5,522,895 A | 6/1996 | Mikos |
| 5,522,899 A | 6/1996 | Michelson |
| 5,527,312 A | 6/1996 | Ray |
| 5,527,343 A | 6/1996 | Bonutti |
| 5,527,624 A | 6/1996 | Higgins et al. |
| 5,531,856 A | 7/1996 | Moll et al. |
| 5,534,023 A | 7/1996 | Henley |
| 5,534,029 A | 7/1996 | Shima |
| 5,534,030 A | 7/1996 | Navarro et al. |
| 5,536,127 A | 7/1996 | Pennig |
| 5,538,009 A | 7/1996 | Byrne et al. |
| 5,540,688 A | 7/1996 | Navas |
| 5,540,693 A | 7/1996 | Fisher |
| 5,540,711 A | 7/1996 | Kieturakis et al. |
| 5,545,164 A | 8/1996 | Howland |
| 5,545,222 A | 8/1996 | Bonutti |
| 5,549,610 A | 8/1996 | Russell et al. |
| 5,549,679 A | 8/1996 | Kuslich |
| 5,554,191 A | 9/1996 | Lahille et al. |
| 5,556,431 A | 9/1996 | Buettner-Janz |
| 5,558,674 A | 9/1996 | Heggeness et al. |
| D374,287 S | 10/1996 | Goble et al. |
| 5,562,736 A | 10/1996 | Ray et al. |
| 5,562,738 A | 10/1996 | Boyd et al. |
| 5,564,926 A | 10/1996 | Braanemark |
| 5,569,248 A | 10/1996 | Mathews |
| 5,569,251 A | 10/1996 | Baker et al. |
| 5,569,290 A | 10/1996 | McAfee |
| 5,569,548 A | 10/1996 | Koike et al. |
| 5,571,109 A | 11/1996 | Bertagnoli |
| 5,571,189 A | 11/1996 | Kuslich |
| 5,571,190 A | 11/1996 | Ulrich et al. |
| 5,575,790 A | 11/1996 | Chen et al. |
| 5,591,168 A | 1/1997 | Judet et al. |
| 5,593,409 A | 1/1997 | Michelson |
| 5,595,751 A | 1/1997 | Bezwada et al. |
| 5,597,579 A | 1/1997 | Bezwada et al. |
| 5,601,556 A | 2/1997 | Pisharodi |
| 5,601,561 A | 2/1997 | Terry et al. |
| 5,601,572 A | 2/1997 | Middleman et al. |
| 5,607,687 A | 3/1997 | Bezwada et al. |
| 5,609,634 A | 3/1997 | Voydeville |
| 5,609,635 A | 3/1997 | Michelson |
| 5,613,950 A | 3/1997 | Yoon |
| 5,618,142 A | 4/1997 | Sonden et al. |
| 5,618,314 A | 4/1997 | Harwin et al. |
| 5,618,552 A | 4/1997 | Bezwada et al. |
| 5,620,698 A | 4/1997 | Bezwada et al. |
| 5,624,447 A | 4/1997 | Myers |
| 5,626,613 A | 5/1997 | Schmieding |
| 5,628,751 A | 5/1997 | Sander et al. |
| 5,628,752 A | 5/1997 | Asnis et al. |
| 5,632,746 A | 5/1997 | Middleman et al. |
| 5,639,276 A | 6/1997 | Weinstock et al. |
| 5,643,320 A | 7/1997 | Lower et al. |
| 5,645,589 A | 7/1997 | Li |
| 5,645,596 A | 7/1997 | Kim et al. |
| 5,645,597 A | 7/1997 | Krapiva |
| 5,645,599 A | 7/1997 | Samani |
| 5,645,850 A | 7/1997 | Bezwada et al. |
| 5,647,857 A | 7/1997 | Anderson et al. |
| 5,648,088 A | 7/1997 | Bezwada et al. |
| 5,649,931 A | 7/1997 | Bryant et al. |
| 5,653,763 A | 8/1997 | Errico et al. |
| 5,658,335 A | 8/1997 | Allen |
| 5,662,683 A | 9/1997 | Kay |
| 5,665,095 A | 9/1997 | Jacobson et al. |
| 5,665,122 A | 9/1997 | Kambin |
| 5,667,508 A | 9/1997 | Errico et al. |
| 5,669,915 A | 9/1997 | Caspar et al. |
| 5,669,926 A | 9/1997 | Aust et al. |
| 5,674,294 A | 10/1997 | Bainville et al. |
| 5,674,295 A | 10/1997 | Ray et al. |
| 5,674,296 S | 10/1997 | Bryan et al. |
| 5,676,701 A | 10/1997 | Yuan et al. |
| 5,679,723 A | 10/1997 | Cooper et al. |
| 5,681,263 A | 10/1997 | Flesch |
| 5,683,465 A | 11/1997 | Shinn et al. |
| 5,693,100 A | 12/1997 | Pisharodi |
| 5,695,513 A | 12/1997 | Johnson et al. |
| 5,697,977 A | 12/1997 | Pisharodi |
| 5,698,213 A | 12/1997 | Jamiolkowski et al. |
| 5,700,239 A | 12/1997 | Yoon |
| 5,700,583 A | 12/1997 | Jamiolkowski et al. |
| 5,702,391 A | 12/1997 | Lin |
| 5,702,449 A | 12/1997 | McKay |
| 5,702,450 A | 12/1997 | Bisserie |
| 5,702,453 A | 12/1997 | Rabbe et al. |
| 5,702,454 A | 12/1997 | Baumgartner |

(56) References Cited

U.S. PATENT DOCUMENTS

| | | |
|---|---|---|
| 5,707,359 A | 1/1998 | Bufalini |
| 5,713,870 A | 2/1998 | Yoon |
| 5,713,903 A | 2/1998 | Sander et al. |
| 5,716,415 A | 2/1998 | Steffee |
| 5,716,416 A | 2/1998 | Lin |
| 5,720,753 A | 2/1998 | Sander et al. |
| 5,725,531 A | 3/1998 | Shapiro |
| 5,725,541 A | 3/1998 | Anspach et al. |
| 5,725,588 A | 3/1998 | Errico et al. |
| 5,728,097 A | 3/1998 | Mathews |
| 5,728,116 A | 3/1998 | Rosenman |
| 5,735,853 A | 4/1998 | Olerud |
| 5,741,253 A | 4/1998 | Michelson |
| 5,741,282 A | 4/1998 | Anspach et al. |
| 5,743,881 A | 4/1998 | Demco |
| 5,743,912 A | 4/1998 | Lahille et al. |
| 5,743,914 A | 4/1998 | Skiba |
| 5,749,879 A | 5/1998 | Middleman et al. |
| 5,749,889 A | 5/1998 | Bacich et al. |
| 5,752,969 A | 5/1998 | Cunci et al. |
| 5,755,797 A | 5/1998 | Baumgartner |
| 5,755,798 A | 5/1998 | Papavero et al. |
| 5,756,127 A | 5/1998 | Grisoni et al. |
| 5,762,500 A | 6/1998 | Lazarof |
| 5,762,629 A | 6/1998 | Kambin |
| 5,766,252 A | 6/1998 | Henry et al. |
| 5,772,661 A | 6/1998 | Michelson |
| 5,772,662 A | 6/1998 | Chapman et al. |
| 5,772,678 A | 6/1998 | Thomason et al. |
| 5,776,156 A | 7/1998 | Shikhman |
| 5,782,800 A | 7/1998 | Yoon |
| 5,782,832 A | 7/1998 | Larsen et al. |
| 5,782,865 A | 7/1998 | Grotz |
| 5,788,703 A | 8/1998 | Mittelmeier et al. |
| 5,792,044 A | 8/1998 | Foley et al. |
| 5,797,909 A | 8/1998 | Michelson |
| 5,800,549 A | 9/1998 | Bao et al. |
| 5,807,275 A | 9/1998 | Jamshidi |
| 5,807,327 A | 9/1998 | Green et al. |
| 5,810,721 A | 9/1998 | Mueller et al. |
| 5,810,821 A | 9/1998 | Vandewalle |
| 5,810,866 A | 9/1998 | Yoon |
| 5,814,084 A | 9/1998 | Grivas et al. |
| 5,820,628 A | 10/1998 | Middleman et al. |
| 5,823,979 A | 10/1998 | Mezo |
| 5,824,084 A | 10/1998 | Muschler |
| 5,824,093 A | 10/1998 | Ray et al. |
| 5,824,094 A | 10/1998 | Serhan et al. |
| 5,827,289 A | 10/1998 | Reiley et al. |
| 5,833,657 A | 11/1998 | Reinhardt et al. |
| 5,836,948 A | 11/1998 | Zucherman et al. |
| 5,837,752 A | 11/1998 | Shastri et al. |
| 5,846,259 A | 12/1998 | Berthiaume |
| 5,848,986 A | 12/1998 | Lundquist et al. |
| 5,849,004 A | 12/1998 | Bramlet |
| 5,851,212 A | 12/1998 | Zirps et al. |
| 5,851,216 A | 12/1998 | Allen |
| 5,857,995 A | 1/1999 | Thomas et al. |
| 5,859,150 A | 1/1999 | Jamiolkowski et al. |
| 5,860,973 A | 1/1999 | Michelson |
| 5,860,977 A | 1/1999 | Zucherman et al. |
| 5,865,846 A | 2/1999 | Bryan et al. |
| 5,865,848 A | 2/1999 | Baker |
| 5,871,485 A | 2/1999 | Rao et al. |
| 5,873,854 A | 2/1999 | Wolvek |
| 5,876,404 A | 3/1999 | Zucherman et al. |
| 5,888,220 A | 3/1999 | Felt et al. |
| 5,888,221 A | 3/1999 | Gelbard |
| 5,888,223 A | 3/1999 | Bray, Jr. |
| 5,888,224 A | 3/1999 | Beckers et al. |
| 5,888,226 A | 3/1999 | Rogozinski |
| 5,888,227 A | 3/1999 | Cottle |
| 5,888,228 A | 3/1999 | Knothe et al. |
| 5,893,850 A | 4/1999 | Cachia |
| 5,893,889 A | 4/1999 | Harrington |
| 5,893,890 A | 4/1999 | Pisharodi |
| 5,895,428 A | 4/1999 | Berry |
| 5,902,231 A | 5/1999 | Foley et al. |
| 5,904,690 A | 5/1999 | Middleman et al. |
| 5,904,696 A | 5/1999 | Rosenman |
| 5,908,422 A | 6/1999 | Bresina |
| 5,916,228 A | 6/1999 | Ripich et al. |
| 5,916,267 A | 6/1999 | Tienboon |
| 5,919,235 A | 7/1999 | Husson et al. |
| 5,925,056 A | 7/1999 | Thomas et al. |
| 5,925,074 A | 7/1999 | Gingras et al. |
| 5,928,235 A | 7/1999 | Friedl |
| 5,928,244 A | 7/1999 | Tovey et al. |
| 5,931,870 A | 8/1999 | Cuckler et al. |
| 5,935,129 A | 8/1999 | McDevitt et al. |
| 5,947,999 A | 9/1999 | Groiso |
| 5,948,000 A | 9/1999 | Larsen et al. |
| 5,954,635 A | 9/1999 | Foley et al. |
| 5,954,722 A | 9/1999 | Bono |
| 5,954,747 A | 9/1999 | Clark |
| 5,957,902 A | 9/1999 | Teves |
| 5,957,924 A | 9/1999 | Toermaelae et al. |
| 5,961,554 A | 10/1999 | Janson et al. |
| 5,964,730 A | 10/1999 | Williams et al. |
| 5,964,761 A | 10/1999 | Kambin |
| 5,967,783 A | 10/1999 | Ura |
| 5,967,970 A | 10/1999 | Cowan et al. |
| 5,968,044 A | 10/1999 | Nicholson et al. |
| 5,968,098 A | 10/1999 | Winslow |
| 5,972,015 A | 10/1999 | Scribner et al. |
| 5,972,385 A | 10/1999 | Liu et al. |
| 5,976,139 A | 11/1999 | Bramlet |
| 5,976,146 A | 11/1999 | Ogawa et al. |
| 5,976,186 A | 11/1999 | Bao |
| 5,976,187 A | 11/1999 | Richelsoph |
| 5,980,522 A | 11/1999 | Koros et al. |
| 5,984,927 A | 11/1999 | Wenstrom et al. |
| 5,984,966 A | 11/1999 | Kiema et al. |
| 5,985,307 A | 11/1999 | Hanson et al. |
| 5,989,255 A | 11/1999 | Pepper et al. |
| 5,989,291 A | 11/1999 | Ralph et al. |
| 5,993,459 A | 11/1999 | Larsen et al. |
| 5,997,510 A | 12/1999 | Schwemberger |
| 5,997,538 A | 12/1999 | Asnis et al. |
| 5,997,541 A | 12/1999 | Schenk |
| 6,001,100 A | 12/1999 | Sherman et al. |
| 6,001,101 A | 12/1999 | Augagneur et al. |
| 6,004,327 A | 12/1999 | Asnis et al. |
| 6,005,161 A | 12/1999 | Brekke |
| 6,007,519 A | 12/1999 | Rosselli |
| 6,007,566 A | 12/1999 | Wenstrom, Jr. |
| 6,007,580 A | 12/1999 | Lehto et al. |
| 6,010,508 A | 1/2000 | Bradley |
| 6,010,513 A | 1/2000 | Toermaelae et al. |
| 6,012,494 A | 1/2000 | Balazs |
| 6,015,410 A | 1/2000 | Toermaelae et al. |
| 6,015,436 A | 1/2000 | Schoenhoeffer |
| 6,019,762 A | 2/2000 | Cole |
| 6,019,792 A | 2/2000 | Cauthen |
| 6,019,793 A | 2/2000 | Perren et al. |
| 6,022,350 A | 2/2000 | Ganem |
| 6,022,352 A | 2/2000 | Vandewalle |
| 6,030,162 A | 2/2000 | Huebner |
| 6,030,364 A | 2/2000 | Durgin et al. |
| 6,030,401 A | 2/2000 | Marino |
| 6,033,406 A | 3/2000 | Mathews |
| 6,033,412 A | 3/2000 | Losken et al. |
| 6,036,701 A | 3/2000 | Rosenman |
| 6,039,740 A | 3/2000 | Olerud |
| 6,039,761 A | 3/2000 | Li et al. |
| 6,039,763 A | 3/2000 | Shelokov |
| 6,045,552 A | 4/2000 | Zucherman et al. |
| 6,045,579 A | 4/2000 | Hochschuler et al. |
| 6,048,309 A | 4/2000 | Flom et al. |
| 6,048,342 A | 4/2000 | Zucherman et al. |
| 6,048,346 A | 4/2000 | Reiley et al. |
| 6,048,360 A | 4/2000 | Khosravi et al. |
| 6,049,026 A | 4/2000 | Muschler |
| 6,053,922 A | 4/2000 | Krause et al. |

(56) References Cited

U.S. PATENT DOCUMENTS

| | | |
|---|---|---|
| 6,053,935 A | 4/2000 | Brenneman et al. |
| 6,056,763 A | 5/2000 | Parsons |
| 6,063,121 A | 5/2000 | Xavier et al. |
| 6,066,142 A | 5/2000 | Serbousek et al. |
| 6,066,154 A | 5/2000 | Reiley et al. |
| 6,066,175 A | 5/2000 | Henderson et al. |
| 6,068,630 A | 5/2000 | Zucherman et al. |
| 6,068,648 A | 5/2000 | Cole et al. |
| 6,071,982 A | 6/2000 | Wise et al. |
| 6,073,051 A | 6/2000 | Sharkey et al. |
| 6,074,390 A | 6/2000 | Zucherman et al. |
| 6,080,155 A | 6/2000 | Michelson |
| 6,080,158 A | 6/2000 | Lin |
| 6,080,193 A | 6/2000 | Hochschuler et al. |
| 6,083,225 A | 7/2000 | Winslow et al. |
| 6,083,244 A | 7/2000 | Lubbers et al. |
| 6,090,112 A | 7/2000 | Zucherman et al. |
| 6,090,143 A | 7/2000 | Meriwether et al. |
| 6,096,038 A | 8/2000 | Michelson |
| 6,096,080 A | 8/2000 | Nicholson et al. |
| 6,099,531 A | 8/2000 | Bonutti |
| 6,102,914 A | 8/2000 | Bulstra et al. |
| 6,102,950 A | 8/2000 | Vaccaro |
| 6,106,557 A | 8/2000 | Robioneck et al. |
| 6,110,210 A | 8/2000 | Norton et al. |
| 6,113,624 A | 9/2000 | Bezwada et al. |
| 6,113,637 A | 9/2000 | Gill et al. |
| 6,113,638 A | 9/2000 | Williams et al. |
| 6,113,640 A | 9/2000 | Toermaelae et al. |
| 6,117,174 A | 9/2000 | Nolan |
| 6,119,044 A | 9/2000 | Kuzma |
| 6,120,508 A | 9/2000 | Gruenig et al. |
| 6,123,705 A | 9/2000 | Michelson |
| 6,123,711 A | 9/2000 | Winters |
| 6,126,660 A | 10/2000 | Dietz |
| 6,126,661 A | 10/2000 | Faccioli et al. |
| 6,126,663 A | 10/2000 | Hair |
| 6,126,686 A | 10/2000 | Badylak et al. |
| 6,126,689 A | 10/2000 | Brett |
| 6,127,597 A | 10/2000 | Beyar et al. |
| 6,129,762 A | 10/2000 | Li |
| 6,129,763 A | 10/2000 | Chauvin et al. |
| 6,132,435 A | 10/2000 | Young |
| 6,136,031 A | 10/2000 | Middleton |
| 6,139,558 A | 10/2000 | Wagner |
| 6,139,579 A | 10/2000 | Steffee et al. |
| 6,146,384 A | 11/2000 | Lee et al. |
| 6,146,387 A | 11/2000 | Trott et al. |
| 6,146,420 A | 11/2000 | McKay |
| 6,146,421 A | 11/2000 | Gordon et al. |
| 6,147,135 A | 11/2000 | Yuan et al. |
| 6,149,652 A | 11/2000 | Zucherman et al. |
| 6,152,926 A | 11/2000 | Zucherman et al. |
| 6,156,038 A | 12/2000 | Zucherman et al. |
| 6,159,179 A | 12/2000 | Simonson |
| 6,159,211 A | 12/2000 | Boriani et al. |
| 6,159,244 A | 12/2000 | Suddaby |
| 6,161,350 A | 12/2000 | Espinosa |
| 6,162,234 A | 12/2000 | Freedland et al. |
| 6,162,236 A | 12/2000 | Osada |
| 6,162,252 A | 12/2000 | Kuras et al. |
| 6,165,218 A | 12/2000 | Husson et al. |
| 6,165,486 A | 12/2000 | Marra et al. |
| 6,168,595 B1 | 1/2001 | Durham et al. |
| 6,168,597 B1 | 1/2001 | Biedermann et al. |
| 6,171,610 B1 | 1/2001 | Vacanti et al. |
| 6,174,337 B1 | 1/2001 | Keenan |
| 6,175,758 B1 | 1/2001 | Kambin |
| 6,176,882 B1 | 1/2001 | Biedermann et al. |
| 6,179,794 B1 | 1/2001 | Burras |
| 6,179,873 B1 | 1/2001 | Zientek |
| 6,183,471 B1 | 2/2001 | Zucherman et al. |
| 6,183,472 B1 | 2/2001 | Lutz |
| 6,183,474 B1 | 2/2001 | Bramlet et al. |
| 6,183,517 B1 | 2/2001 | Suddaby |
| 6,187,043 B1 | 2/2001 | Ledergerber |
| 6,187,048 B1 | 2/2001 | Milner et al. |
| 6,190,387 B1 | 2/2001 | Zucherman et al. |
| 6,190,414 B1 | 2/2001 | Young et al. |
| 6,193,757 B1 | 2/2001 | Foley et al. |
| 6,197,033 B1 | 3/2001 | Haid et al. |
| 6,197,041 B1 | 3/2001 | Shichman et al. |
| 6,197,065 B1 | 3/2001 | Martin et al. |
| 6,197,325 B1 | 3/2001 | MacPhee et al. |
| 6,200,322 B1 | 3/2001 | Branch et al. |
| 6,203,565 B1 | 3/2001 | Bonutti et al. |
| 6,206,826 B1 | 3/2001 | Mathews et al. |
| 6,206,922 B1 | 3/2001 | Zdeblick et al. |
| D439,980 S | 4/2001 | Reiley et al. |
| 6,213,957 B1 | 4/2001 | Milliman et al. |
| 6,214,368 B1 | 4/2001 | Lee et al. |
| 6,217,509 B1 | 4/2001 | Foley et al. |
| 6,217,579 B1 | 4/2001 | Koros |
| 6,221,082 B1 | 4/2001 | Marino et al. |
| 6,224,603 B1 | 5/2001 | Marino |
| 6,224,631 B1 | 5/2001 | Kohrs |
| 6,224,894 B1 | 5/2001 | Jamiolkowski et al. |
| 6,228,058 B1 | 5/2001 | Dennis et al. |
| 6,231,606 B1 | 5/2001 | Graf et al. |
| 6,235,030 B1 | 5/2001 | Zucherman et al. |
| 6,235,043 B1 | 5/2001 | Reiley et al. |
| 6,238,397 B1 | 5/2001 | Zucherman et al. |
| 6,238,491 B1 | 5/2001 | Davidson et al. |
| 6,241,733 B1 | 6/2001 | Nicholson et al. |
| 6,241,734 B1 | 6/2001 | Scribner et al. |
| 6,241,769 B1 | 6/2001 | Nicholson et al. |
| 6,245,107 B1 | 6/2001 | Ferree |
| 6,248,108 B1 | 6/2001 | Toermaelae et al. |
| 6,248,110 B1 | 6/2001 | Reiley et al. |
| 6,248,131 B1 | 6/2001 | Felt et al. |
| 6,251,111 B1 | 6/2001 | Barker et al. |
| 6,251,140 B1 | 6/2001 | Marino et al. |
| 6,258,093 B1 | 7/2001 | Edwards et al. |
| 6,261,289 B1 | 7/2001 | Levy |
| 6,264,676 B1 | 7/2001 | Gellman et al. |
| 6,264,695 B1 | 7/2001 | Stoy |
| 6,267,763 B1 | 7/2001 | Castro |
| 6,267,765 B1 | 7/2001 | Taylor et al. |
| 6,267,767 B1 | 7/2001 | Strobel et al. |
| 6,277,149 B1 | 8/2001 | Boyle et al. |
| 6,280,444 B1 | 8/2001 | Zucherman et al. |
| 6,280,456 B1 | 8/2001 | Scribner et al. |
| 6,280,474 B1 | 8/2001 | Cassidy et al. |
| 6,280,475 B1 | 8/2001 | Bao et al. |
| 6,287,313 B1 | 9/2001 | Sasso |
| 6,290,724 B1 | 9/2001 | Marino |
| 6,293,909 B1 | 9/2001 | Chu et al. |
| 6,293,952 B1 | 9/2001 | Brosens et al. |
| D449,691 S | 10/2001 | Reiley et al. |
| 6,296,644 B1 | 10/2001 | Saurat et al. |
| 6,296,647 B1 | 10/2001 | Robioneck et al. |
| 6,302,914 B1 | 10/2001 | Michelson |
| 6,306,136 B1 | 10/2001 | Baccelli |
| 6,306,177 B1 | 10/2001 | Felt et al. |
| D450,676 S | 11/2001 | Huttner |
| 6,312,443 B1 | 11/2001 | Stone |
| 6,319,254 B1 | 11/2001 | Giet et al. |
| 6,319,272 B1 | 11/2001 | Brenneman et al. |
| 6,331,312 B1 | 12/2001 | Lee et al. |
| 6,332,882 B1 | 12/2001 | Zucherman et al. |
| 6,332,883 B1 | 12/2001 | Zucherman et al. |
| 6,332,894 B1 | 12/2001 | Stalcup et al. |
| 6,332,895 B1 | 12/2001 | Suddaby |
| 6,342,074 B1 | 1/2002 | Simpson |
| 6,346,092 B1 | 2/2002 | Leschinsky |
| 6,348,053 B1 | 2/2002 | Cachia |
| 6,355,043 B1 | 3/2002 | Adam |
| 6,361,537 B1 | 3/2002 | Anderson |
| 6,361,538 B1 | 3/2002 | Fenaroli et al. |
| 6,361,557 B1 | 3/2002 | Gittings et al. |
| 6,364,828 B1 | 4/2002 | Yeung et al. |
| 6,364,897 B1 | 4/2002 | Bonutti |
| 6,368,325 B1 | 4/2002 | McKinley et al. |
| 6,368,350 B1 | 4/2002 | Erickson et al. |

(56) References Cited

U.S. PATENT DOCUMENTS

| | | |
|---|---|---|
| 6,368,351 B1 | 4/2002 | Glenn et al. |
| 6,371,971 B1 | 4/2002 | Tsugita et al. |
| 6,371,989 B1 | 4/2002 | Chauvin et al. |
| 6,375,681 B1 | 4/2002 | Truscott |
| 6,375,682 B1 | 4/2002 | Fleischmann et al. |
| 6,375,683 B1 | 4/2002 | Crozet et al. |
| 6,379,355 B1 | 4/2002 | Zucherman et al. |
| 6,379,363 B1 | 4/2002 | Herrington et al. |
| 6,387,130 B1 | 5/2002 | Stone et al. |
| 6,398,793 B1 | 6/2002 | McGuire |
| 6,402,750 B1 | 6/2002 | Atkinson et al. |
| 6,409,766 B1 | 6/2002 | Brett |
| 6,409,767 B1 | 6/2002 | Perice et al. |
| 6,413,278 B1 | 7/2002 | Marchosky |
| 6,416,551 B1 | 7/2002 | Keller |
| 6,419,641 B1 | 7/2002 | Mark et al. |
| 6,419,676 B1 | 7/2002 | Zucherman et al. |
| 6,419,677 B2 | 7/2002 | Zucherman et al. |
| 6,419,704 B1 | 7/2002 | Ferree |
| 6,419,705 B1 | 7/2002 | Erickson |
| 6,419,706 B1 | 7/2002 | Graf |
| 6,423,061 B1 | 7/2002 | Bryant |
| 6,423,067 B1 | 7/2002 | Eisermann |
| 6,423,071 B1 | 7/2002 | Lawson |
| 6,423,083 B2 | 7/2002 | Reiley et al. |
| 6,423,089 B1 | 7/2002 | Gingras et al. |
| 6,425,887 B1 | 7/2002 | McGuckin et al. |
| 6,425,919 B1 | 7/2002 | Lambrecht |
| 6,425,920 B1 | 7/2002 | Hamada |
| 6,428,541 B1 | 8/2002 | Boyd et al. |
| 6,428,556 B1 | 8/2002 | Chin |
| 6,436,101 B1 | 8/2002 | Hamada |
| 6,436,140 B1 | 8/2002 | Liu et al. |
| 6,436,143 B1 | 8/2002 | Ross et al. |
| 6,440,138 B1 | 8/2002 | Reiley et al. |
| 6,440,154 B2 | 8/2002 | Gellman et al. |
| 6,440,169 B1 | 8/2002 | Elberg et al. |
| 6,443,989 B1 | 9/2002 | Jackson |
| 6,447,518 B1 | 9/2002 | Krause et al. |
| 6,447,527 B1 | 9/2002 | Thompson et al. |
| 6,447,540 B1 | 9/2002 | Fontaine et al. |
| 6,450,989 B2 | 9/2002 | Dubrul et al. |
| 6,451,019 B1 | 9/2002 | Zucherman et al. |
| 6,451,020 B1 | 9/2002 | Zucherman et al. |
| 6,454,806 B1 | 9/2002 | Cohen et al. |
| 6,454,807 B1 | 9/2002 | Jackson |
| 6,458,134 B1 | 10/2002 | Songer et al. |
| 6,461,359 B1 | 10/2002 | Tribus et al. |
| 6,468,277 B1 | 10/2002 | Justin et al. |
| 6,468,279 B1 | 10/2002 | Reo |
| 6,468,309 B1 | 10/2002 | Lieberman |
| 6,468,310 B1 | 10/2002 | Ralph et al. |
| 6,471,724 B2 | 10/2002 | Zdeblick et al. |
| 6,475,226 B1 | 11/2002 | Belef et al. |
| 6,478,029 B1 | 11/2002 | Boyd et al. |
| 6,478,796 B2 | 11/2002 | Zucherman et al. |
| 6,478,805 B1 | 11/2002 | Marino et al. |
| 6,482,235 B1 | 11/2002 | Lambrecht et al. |
| 6,485,491 B1 | 11/2002 | Farris et al. |
| 6,485,518 B1 | 11/2002 | Cornwall et al. |
| D467,657 S | 12/2002 | Scribner |
| 6,488,693 B2 | 12/2002 | Gannoe et al. |
| 6,488,710 B2 | 12/2002 | Besselink |
| 6,489,309 B1 | 12/2002 | Singh et al. |
| 6,491,626 B1 | 12/2002 | Stone et al. |
| 6,491,695 B1 | 12/2002 | Roggenbuck |
| 6,491,714 B1 | 12/2002 | Bennett |
| 6,491,724 B1 | 12/2002 | Ferree |
| 6,494,860 B2 | 12/2002 | Rocamora et al. |
| 6,494,883 B1 | 12/2002 | Ferree |
| 6,494,893 B2 | 12/2002 | Dubrul |
| 6,498,421 B1 | 12/2002 | Oh et al. |
| 6,500,178 B2 | 12/2002 | Zucherman et al. |
| 6,500,205 B1 | 12/2002 | Michelson |
| 6,506,192 B1 | 1/2003 | Gertzman et al. |
| 6,508,839 B1 | 1/2003 | Lambrecht et al. |
| 6,511,471 B2 | 1/2003 | Rosenman et al. |
| 6,511,481 B2 | 1/2003 | Von et al. |
| 6,512,958 B1 | 1/2003 | Swoyer et al. |
| D469,871 S | 2/2003 | Sand |
| 6,514,256 B2 | 2/2003 | Zucherman et al. |
| 6,517,543 B1 | 2/2003 | Berrevoets et al. |
| 6,517,580 B1 | 2/2003 | Ramadan et al. |
| 6,520,907 B1 | 2/2003 | Foley et al. |
| 6,520,991 B2 | 2/2003 | Huene |
| D472,323 S | 3/2003 | Sand |
| 6,527,774 B2 | 3/2003 | Lieberman |
| 6,527,803 B1 | 3/2003 | Crozet et al. |
| 6,527,804 B1 | 3/2003 | Gauchet et al. |
| 6,530,930 B1 | 3/2003 | Marino et al. |
| 6,533,791 B1 | 3/2003 | Betz et al. |
| 6,533,797 B1 | 3/2003 | Stone et al. |
| 6,533,818 B1 | 3/2003 | Weber et al. |
| 6,540,747 B1 | 4/2003 | Marino |
| 6,544,265 B2 | 4/2003 | Lieberman |
| 6,547,793 B1 | 4/2003 | McGuire |
| 6,547,795 B2 | 4/2003 | Schneiderman |
| 6,547,823 B2 | 4/2003 | Scarborough et al. |
| 6,551,319 B2 | 4/2003 | Lieberman |
| 6,551,322 B1 | 4/2003 | Lieberman |
| 6,554,831 B1 | 4/2003 | Rivard et al. |
| 6,554,833 B2 | 4/2003 | Levy et al. |
| 6,554,852 B1 | 4/2003 | Oberlander |
| 6,558,389 B2 | 5/2003 | Clark et al. |
| 6,558,390 B2 | 5/2003 | Cragg |
| 6,558,424 B2 | 5/2003 | Thalgott |
| 6,562,046 B2 | 5/2003 | Sasso |
| 6,562,049 B1 | 5/2003 | Norlander et al. |
| 6,562,072 B1 | 5/2003 | Fuss et al. |
| 6,562,074 B2 | 5/2003 | Gerbec et al. |
| 6,575,919 B1 | 6/2003 | Reiley et al. |
| 6,575,979 B1 | 6/2003 | Cragg |
| 6,576,016 B1 | 6/2003 | Hochshuler et al. |
| 6,579,291 B1 | 6/2003 | Keith et al. |
| 6,579,293 B1 | 6/2003 | Chandran |
| 6,579,320 B1 | 6/2003 | Gauchet et al. |
| 6,579,321 B1 | 6/2003 | Gordon et al. |
| 6,582,390 B1 | 6/2003 | Sanderson |
| 6,582,431 B1 | 6/2003 | Ray |
| 6,582,433 B2 | 6/2003 | Yun |
| 6,582,437 B2 | 6/2003 | Dorchak et al. |
| 6,582,441 B1 | 6/2003 | He et al. |
| 6,582,453 B1 | 6/2003 | Tran et al. |
| 6,582,466 B1 | 6/2003 | Gauchet |
| 6,582,467 B1 | 6/2003 | Teitelbaum et al. |
| 6,582,468 B1 | 6/2003 | Gauchet |
| 6,585,730 B1 | 7/2003 | Foerster |
| 6,585,740 B2 | 7/2003 | Schlapfer et al. |
| 6,589,240 B2 | 7/2003 | Hinchliffe |
| 6,589,249 B2 | 7/2003 | Sater et al. |
| 6,592,553 B2 | 7/2003 | Zhang et al. |
| 6,592,624 B1 | 7/2003 | Fraser et al. |
| 6,592,625 B2 | 7/2003 | Cauthen |
| 6,595,998 B2 | 7/2003 | Johnson et al. |
| 6,596,008 B1 | 7/2003 | Kambin |
| 6,599,294 B2 | 7/2003 | Fuss et al. |
| 6,599,297 B1 | 7/2003 | Carlsson et al. |
| 6,602,293 B1 | 8/2003 | Biermann et al. |
| 6,607,530 B1 | 8/2003 | Carl et al. |
| 6,607,544 B1 | 8/2003 | Boucher et al. |
| 6,607,558 B2 | 8/2003 | Kuras |
| 6,610,066 B2 | 8/2003 | Dinger et al. |
| 6,610,091 B1 | 8/2003 | Reiley |
| 6,610,094 B2 | 8/2003 | Husson |
| 6,613,050 B1 | 9/2003 | Wagner et al. |
| 6,613,054 B2 | 9/2003 | Scribner et al. |
| 6,616,678 B2 | 9/2003 | Nishtala et al. |
| 6,620,196 B1 | 9/2003 | Trieu |
| 6,623,505 B2 | 9/2003 | Scribner et al. |
| 6,626,943 B2 | 9/2003 | Eberlein et al. |
| 6,626,944 B1 | 9/2003 | Taylor |
| 6,629,998 B1 | 10/2003 | Lin |
| 6,632,224 B2 | 10/2003 | Cachia et al. |
| 6,632,235 B2 | 10/2003 | Weikel et al. |

(56) References Cited

U.S. PATENT DOCUMENTS

| | | |
|---|---|---|
| 6,635,059 B2 | 10/2003 | Randall et al. |
| 6,635,060 B2 | 10/2003 | Hanson et al. |
| 6,635,362 B2 | 10/2003 | Zheng |
| RE38,335 E | 11/2003 | Aust et al. |
| D482,787 S | 11/2003 | Reiss |
| 6,641,564 B1 | 11/2003 | Kraus |
| 6,641,582 B1 | 11/2003 | Hanson et al. |
| 6,641,587 B2 | 11/2003 | Scribner et al. |
| 6,641,614 B1 | 11/2003 | Wagner et al. |
| 6,645,213 B2 | 11/2003 | Sand et al. |
| 6,645,248 B2 | 11/2003 | Casutt |
| 6,648,890 B2 | 11/2003 | Culbert et al. |
| 6,648,893 B2 | 11/2003 | Dudasik |
| 6,648,917 B2 | 11/2003 | Gerbec et al. |
| 6,652,527 B2 | 11/2003 | Zucherman et al. |
| 6,652,592 B1 | 11/2003 | Grooms et al. |
| D483,495 S | 12/2003 | Sand |
| 6,655,962 B1 | 12/2003 | Kennard |
| 6,656,178 B1 | 12/2003 | Veldhuizen et al. |
| 6,656,180 B2 | 12/2003 | Stahurski |
| 6,660,004 B2 | 12/2003 | Barker et al. |
| 6,660,037 B1 | 12/2003 | Husson et al. |
| 6,663,647 B2 | 12/2003 | Reiley et al. |
| 6,666,890 B2 | 12/2003 | Michelson |
| 6,666,891 B2 | 12/2003 | Boehm et al. |
| 6,669,698 B1 | 12/2003 | Tromanhauser et al. |
| 6,669,729 B2 | 12/2003 | Chin |
| 6,669,732 B2 | 12/2003 | Serhan et al. |
| 6,673,074 B2 | 1/2004 | Shluzas |
| 6,676,663 B2 | 1/2004 | Higueras et al. |
| 6,676,664 B1 | 1/2004 | Al-Assir |
| 6,676,665 B2 | 1/2004 | Foley et al. |
| 6,679,833 B2 | 1/2004 | Smith et al. |
| 6,679,915 B1 | 1/2004 | Cauthen |
| 6,682,535 B2 | 1/2004 | Hoogland |
| 6,682,561 B2 | 1/2004 | Songer et al. |
| 6,682,562 B2 | 1/2004 | Viart et al. |
| 6,685,706 B2 | 2/2004 | Padget et al. |
| 6,685,742 B1 | 2/2004 | Jackson |
| 6,689,125 B1 | 2/2004 | Keith et al. |
| 6,689,152 B2 | 2/2004 | Balceta et al. |
| 6,689,168 B2 | 2/2004 | Lieberman |
| 6,692,499 B2 | 2/2004 | Toermaelae et al. |
| 6,692,563 B2 | 2/2004 | Zimmermann |
| 6,695,842 B2 | 2/2004 | Zucherman et al. |
| 6,695,851 B2 | 2/2004 | Zdeblick et al. |
| 6,699,246 B2 | 3/2004 | Zucherman et al. |
| 6,699,247 B2 | 3/2004 | Zucherman et al. |
| 6,706,070 B1 | 3/2004 | Wagner et al. |
| 6,709,458 B2 | 3/2004 | Michelson |
| 6,712,819 B2 | 3/2004 | Zucherman et al. |
| 6,716,216 B1 | 4/2004 | Boucher et al. |
| 6,716,247 B2 | 4/2004 | Michelson |
| 6,716,957 B2 | 4/2004 | Tunc |
| 6,719,760 B2 | 4/2004 | Dorchak et al. |
| 6,719,761 B1 | 4/2004 | Reiley et al. |
| 6,719,773 B1 | 4/2004 | Boucher et al. |
| 6,719,796 B2 | 4/2004 | Cohen et al. |
| 6,723,096 B1 | 4/2004 | Dorchak et al. |
| 6,723,126 B1 | 4/2004 | Berry |
| 6,723,127 B2 | 4/2004 | Ralph et al. |
| 6,723,128 B2 | 4/2004 | Uk |
| 6,726,691 B2 | 4/2004 | Osorio et al. |
| D490,159 S | 5/2004 | Sand |
| 6,730,126 B2 | 5/2004 | Boehm et al. |
| 6,733,093 B2 | 5/2004 | Deland et al. |
| 6,733,460 B2 | 5/2004 | Ogura |
| 6,733,532 B1 | 5/2004 | Gauchet et al. |
| 6,733,534 B2 | 5/2004 | Sherman |
| 6,733,535 B2 | 5/2004 | Michelson |
| 6,733,635 B1 | 5/2004 | Ozawa et al. |
| 6,740,090 B1 | 5/2004 | Cragg et al. |
| 6,740,093 B2 | 5/2004 | Hochschuler et al. |
| 6,740,117 B2 | 5/2004 | Ralph et al. |
| D492,032 S | 6/2004 | Muller et al. |
| 6,743,166 B2 | 6/2004 | Berci et al. |
| 6,743,255 B2 | 6/2004 | Ferree |
| 6,746,451 B2 | 6/2004 | Middleton et al. |
| 6,749,560 B1 | 6/2004 | Konstorum et al. |
| 6,752,831 B2 | 6/2004 | Sybert et al. |
| 6,755,837 B2 | 6/2004 | Ebner |
| 6,755,841 B2 | 6/2004 | Fraser et al. |
| D492,775 S | 7/2004 | Doelling et al. |
| D493,533 S | 7/2004 | Blain |
| 6,758,673 B2 | 7/2004 | Fromovich et al. |
| 6,758,847 B2 | 7/2004 | Maguire |
| 6,758,861 B2 | 7/2004 | Ralph et al. |
| 6,758,862 B2 | 7/2004 | Berry et al. |
| 6,761,720 B1 | 7/2004 | Senegas |
| 6,764,491 B2 | 7/2004 | Frey et al. |
| 6,764,514 B1 | 7/2004 | Li et al. |
| D495,417 S | 8/2004 | Doelling et al. |
| 6,770,075 B2 | 8/2004 | Howland |
| 6,773,460 B2 | 8/2004 | Jackson |
| 6,780,151 B2 | 8/2004 | Grabover et al. |
| 6,783,530 B1 | 8/2004 | Levy |
| 6,790,210 B1 | 9/2004 | Cragg et al. |
| 6,793,656 B1 | 9/2004 | Mathews |
| 6,793,678 B2 | 9/2004 | Hawkins |
| 6,793,679 B2 | 9/2004 | Michelson |
| 6,796,983 B1 | 9/2004 | Zucherman et al. |
| 6,805,685 B2 | 10/2004 | Taylor |
| 6,805,695 B2 | 10/2004 | Keith et al. |
| 6,805,697 B1 | 10/2004 | Helm et al. |
| 6,805,714 B2 | 10/2004 | Sutcliffe |
| 6,808,526 B1 | 10/2004 | Magerl et al. |
| 6,808,537 B2 | 10/2004 | Michelson |
| 6,814,736 B2 | 11/2004 | Reiley et al. |
| 6,814,756 B1 | 11/2004 | Michelson |
| 6,821,298 B1 | 11/2004 | Jackson |
| 6,824,565 B2 | 11/2004 | Muhanna et al. |
| 6,830,589 B2 | 12/2004 | Erickson |
| 6,835,205 B2 | 12/2004 | Atkinson et al. |
| 6,835,206 B2 | 12/2004 | Jackson |
| 6,835,208 B2 | 12/2004 | Marchosky |
| 6,840,941 B2 | 1/2005 | Rogers et al. |
| 6,840,944 B2 | 1/2005 | Suddaby |
| 6,852,126 B2 | 2/2005 | Ahlgren |
| 6,852,127 B2 | 2/2005 | Varga et al. |
| 6,852,129 B2 | 2/2005 | Gerbec et al. |
| 6,855,167 B2 | 2/2005 | Shimp et al. |
| 6,863,668 B2 | 3/2005 | Gillespie et al. |
| 6,863,672 B2 | 3/2005 | Reiley et al. |
| 6,863,673 B2 | 3/2005 | Gerbec et al. |
| 6,866,682 B1 | 3/2005 | An et al. |
| 6,875,215 B2 | 4/2005 | Taras et al. |
| 6,878,167 B2 | 4/2005 | Ferree |
| 6,881,228 B2 | 4/2005 | Zdeblick et al. |
| 6,881,229 B2 | 4/2005 | Khandkar et al. |
| 6,883,520 B2 | 4/2005 | Lambrecht et al. |
| 6,887,243 B2 | 5/2005 | Culbert |
| 6,887,248 B2 | 5/2005 | McKinley et al. |
| 6,890,333 B2 | 5/2005 | Von et al. |
| 6,893,464 B2 | 5/2005 | Kiester |
| 6,893,466 B2 | 5/2005 | Trieu |
| 6,899,716 B2 | 5/2005 | Cragg |
| 6,899,719 B2 | 5/2005 | Reiley et al. |
| 6,899,735 B2 | 5/2005 | Coates et al. |
| D506,828 S | 6/2005 | Layne et al. |
| 6,902,566 B2 | 6/2005 | Zucherman et al. |
| 6,905,512 B2 | 6/2005 | Paes et al. |
| 6,908,465 B2 | 6/2005 | Von et al. |
| 6,908,506 B2 | 6/2005 | Zimmermann |
| 6,916,323 B2 | 7/2005 | Kitchens |
| 6,921,403 B2 | 7/2005 | Cragg et al. |
| 6,923,810 B1 | 8/2005 | Michelson |
| 6,923,811 B1 | 8/2005 | Carl et al. |
| 6,923,813 B2 | 8/2005 | Phillips et al. |
| 6,923,814 B1 | 8/2005 | Hildebrand et al. |
| 6,929,606 B2 | 8/2005 | Ritland |
| 6,929,647 B2 | 8/2005 | Cohen |
| 6,936,071 B1 | 8/2005 | Marnay et al. |
| 6,936,072 B2 | 8/2005 | Lambrecht et al. |
| 6,942,668 B2 | 9/2005 | Padget et al. |

(56) References Cited

U.S. PATENT DOCUMENTS

| | | |
|---|---|---|
| 6,945,973 B2 | 9/2005 | Bray |
| 6,945,975 B2 | 9/2005 | Dalton |
| 6,946,000 B2 | 9/2005 | Senegas et al. |
| 6,949,100 B1 | 9/2005 | Venturini |
| 6,949,108 B2 | 9/2005 | Holmes |
| 6,951,561 B2 | 10/2005 | Warren et al. |
| 6,952,129 B2 | 10/2005 | Lin et al. |
| 6,953,477 B2 | 10/2005 | Berry |
| 6,955,691 B2 | 10/2005 | Chae et al. |
| 6,962,606 B2 | 11/2005 | Michelson |
| 6,964,674 B1 | 11/2005 | Matsuura et al. |
| 6,964,686 B2 | 11/2005 | Gordon |
| 6,966,910 B2 | 11/2005 | Ritland |
| 6,966,912 B2 | 11/2005 | Michelson |
| 6,969,404 B2 | 11/2005 | Ferree |
| 6,969,405 B2 | 11/2005 | Suddaby |
| D512,506 S | 12/2005 | Layne et al. |
| 6,972,035 B2 | 12/2005 | Michelson |
| 6,974,479 B2 | 12/2005 | Trieu |
| 6,979,341 B2 | 12/2005 | Scribner et al. |
| 6,979,352 B2 | 12/2005 | Reynolds |
| 6,979,353 B2 | 12/2005 | Bresina |
| 6,981,981 B2 | 1/2006 | Reiley et al. |
| 6,997,929 B2 | 2/2006 | Manzi et al. |
| 7,004,945 B2 | 2/2006 | Boyd et al. |
| 7,004,971 B2 | 2/2006 | Serhan et al. |
| 7,008,431 B2 | 3/2006 | Simonson |
| 7,008,453 B1 | 3/2006 | Michelson |
| 7,014,633 B2 | 3/2006 | Cragg |
| 7,018,089 B2 | 3/2006 | Wenz et al. |
| 7,018,412 B2 | 3/2006 | Ferreira et al. |
| 7,018,415 B1 | 3/2006 | McKay |
| 7,018,416 B2 | 3/2006 | Hanson et al. |
| 7,018,453 B2 | 3/2006 | Klein et al. |
| 7,022,138 B2 | 4/2006 | Mashburn |
| 7,025,746 B2 | 4/2006 | Tal |
| 7,025,787 B2 | 4/2006 | Bryan et al. |
| 7,029,473 B2 | 4/2006 | Zucherman et al. |
| 7,029,498 B2 | 4/2006 | Boehm et al. |
| 7,037,339 B2 | 5/2006 | Houfburg |
| 7,041,107 B2 | 5/2006 | Pohjonen et al. |
| 7,044,954 B2 | 5/2006 | Reiley et al. |
| 7,048,694 B2 | 5/2006 | Mark et al. |
| 7,048,736 B2 | 5/2006 | Robinson et al. |
| 7,060,068 B2 | 6/2006 | Tromanhauser et al. |
| 7,060,073 B2 | 6/2006 | Frey et al. |
| 7,063,701 B2 | 6/2006 | Michelson |
| 7,063,702 B2 | 6/2006 | Michelson |
| 7,063,703 B2 | 6/2006 | Reo |
| 7,063,725 B2 | 6/2006 | Foley |
| 7,066,960 B1 | 6/2006 | Dickman |
| 7,066,961 B2 | 6/2006 | Michelson |
| 7,069,087 B2 | 6/2006 | Sharkey et al. |
| 7,070,598 B2 | 7/2006 | Lim et al. |
| 7,070,601 B2 | 7/2006 | Culbert et al. |
| 7,074,203 B1 | 7/2006 | Johanson et al. |
| 7,074,226 B2 | 7/2006 | Roehm et al. |
| 7,081,120 B2 | 7/2006 | Li et al. |
| 7,081,122 B1 | 7/2006 | Reiley et al. |
| 7,083,650 B2 | 8/2006 | Moskowitz et al. |
| 7,087,053 B2 | 8/2006 | Vanney |
| 7,087,055 B2 | 8/2006 | Lim et al. |
| 7,087,083 B2 | 8/2006 | Pasquet et al. |
| 7,089,063 B2 | 8/2006 | Lesh et al. |
| 7,094,239 B1 | 8/2006 | Michelson |
| 7,094,257 B2 | 8/2006 | Mujwid et al. |
| 7,094,258 B2 | 8/2006 | Lambrecht et al. |
| 7,101,375 B2 | 9/2006 | Zucherman et al. |
| 7,114,501 B2 | 10/2006 | Johnson et al. |
| 7,115,128 B2 | 10/2006 | Michelson |
| 7,115,163 B2 | 10/2006 | Zimmermann |
| 7,118,572 B2 | 10/2006 | Bramlet et al. |
| 7,118,579 B2 | 10/2006 | Michelson |
| 7,118,580 B1 | 10/2006 | Beyersdorff et al. |
| 7,118,598 B2 | 10/2006 | Michelson |
| 7,124,761 B2 | 10/2006 | Lambrecht et al. |
| 7,125,424 B2 | 10/2006 | Banick et al. |
| 7,128,760 B2 | 10/2006 | Michelson |
| 7,135,424 B2 | 11/2006 | Worley et al. |
| 7,153,304 B2 | 12/2006 | Robie et al. |
| 7,153,305 B2 | 12/2006 | Johnson et al. |
| 7,153,306 B2 | 12/2006 | Ralph et al. |
| 7,153,307 B2 | 12/2006 | Scribner et al. |
| D536,096 S | 1/2007 | Hoogland et al. |
| 7,156,874 B2 | 1/2007 | Paponneau et al. |
| 7,156,875 B2 | 1/2007 | Michelson |
| 7,156,876 B2 | 1/2007 | Moumene et al. |
| 7,156,877 B2 | 1/2007 | Lotz et al. |
| 7,163,558 B2 | 1/2007 | Senegas et al. |
| 7,166,107 B2 | 1/2007 | Anderson |
| 7,172,612 B2 | 2/2007 | Ishikawa |
| 7,179,293 B2 | 2/2007 | McKay |
| 7,179,294 B2 | 2/2007 | Eisermann et al. |
| 7,189,242 B2 | 3/2007 | Boyd et al. |
| 7,201,751 B2 | 4/2007 | Zucherman et al. |
| 7,204,851 B2 | 4/2007 | Trieu et al. |
| 7,207,991 B2 | 4/2007 | Michelson |
| 7,211,112 B2 | 5/2007 | Baynham et al. |
| 7,214,227 B2 | 5/2007 | Colleran et al. |
| 7,217,291 B2 | 5/2007 | Zucherman et al. |
| 7,217,293 B2 | 5/2007 | Branch, Jr. |
| 7,220,280 B2 | 5/2007 | Kast et al. |
| 7,220,281 B2 | 5/2007 | Lambrecht et al. |
| 7,223,227 B2 | 5/2007 | Pflueger |
| 7,223,292 B2 | 5/2007 | Messerli et al. |
| 7,226,481 B2 | 6/2007 | Kuslich |
| 7,226,482 B2 | 6/2007 | Messerli et al. |
| 7,226,483 B2 | 6/2007 | Gerber et al. |
| 7,235,101 B2 | 6/2007 | Berry et al. |
| 7,238,204 B2 | 7/2007 | Le et al. |
| 7,241,297 B2 | 7/2007 | Shaolian et al. |
| 7,244,273 B2 | 7/2007 | Pedersen et al. |
| 7,250,060 B2 | 7/2007 | Trieu |
| 7,252,671 B2 | 8/2007 | Scribner et al. |
| 7,267,683 B2 | 9/2007 | Sharkey et al. |
| 7,267,687 B2 | 9/2007 | McGuckin, Jr. |
| 7,270,679 B2 | 9/2007 | Istephanous et al. |
| 7,276,062 B2 | 10/2007 | McDaniel et al. |
| 7,282,061 B2 | 10/2007 | Sharkey et al. |
| 7,291,173 B2 | 11/2007 | Richelsoph et al. |
| 7,300,440 B2 | 11/2007 | Zdeblick et al. |
| 7,306,628 B2 | 12/2007 | Zucherman et al. |
| 7,309,357 B2 | 12/2007 | Kim |
| 7,311,713 B2 | 12/2007 | Johnson et al. |
| 7,316,714 B2 | 1/2008 | Gordon et al. |
| 7,318,840 B2 | 1/2008 | McKay |
| 7,320,689 B2 | 1/2008 | Keller |
| 7,320,708 B1 | 1/2008 | Bernstein |
| 7,322,962 B2 | 1/2008 | Forrest |
| 7,326,211 B2 | 2/2008 | Padget et al. |
| 7,326,248 B2 | 2/2008 | Michelson |
| 7,335,203 B2 | 2/2008 | Winslow et al. |
| 7,351,262 B2 | 4/2008 | Bindseil et al. |
| 7,361,140 B2 | 4/2008 | Ries et al. |
| 7,371,238 B2 | 5/2008 | Soboleski et al. |
| 7,377,942 B2 | 5/2008 | Berry |
| 7,383,639 B2 | 6/2008 | Malandain |
| 7,400,930 B2 | 7/2008 | Sharkey et al. |
| 7,406,775 B2 | 8/2008 | Funk et al. |
| 7,410,501 B2 | 8/2008 | Michelson |
| 7,413,576 B2 | 8/2008 | Sybert et al. |
| 7,422,594 B2 | 9/2008 | Zander |
| 7,434,325 B2 | 10/2008 | Foley et al. |
| 7,442,211 B2 | 10/2008 | De et al. |
| 7,445,636 B2 | 11/2008 | Michelson |
| 7,445,637 B2 | 11/2008 | Taylor |
| 7,470,273 B2 | 12/2008 | Dougherty-Shah |
| D584,812 S | 1/2009 | Ries |
| 7,473,256 B2 | 1/2009 | Assell et al. |
| 7,473,268 B2 | 1/2009 | Zucherman et al. |
| 7,476,251 B2 | 1/2009 | Zucherman et al. |
| 7,485,134 B2 | 2/2009 | Simonson |
| 7,488,326 B2 | 2/2009 | Elliott |
| 7,491,237 B2 | 2/2009 | Randall et al. |

(56) References Cited

U.S. PATENT DOCUMENTS

| | | |
|---|---|---|
| 7,500,991 B2 | 3/2009 | Bartish et al. |
| 7,503,920 B2 | 3/2009 | Siegal |
| 7,503,933 B2 | 3/2009 | Michelson |
| 7,507,241 B2 | 3/2009 | Levy et al. |
| 7,517,363 B2 | 4/2009 | Rogers et al. |
| 7,520,888 B2 | 4/2009 | Trieu |
| 7,547,317 B2 | 6/2009 | Cragg |
| 7,556,629 B2 | 7/2009 | Von et al. |
| 7,556,651 B2 | 7/2009 | Humphreys et al. |
| 7,569,054 B2 | 8/2009 | Michelson |
| 7,569,074 B2 | 8/2009 | Eisermann et al. |
| 7,572,279 B2 | 8/2009 | Jackson |
| 7,575,580 B2 | 8/2009 | Lim et al. |
| 7,575,599 B2 | 8/2009 | Villiers et al. |
| 7,578,820 B2 | 8/2009 | Moore et al. |
| 7,588,574 B2 | 9/2009 | Assell et al. |
| 7,601,173 B2 | 10/2009 | Messerli et al. |
| 7,608,083 B2 | 10/2009 | Lee et al. |
| 7,618,458 B2 | 11/2009 | Biedermann et al. |
| 7,621,950 B1 | 11/2009 | Globerman et al. |
| 7,621,960 B2 | 11/2009 | Boyd et al. |
| 7,625,377 B2 | 12/2009 | Veldhuizen et al. |
| 7,625,378 B2 | 12/2009 | Foley |
| 7,625,394 B2 | 12/2009 | Molz et al. |
| 7,637,905 B2 | 12/2009 | Saadat et al. |
| 7,641,657 B2 | 1/2010 | Cragg |
| 7,641,670 B2 | 1/2010 | Davison et al. |
| 7,641,692 B2 | 1/2010 | Bryan et al. |
| 7,647,123 B2 | 1/2010 | Sharkey et al. |
| 7,648,523 B2 | 1/2010 | Mirkovic et al. |
| 7,655,010 B2 | 2/2010 | Serhan et al. |
| 7,666,186 B2 | 2/2010 | Harp |
| 7,666,266 B2 | 2/2010 | Izawa et al. |
| 7,670,354 B2 | 3/2010 | Davison et al. |
| 7,670,374 B2 | 3/2010 | Schaller |
| 7,674,265 B2 | 3/2010 | Smith et al. |
| 7,674,273 B2 | 3/2010 | Davison et al. |
| 7,682,370 B2 | 3/2010 | Pagliuca et al. |
| 7,682,400 B2 | 3/2010 | Zwirkoski |
| 7,691,120 B2 | 4/2010 | Shluzas et al. |
| 7,691,147 B2 | 4/2010 | Guetlin et al. |
| 7,699,878 B2 | 4/2010 | Pavlov et al. |
| 7,703,727 B2 | 4/2010 | Selness |
| 7,717,944 B2 | 5/2010 | Foley et al. |
| 7,722,530 B2 | 5/2010 | Davison |
| 7,722,612 B2 | 5/2010 | Sala et al. |
| 7,722,674 B1 | 5/2010 | Grotz |
| 7,727,263 B2 | 6/2010 | Cragg |
| 7,731,751 B2 | 6/2010 | Butler et al. |
| 7,740,633 B2 | 6/2010 | Assell et al. |
| 7,744,599 B2 | 6/2010 | Cragg |
| 7,744,650 B2 | 6/2010 | Lindner et al. |
| 7,749,270 B2 | 7/2010 | Peterman |
| 7,762,995 B2 | 7/2010 | Eversull et al. |
| 7,763,025 B2 | 7/2010 | Ainsworth |
| 7,763,028 B2 | 7/2010 | Lim et al. |
| 7,763,038 B2 | 7/2010 | O'Brien |
| 7,763,055 B2 | 7/2010 | Foley |
| 7,766,930 B2 | 8/2010 | Dipoto et al. |
| 7,771,473 B2 | 8/2010 | Thramann |
| 7,771,479 B2 | 8/2010 | Humphreys et al. |
| 7,785,368 B2 | 8/2010 | Schaller |
| 7,789,914 B2 | 9/2010 | Michelson |
| 7,794,463 B2 | 9/2010 | Cragg |
| 7,799,032 B2 | 9/2010 | Assell et al. |
| 7,799,033 B2 | 9/2010 | Assell et al. |
| 7,799,036 B2 | 9/2010 | Davison et al. |
| 7,799,080 B2 | 9/2010 | Doty |
| 7,799,081 B2 | 9/2010 | McKinley |
| 7,799,083 B2 | 9/2010 | Smith et al. |
| 7,803,161 B2 | 9/2010 | Foley et al. |
| D626,233 S | 10/2010 | Cipoletti et al. |
| 7,814,429 B2 | 10/2010 | Buffet et al. |
| 7,819,921 B2 | 10/2010 | Grotz |
| 7,824,410 B2 | 11/2010 | Simonson et al. |
| 7,824,429 B2 | 11/2010 | Culbert et al. |
| 7,824,445 B2 | 11/2010 | Biro et al. |
| 7,828,807 B2 | 11/2010 | Lehuec et al. |
| 7,837,734 B2 | 11/2010 | Zucherman et al. |
| 7,846,183 B2 | 12/2010 | Blain |
| 7,846,206 B2 | 12/2010 | Oglaza et al. |
| 7,850,695 B2 | 12/2010 | Pagliuca et al. |
| 7,850,733 B2 | 12/2010 | Baynham et al. |
| 7,854,766 B2 | 12/2010 | Moskowitz et al. |
| 7,857,832 B2 | 12/2010 | Culbert et al. |
| 7,857,840 B2 | 12/2010 | Krebs et al. |
| 7,862,590 B2 | 1/2011 | Lim et al. |
| 7,862,595 B2 | 1/2011 | Foley et al. |
| 7,867,259 B2 | 1/2011 | Foley et al. |
| 7,874,980 B2 | 1/2011 | Sonnenschein et al. |
| 7,875,077 B2 | 1/2011 | Humphreys et al. |
| 7,879,098 B1 | 2/2011 | Simmons, Jr. |
| 7,887,589 B2 | 2/2011 | Glenn et al. |
| 7,892,171 B2 | 2/2011 | Davison et al. |
| 7,892,249 B2 | 2/2011 | Davison et al. |
| 7,901,438 B2 | 3/2011 | Culbert et al. |
| 7,901,459 B2 | 3/2011 | Hodges et al. |
| 7,909,870 B2 | 3/2011 | Kraus |
| 7,909,874 B2 | 3/2011 | Zielinski |
| 7,918,874 B2 | 4/2011 | Siegal |
| 7,922,719 B2 | 4/2011 | Ralph et al. |
| 7,922,729 B2 | 4/2011 | Michelson |
| 7,927,373 B2 | 4/2011 | Parsons et al. |
| 7,931,674 B2 | 4/2011 | Zucherman et al. |
| 7,931,689 B2 | 4/2011 | Hochschuler et al. |
| 7,935,051 B2 | 5/2011 | Miles et al. |
| 7,938,832 B2 | 5/2011 | Culbert et al. |
| 7,942,903 B2 | 5/2011 | Moskowitz et al. |
| 7,947,078 B2 | 5/2011 | Siegal |
| 7,951,199 B2 | 5/2011 | Miller |
| 7,955,391 B2 | 6/2011 | Schaller |
| 7,959,675 B2 | 6/2011 | Gately |
| 7,963,967 B1 | 6/2011 | Woods |
| 7,963,993 B2 | 6/2011 | Schaller |
| 7,967,864 B2 | 6/2011 | Schaller |
| 7,967,865 B2 | 6/2011 | Schaller |
| 7,985,231 B2 | 7/2011 | Sankaran |
| 7,993,403 B2 | 8/2011 | Foley et al. |
| 7,998,176 B2 | 8/2011 | Culbert |
| 8,007,535 B2 | 8/2011 | Hudgins et al. |
| 8,012,212 B2 | 9/2011 | Link et al. |
| 8,021,424 B2 | 9/2011 | Beger et al. |
| 8,021,426 B2 | 9/2011 | Segal et al. |
| 8,025,697 B2 | 9/2011 | McClellan et al. |
| 8,034,109 B2 | 10/2011 | Zwirkoski |
| 8,034,110 B2 | 10/2011 | Garner et al. |
| 8,038,703 B2 | 10/2011 | Dobak et al. |
| 8,043,293 B2 | 10/2011 | Warnick |
| 8,043,381 B2 | 10/2011 | Hestad et al. |
| 8,052,754 B2 | 11/2011 | Froehlich |
| 8,057,544 B2 | 11/2011 | Schaller |
| 8,057,545 B2 | 11/2011 | Hughes et al. |
| 8,062,375 B2 | 11/2011 | Glerum et al. |
| 8,075,621 B2 | 12/2011 | Michelson |
| 8,097,036 B2 | 1/2012 | Cordaro et al. |
| 8,100,978 B2 | 1/2012 | Bass |
| 8,105,382 B2 | 1/2012 | Olmos et al. |
| 8,109,972 B2 | 2/2012 | Zucherman et al. |
| 8,109,977 B2 | 2/2012 | Culbert et al. |
| 8,114,088 B2 | 2/2012 | Miller |
| 8,118,871 B2 | 2/2012 | Gordon |
| 8,128,700 B2 | 3/2012 | Delurio et al. |
| 8,128,702 B2 | 3/2012 | Zucherman et al. |
| 8,133,232 B2 | 3/2012 | Levy et al. |
| 8,147,549 B2 | 4/2012 | Metcalf et al. |
| 8,177,812 B2 | 5/2012 | Sankaran |
| 8,187,327 B2 | 5/2012 | Edidin et al. |
| 8,192,495 B2 | 6/2012 | Simpson et al. |
| 8,202,322 B2 | 6/2012 | Doty |
| 8,206,423 B2 | 6/2012 | Siegal |
| 8,216,312 B2 | 7/2012 | Gray |
| 8,216,314 B2 | 7/2012 | Richelsoph |
| 8,216,317 B2 | 7/2012 | Thibodeau |
| 8,221,501 B2 | 7/2012 | Eisermann et al. |

(56) References Cited

U.S. PATENT DOCUMENTS

| | | |
|---|---|---|
| 8,221,502 B2 | 7/2012 | Branch, Jr. |
| 8,221,503 B2 | 7/2012 | Garcia et al. |
| 8,231,681 B2 | 7/2012 | Castleman et al. |
| 8,236,029 B2 | 8/2012 | Siegal |
| 8,236,058 B2 | 8/2012 | Fabian et al. |
| 8,241,328 B2 | 8/2012 | Siegal |
| 8,241,358 B2 | 8/2012 | Butler et al. |
| 8,241,361 B2 | 8/2012 | Link |
| 8,241,364 B2 | 8/2012 | Hansell et al. |
| 8,246,622 B2 | 8/2012 | Siegal et al. |
| 8,257,440 B2 | 9/2012 | Gordon et al. |
| 8,257,442 B2 | 9/2012 | Edie et al. |
| 8,262,666 B2 | 9/2012 | Baynham et al. |
| 8,262,736 B2 | 9/2012 | Michelson |
| 8,267,939 B2 | 9/2012 | Cipoletti et al. |
| 8,267,965 B2 | 9/2012 | Gimbel et al. |
| 8,273,128 B2 | 9/2012 | Oh et al. |
| 8,273,129 B2 | 9/2012 | Baynham et al. |
| 8,287,599 B2 | 10/2012 | McGuckin, Jr. |
| 8,292,959 B2 | 10/2012 | Webb et al. |
| 8,303,663 B2 | 11/2012 | Jimenez et al. |
| 8,313,528 B1 | 11/2012 | Wensel |
| 8,317,866 B2 | 11/2012 | Palmatier et al. |
| 8,323,345 B2 | 12/2012 | Sledge |
| 8,328,812 B2 | 12/2012 | Siegal et al. |
| 8,328,852 B2 | 12/2012 | Zehavi et al. |
| 8,337,559 B2 | 12/2012 | Hansell et al. |
| 8,343,193 B2 | 1/2013 | Johnson et al. |
| 8,343,222 B2 | 1/2013 | Cope |
| 8,353,961 B2 | 1/2013 | McClintock et al. |
| 8,361,154 B2 | 1/2013 | Reo |
| 8,366,777 B2 | 2/2013 | Matthis et al. |
| 8,377,098 B2 | 2/2013 | Landry et al. |
| 8,377,133 B2 | 2/2013 | Yuan et al. |
| 8,382,842 B2 | 2/2013 | Greenhalgh et al. |
| 8,394,129 B2 | 3/2013 | Morgenstern et al. |
| 8,398,712 B2 | 3/2013 | De et al. |
| 8,398,713 B2 | 3/2013 | Weiman |
| 8,403,990 B2 | 3/2013 | Dryer et al. |
| 8,409,282 B2 | 4/2013 | Kim |
| 8,409,290 B2 | 4/2013 | Zamani et al. |
| 8,409,291 B2 | 4/2013 | Blackwell et al. |
| 8,414,650 B2 | 4/2013 | Bertele et al. |
| 8,425,559 B2 | 4/2013 | Tebbe et al. |
| 8,435,298 B2 | 5/2013 | Weiman |
| 8,454,617 B2 | 6/2013 | Schaller et al. |
| 8,454,698 B2 | 6/2013 | De et al. |
| 8,465,524 B2 | 6/2013 | Siegal |
| 8,470,043 B2 | 6/2013 | Schaller et al. |
| 8,480,715 B2 | 7/2013 | Gray |
| 8,480,742 B2 | 7/2013 | Pisharodi |
| 8,486,109 B2 | 7/2013 | Siegal |
| 8,486,148 B2 | 7/2013 | Butler et al. |
| 8,491,591 B2 | 7/2013 | Fuerderer |
| 8,491,653 B2 | 7/2013 | Zucherman et al. |
| 8,491,657 B2 | 7/2013 | Attia et al. |
| 8,491,659 B2 | 7/2013 | Weiman |
| 8,506,635 B2 | 8/2013 | Palmatier et al. |
| 8,518,087 B2 | 8/2013 | Lopez et al. |
| 8,518,120 B2 | 8/2013 | Glerum et al. |
| 8,523,909 B2 | 9/2013 | Hess |
| 8,523,944 B2 | 9/2013 | Jimenez et al. |
| 8,535,380 B2 | 9/2013 | Greenhalgh et al. |
| 8,545,567 B1 | 10/2013 | Krueger |
| 8,551,092 B2 | 10/2013 | Morgan et al. |
| 8,551,173 B2 | 10/2013 | Lechmann et al. |
| 8,556,978 B2 | 10/2013 | Schaller |
| 8,556,979 B2 | 10/2013 | Glerum et al. |
| 8,568,481 B2 | 10/2013 | Olmos et al. |
| 8,579,977 B2 | 11/2013 | Fabian |
| 8,579,981 B2 | 11/2013 | Lim et al. |
| 8,591,583 B2 | 11/2013 | Schaller et al. |
| 8,591,585 B2 | 11/2013 | McLaughlin et al. |
| 8,597,330 B2 | 12/2013 | Siegal |
| 8,597,333 B2 | 12/2013 | Morgenstern et al. |
| 8,597,360 B2 | 12/2013 | McLuen et al. |
| 8,603,168 B2 | 12/2013 | Gordon et al. |
| 8,603,170 B2 | 12/2013 | Cipoletti et al. |
| 8,603,177 B2 | 12/2013 | Gray |
| 8,623,088 B1 | 1/2014 | Tohmeh et al. |
| 8,623,091 B2 | 1/2014 | Suedkamp et al. |
| 8,628,576 B2 | 1/2014 | Triplett et al. |
| 8,628,577 B1 | 1/2014 | Jimenez |
| 8,628,578 B2 | 1/2014 | Miller et al. |
| 8,632,595 B2 | 1/2014 | Weiman |
| 8,636,746 B2 | 1/2014 | Jimenez et al. |
| 8,641,764 B2 | 2/2014 | Gately |
| 8,663,329 B2 | 3/2014 | Ernst |
| 8,663,331 B2 | 3/2014 | McCellan et al. |
| 8,668,740 B2 | 3/2014 | Rhoda et al. |
| 8,672,977 B2 | 3/2014 | Siegal et al. |
| 8,679,161 B2 | 3/2014 | Malandain et al. |
| 8,679,183 B2 | 3/2014 | Glerum et al. |
| 8,685,095 B2 | 4/2014 | Miller et al. |
| 8,685,098 B2 | 4/2014 | Glerum et al. |
| 8,696,751 B2 | 4/2014 | Ashley et al. |
| 8,702,757 B2 | 4/2014 | Thommen et al. |
| 8,702,798 B2 | 4/2014 | Matthis et al. |
| 8,709,086 B2 | 4/2014 | Glerum |
| 8,715,351 B1 | 5/2014 | Pinto |
| 8,721,723 B2 | 5/2014 | Hansell et al. |
| 8,728,160 B2 | 5/2014 | Globerman et al. |
| 8,728,166 B2 | 5/2014 | Schwab |
| 8,740,954 B2 | 6/2014 | Ghobrial et al. |
| 8,753,398 B2 | 6/2014 | Gordon et al. |
| 8,758,349 B2 | 6/2014 | Germain et al. |
| 8,758,441 B2 | 6/2014 | Hovda et al. |
| 8,764,806 B2 | 7/2014 | Abdou |
| 8,771,360 B2 | 7/2014 | Jimenez et al. |
| 8,777,993 B2 | 7/2014 | Siegal et al. |
| 8,778,025 B2 | 7/2014 | Ragab et al. |
| 8,795,366 B2 | 8/2014 | Varela |
| 8,795,374 B2 | 8/2014 | Chee |
| 8,801,787 B2 | 8/2014 | Schaller |
| 8,801,792 B2 | 8/2014 | De et al. |
| 8,808,376 B2 | 8/2014 | Schaller |
| 8,828,085 B1 | 9/2014 | Jensen |
| 8,845,638 B2 | 9/2014 | Siegal et al. |
| 8,845,728 B1 | 9/2014 | Abdou |
| 8,845,731 B2 | 9/2014 | Weiman |
| 8,845,732 B2 | 9/2014 | Weiman |
| 8,845,733 B2 | 9/2014 | O'Neil et al. |
| 8,845,734 B2 | 9/2014 | Weiman |
| 8,852,242 B2 | 10/2014 | Morgenstern et al. |
| 8,852,243 B2 | 10/2014 | Morgenstern et al. |
| 8,852,279 B2 | 10/2014 | Weiman |
| 8,864,833 B2 | 10/2014 | Glerum et al. |
| 8,888,853 B2 | 11/2014 | Glerum et al. |
| 8,888,854 B2 | 11/2014 | Glerum et al. |
| 8,900,235 B2 | 12/2014 | Siegal |
| 8,900,307 B2 | 12/2014 | Hawkins et al. |
| 8,906,098 B2 | 12/2014 | Siegal |
| 8,920,506 B2 | 12/2014 | McGuckin, Jr. |
| 8,926,704 B2 | 1/2015 | Glerum et al. |
| 8,936,641 B2 | 1/2015 | Cain |
| 8,940,050 B2 | 1/2015 | Laurence et al. |
| 8,940,052 B2 | 1/2015 | Lechmann et al. |
| 8,961,609 B2 | 2/2015 | Schaller |
| 8,968,408 B2 | 3/2015 | Schaller et al. |
| 8,979,860 B2 | 3/2015 | Voellmicke et al. |
| 8,979,929 B2 | 3/2015 | Schaller |
| 8,986,387 B1 | 3/2015 | To et al. |
| 8,986,388 B2 | 3/2015 | Siegal et al. |
| 8,986,389 B2 | 3/2015 | Lim et al. |
| 9,005,291 B2 | 4/2015 | Loebl et al. |
| 9,017,408 B2 | 4/2015 | Siegal et al. |
| 9,017,413 B2 | 4/2015 | Siegal et al. |
| 9,039,767 B2 | 5/2015 | Raymond et al. |
| 9,039,771 B2 | 5/2015 | Glerum et al. |
| 9,044,334 B2 | 6/2015 | Siegal et al. |
| 9,044,338 B2 | 6/2015 | Schaller |
| 9,060,876 B1 | 6/2015 | To et al. |
| 9,066,808 B2 | 6/2015 | Schaller |
| 9,078,767 B1 | 7/2015 | McLean |

(56) References Cited

U.S. PATENT DOCUMENTS

| | | |
|---|---|---|
| 9,089,428 B2 | 7/2015 | Bertele et al. |
| 9,095,446 B2 | 8/2015 | Landry et al. |
| 9,095,447 B2 | 8/2015 | Barreiro et al. |
| 9,101,488 B2 | 8/2015 | Malandain |
| 9,101,489 B2 | 8/2015 | Protopsaltis et al. |
| 9,101,491 B2 | 8/2015 | Rodgers et al. |
| 9,101,492 B2 | 8/2015 | Mangione et al. |
| 9,107,766 B1 | 8/2015 | McLean et al. |
| 9,254,138 B2 | 2/2016 | Siegal et al. |
| 9,259,326 B2 | 2/2016 | Schaller |
| 9,271,846 B2 | 3/2016 | Lim et al. |
| 9,277,928 B2 | 3/2016 | Morgenstern Lopez |
| 9,283,092 B2 | 3/2016 | Siegal et al. |
| 9,295,562 B2 | 3/2016 | Lechmann et al. |
| 9,314,348 B2 | 4/2016 | Emstad |
| 9,320,615 B2 | 4/2016 | Suedkamp et al. |
| 9,326,866 B2 | 5/2016 | Schaller et al. |
| 9,333,091 B2 | 5/2016 | Dimauro |
| 9,387,087 B2 | 7/2016 | Tyber |
| 9,402,739 B2 | 8/2016 | Weiman et al. |
| 9,408,712 B2 | 8/2016 | Siegal et al. |
| 9,414,923 B2 | 8/2016 | Studer et al. |
| 9,414,934 B2 | 8/2016 | Cain |
| 9,433,510 B2 | 9/2016 | Lechmann et al. |
| 9,439,776 B2 | 9/2016 | Dimauro et al. |
| 9,439,777 B2 | 9/2016 | Dimauro |
| 9,463,099 B2 | 10/2016 | Levy et al. |
| 9,474,623 B2 | 10/2016 | Cain |
| 9,492,288 B2 | 11/2016 | Wagner et al. |
| 9,510,954 B2 | 12/2016 | Glerum et al. |
| 9,522,070 B2 | 12/2016 | Flower et al. |
| 9,566,165 B2 | 2/2017 | Lee et al. |
| 9,592,129 B2 | 3/2017 | Slivka et al. |
| 9,597,197 B2 | 3/2017 | Lechmann et al. |
| 9,662,223 B2 | 5/2017 | Matthis et al. |
| 9,724,207 B2 | 8/2017 | Dimauro et al. |
| 9,730,803 B2 | 8/2017 | Dimauro et al. |
| 9,788,963 B2 | 10/2017 | Aquino et al. |
| 9,801,729 B2 | 10/2017 | Dimauro et al. |
| 9,808,351 B2 | 11/2017 | Kelly et al. |
| 9,814,589 B2 | 11/2017 | Dimauro |
| 9,814,590 B2 | 11/2017 | Serhan et al. |
| 9,833,334 B2 | 12/2017 | Voellmicke et al. |
| 9,839,530 B2 | 12/2017 | Hawkins et al. |
| 9,918,851 B2 | 3/2018 | Willis et al. |
| 9,924,978 B2 | 3/2018 | Thommen et al. |
| 9,925,060 B2 | 3/2018 | Dimauro et al. |
| 9,931,223 B2 | 4/2018 | Cain |
| 9,949,769 B2 | 4/2018 | Serhan et al. |
| 9,980,823 B2 | 5/2018 | Matthis et al. |
| 9,987,142 B2 | 6/2018 | McConnell |
| 9,993,350 B2 * | 6/2018 | Cain ................... A61F 2/4611 |
| 10,085,843 B2 | 10/2018 | Dimauro |
| 10,182,831 B2 | 1/2019 | Marnay et al. |
| 10,238,500 B2 | 3/2019 | Rogers et al. |
| 10,265,191 B2 | 4/2019 | Lim et al. |
| 10,307,254 B2 | 6/2019 | Levy et al. |
| 10,376,372 B2 | 8/2019 | Serhan et al. |
| 10,398,566 B2 | 9/2019 | Olmos et al. |
| 10,405,986 B2 | 9/2019 | Kelly et al. |
| 10,420,651 B2 | 9/2019 | Serhan et al. |
| 10,426,632 B2 | 10/2019 | Butler et al. |
| 10,433,971 B2 | 10/2019 | Dimauro et al. |
| 10,433,974 B2 | 10/2019 | O'Neil |
| 10,433,977 B2 | 10/2019 | Lechmann et al. |
| 10,449,056 B2 | 10/2019 | Cain |
| 10,449,058 B2 | 10/2019 | Lechmann et al. |
| 10,492,918 B2 | 12/2019 | Dimauro |
| 10,512,489 B2 | 12/2019 | Serhan et al. |
| 10,555,817 B2 | 2/2020 | Dimauro et al. |
| 10,575,959 B2 | 3/2020 | Dimauro et al. |
| 10,583,013 B2 | 3/2020 | Dimauro et al. |
| 10,583,015 B2 | 3/2020 | Olmos et al. |
| 10,624,758 B2 | 4/2020 | Slivka et al. |
| 10,639,164 B2 | 5/2020 | Dimauro et al. |
| 10,973,652 B2 | 4/2021 | Hawkins et al. |
| 11,051,954 B2 | 7/2021 | Greenhalgh et al. |
| 11,103,362 B2 | 8/2021 | Butler et al. |
| 2001/0011174 A1 | 8/2001 | Reiley et al. |
| 2001/0012950 A1 | 8/2001 | Nishtala et al. |
| 2001/0016741 A1 | 8/2001 | Burkus et al. |
| 2001/0016775 A1 | 8/2001 | Scarborough et al. |
| 2001/0027320 A1 | 10/2001 | Sasso |
| 2001/0032020 A1 | 10/2001 | Besselink |
| 2001/0037126 A1 | 11/2001 | Stack et al. |
| 2001/0039452 A1 | 11/2001 | Zucherman et al. |
| 2001/0039453 A1 | 11/2001 | Gresser et al. |
| 2001/0049529 A1 | 12/2001 | Cachia et al. |
| 2001/0049530 A1 | 12/2001 | Culbert et al. |
| 2001/0049531 A1 | 12/2001 | Reiley et al. |
| 2001/0056302 A1 | 12/2001 | Boyer et al. |
| 2002/0001476 A1 | 1/2002 | Nagamine et al. |
| 2002/0010070 A1 | 1/2002 | Cales et al. |
| 2002/0016583 A1 | 2/2002 | Cragg |
| 2002/0026195 A1 | 2/2002 | Layne et al. |
| 2002/0026244 A1 | 2/2002 | Trieu |
| 2002/0029084 A1 | 3/2002 | Paul et al. |
| 2002/0032462 A1 | 3/2002 | Houser et al. |
| 2002/0032483 A1 | 3/2002 | Nicholson et al. |
| 2002/0035400 A1 | 3/2002 | Bryan et al. |
| 2002/0037799 A1 | 3/2002 | Li et al. |
| 2002/0045904 A1 | 4/2002 | Fuss et al. |
| 2002/0045942 A1 | 4/2002 | Ham |
| 2002/0055740 A1 | 5/2002 | Lieberman |
| 2002/0055781 A1 | 5/2002 | Sazy |
| 2002/0058947 A1 | 5/2002 | Hochschuler et al. |
| 2002/0068974 A1 | 6/2002 | Kuslich et al. |
| 2002/0068976 A1 | 6/2002 | Jackson |
| 2002/0068977 A1 | 6/2002 | Jackson |
| 2002/0072801 A1 | 6/2002 | Michelson |
| 2002/0077700 A1 | 6/2002 | Varga et al. |
| 2002/0077701 A1 | 6/2002 | Kuslich |
| 2002/0082584 A1 | 6/2002 | Rosenman et al. |
| 2002/0082608 A1 | 6/2002 | Reiley et al. |
| 2002/0087152 A1 | 7/2002 | Mikus et al. |
| 2002/0087163 A1 | 7/2002 | Dixon et al. |
| 2002/0091387 A1 | 7/2002 | Hoogland |
| 2002/0091390 A1 | 7/2002 | Michelson |
| 2002/0099385 A1 | 7/2002 | Ralph et al. |
| 2002/0107519 A1 | 8/2002 | Dixon et al. |
| 2002/0107573 A1 | 8/2002 | Steinberg |
| 2002/0120335 A1 | 8/2002 | Angelucci et al. |
| 2002/0128713 A1 | 9/2002 | Ferree |
| 2002/0128715 A1 | 9/2002 | Bryan et al. |
| 2002/0128716 A1 | 9/2002 | Cohen et al. |
| 2002/0138078 A1 | 9/2002 | Chappuis |
| 2002/0138146 A1 | 9/2002 | Jackson |
| 2002/0143331 A1 | 10/2002 | Zucherman et al. |
| 2002/0143334 A1 | 10/2002 | Hoffmann et al. |
| 2002/0143335 A1 | 10/2002 | Von et al. |
| 2002/0151895 A1 | 10/2002 | Soboleski et al. |
| 2002/0151976 A1 | 10/2002 | Foley et al. |
| 2002/0156482 A1 | 10/2002 | Scribner et al. |
| 2002/0161444 A1 | 10/2002 | Choi |
| 2002/0165612 A1 | 11/2002 | Gerber et al. |
| 2002/0169471 A1 | 11/2002 | Ferdinand |
| 2002/0172851 A1 | 11/2002 | Corey et al. |
| 2002/0173796 A1 | 11/2002 | Cragg |
| 2002/0173841 A1 | 11/2002 | Ortiz et al. |
| 2002/0173851 A1 | 11/2002 | McKay |
| 2002/0183761 A1 | 12/2002 | Johnson et al. |
| 2002/0183778 A1 | 12/2002 | Reiley et al. |
| 2002/0183848 A1 | 12/2002 | Ray et al. |
| 2002/0191487 A1 | 12/2002 | Sand |
| 2002/0193883 A1 | 12/2002 | Wironen |
| 2002/0198526 A1 | 12/2002 | Shaolian et al. |
| 2003/0004575 A1 | 1/2003 | Erickson |
| 2003/0004576 A1 | 1/2003 | Thalgott |
| 2003/0006942 A1 | 1/2003 | Searls et al. |
| 2003/0014112 A1 | 1/2003 | Ralph et al. |
| 2003/0014113 A1 | 1/2003 | Ralph et al. |
| 2003/0014116 A1 | 1/2003 | Ralph et al. |
| 2003/0018390 A1 | 1/2003 | Husson |
| 2003/0023305 A1 | 1/2003 | McKay |

(56) References Cited

U.S. PATENT DOCUMENTS

| | | |
|---|---|---|
| 2003/0028250 A1 | 2/2003 | Reiley et al. |
| 2003/0028251 A1 | 2/2003 | Mathews |
| 2003/0032963 A1 | 2/2003 | Reiss et al. |
| 2003/0040796 A1 | 2/2003 | Ferree |
| 2003/0040799 A1 | 2/2003 | Boyd et al. |
| 2003/0045937 A1 | 3/2003 | Ginn |
| 2003/0045939 A1 | 3/2003 | Casutt |
| 2003/0050644 A1 | 3/2003 | Boucher et al. |
| 2003/0063582 A1 | 4/2003 | Mizell et al. |
| 2003/0065330 A1 | 4/2003 | Zucherman et al. |
| 2003/0065396 A1 | 4/2003 | Michelson |
| 2003/0069582 A1 | 4/2003 | Culbert |
| 2003/0069593 A1 | 4/2003 | Tremulis et al. |
| 2003/0069642 A1 | 4/2003 | Ralph et al. |
| 2003/0073998 A1 | 4/2003 | Pagliuca et al. |
| 2003/0074063 A1 | 4/2003 | Gerbec et al. |
| 2003/0074075 A1 | 4/2003 | Thomas et al. |
| 2003/0078667 A1 | 4/2003 | Manasas et al. |
| 2003/0083642 A1 | 5/2003 | Boyd et al. |
| 2003/0083688 A1 | 5/2003 | Simonson |
| 2003/0108588 A1 | 6/2003 | Chen et al. |
| 2003/0130664 A1 | 7/2003 | Boucher et al. |
| 2003/0130739 A1 | 7/2003 | Gerbec et al. |
| 2003/0135275 A1 | 7/2003 | Garcia et al. |
| 2003/0139648 A1 | 7/2003 | Foley et al. |
| 2003/0139812 A1 | 7/2003 | Garcia et al. |
| 2003/0139813 A1 | 7/2003 | Messerli et al. |
| 2003/0153874 A1 | 8/2003 | Tal |
| 2003/0171812 A1 | 9/2003 | Grunberg et al. |
| 2003/0187431 A1 | 10/2003 | Simonson |
| 2003/0187445 A1 | 10/2003 | Keith et al. |
| 2003/0187506 A1 | 10/2003 | Ross et al. |
| 2003/0191414 A1 | 10/2003 | Reiley et al. |
| 2003/0191489 A1 | 10/2003 | Reiley et al. |
| 2003/0191531 A1 | 10/2003 | Berry et al. |
| 2003/0195518 A1 | 10/2003 | Cragg |
| 2003/0195547 A1 | 10/2003 | Scribner et al. |
| 2003/0195630 A1 | 10/2003 | Ferree |
| 2003/0199979 A1 | 10/2003 | McGuckin |
| 2003/0204261 A1 | 10/2003 | Eisermann et al. |
| 2003/0208122 A1 | 11/2003 | Melkent et al. |
| 2003/0208136 A1 | 11/2003 | Mark et al. |
| 2003/0208203 A1 | 11/2003 | Lim et al. |
| 2003/0208220 A1 | 11/2003 | Worley et al. |
| 2003/0220643 A1 | 11/2003 | Ferree |
| 2003/0220648 A1 | 11/2003 | Osorio et al. |
| 2003/0220695 A1 | 11/2003 | Sevrain |
| 2003/0229350 A1 | 12/2003 | Kay |
| 2003/0229372 A1 | 12/2003 | Reiley et al. |
| 2003/0233096 A1 | 12/2003 | Osorio et al. |
| 2003/0233102 A1 | 12/2003 | Nakamura et al. |
| 2003/0233145 A1 | 12/2003 | Landry et al. |
| 2003/0233146 A1 | 12/2003 | Grinberg et al. |
| 2004/0002761 A1 | 1/2004 | Rogers et al. |
| 2004/0006391 A1 | 1/2004 | Reiley |
| 2004/0008949 A1 | 1/2004 | Liu et al. |
| 2004/0010251 A1 | 1/2004 | Pitaru et al. |
| 2004/0010260 A1 | 1/2004 | Scribner et al. |
| 2004/0010263 A1 | 1/2004 | Boucher et al. |
| 2004/0010318 A1 | 1/2004 | Ferree |
| 2004/0019354 A1 | 1/2004 | Johnson et al. |
| 2004/0019359 A1 | 1/2004 | Worley et al. |
| 2004/0024408 A1 | 2/2004 | Burkus et al. |
| 2004/0024409 A1 | 2/2004 | Sand et al. |
| 2004/0024410 A1 | 2/2004 | Olson et al. |
| 2004/0024463 A1 | 2/2004 | Thomas et al. |
| 2004/0024465 A1 | 2/2004 | Lambrecht et al. |
| 2004/0030387 A1 | 2/2004 | Landry et al. |
| 2004/0034343 A1 | 2/2004 | Gillespie et al. |
| 2004/0034429 A1 | 2/2004 | Lambrecht et al. |
| 2004/0049190 A1 | 3/2004 | Biedermann et al. |
| 2004/0049203 A1 | 3/2004 | Scribner et al. |
| 2004/0049223 A1 | 3/2004 | Nishtala et al. |
| 2004/0049270 A1 | 3/2004 | Gewirtz |
| 2004/0054412 A1 | 3/2004 | Gerbec et al. |
| 2004/0059333 A1 | 3/2004 | Carl et al. |
| 2004/0059337 A1 | 3/2004 | Hanson et al. |
| 2004/0059339 A1 | 3/2004 | Roehm et al. |
| 2004/0059350 A1 | 3/2004 | Gordon et al. |
| 2004/0059418 A1 | 3/2004 | McKay et al. |
| 2004/0064144 A1 | 4/2004 | Johnson et al. |
| 2004/0068269 A1 | 4/2004 | Bonati et al. |
| 2004/0073213 A1 | 4/2004 | Serhan et al. |
| 2004/0073308 A1 | 4/2004 | Kuslich et al. |
| 2004/0073310 A1 | 4/2004 | Moumene et al. |
| 2004/0082953 A1 | 4/2004 | Petit |
| 2004/0083000 A1 | 4/2004 | Keller et al. |
| 2004/0087947 A1* | 5/2004 | Lim ............... A61F 2/4465 606/279 |
| 2004/0088055 A1 | 5/2004 | Hanson et al. |
| 2004/0092933 A1 | 5/2004 | Shaolian et al. |
| 2004/0092948 A1 | 5/2004 | Stevens et al. |
| 2004/0092988 A1 | 5/2004 | Shaolian et al. |
| 2004/0093083 A1 | 5/2004 | Branch et al. |
| 2004/0097924 A1 | 5/2004 | Lambrecht et al. |
| 2004/0097930 A1 | 5/2004 | Justis et al. |
| 2004/0097932 A1 | 5/2004 | Ray et al. |
| 2004/0097941 A1 | 5/2004 | Weiner et al. |
| 2004/0097973 A1 | 5/2004 | Loshakove et al. |
| 2004/0098131 A1 | 5/2004 | Bryan et al. |
| 2004/0102774 A1 | 5/2004 | Trieu |
| 2004/0102784 A1 | 5/2004 | Pasquet et al. |
| 2004/0102846 A1 | 5/2004 | Keller et al. |
| 2004/0106925 A1 | 6/2004 | Culbert |
| 2004/0106940 A1 | 6/2004 | Shaolian et al. |
| 2004/0111161 A1 | 6/2004 | Trieu |
| 2004/0116997 A1 | 6/2004 | Taylor et al. |
| 2004/0117019 A1 | 6/2004 | Trieu et al. |
| 2004/0117022 A1 | 6/2004 | Marnay et al. |
| 2004/0127906 A1 | 7/2004 | Culbert et al. |
| 2004/0127990 A1 | 7/2004 | Bartish et al. |
| 2004/0127991 A1 | 7/2004 | Ferree |
| 2004/0133124 A1 | 7/2004 | Bates et al. |
| 2004/0133229 A1 | 7/2004 | Lambrecht et al. |
| 2004/0133279 A1 | 7/2004 | Krueger et al. |
| 2004/0133280 A1 | 7/2004 | Trieu |
| 2004/0138748 A1 | 7/2004 | Boyer et al. |
| 2004/0143284 A1 | 7/2004 | Chin |
| 2004/0143332 A1 | 7/2004 | Krueger et al. |
| 2004/0143734 A1 | 7/2004 | Buer et al. |
| 2004/0147129 A1 | 7/2004 | Rolfson |
| 2004/0147877 A1 | 7/2004 | Heuser |
| 2004/0147950 A1 | 7/2004 | Mueller et al. |
| 2004/0148027 A1 | 7/2004 | Errico et al. |
| 2004/0153064 A1 | 8/2004 | Foley et al. |
| 2004/0153065 A1 | 8/2004 | Lim |
| 2004/0153115 A1 | 8/2004 | Reiley et al. |
| 2004/0153156 A1 | 8/2004 | Cohen et al. |
| 2004/0153160 A1 | 8/2004 | Carrasco |
| 2004/0158206 A1 | 8/2004 | Aboul-Hosn et al. |
| 2004/0158258 A1 | 8/2004 | Bonati et al. |
| 2004/0162617 A1 | 8/2004 | Zucherman et al. |
| 2004/0162618 A1 | 8/2004 | Mujwid et al. |
| 2004/0167561 A1 | 8/2004 | Boucher et al. |
| 2004/0167562 A1 | 8/2004 | Osorio et al. |
| 2004/0167625 A1 | 8/2004 | Beyar et al. |
| 2004/0172133 A1 | 9/2004 | Gerber et al. |
| 2004/0172134 A1 | 9/2004 | Berry |
| 2004/0176775 A1 | 9/2004 | Burkus et al. |
| 2004/0186052 A1 | 9/2004 | Iyer et al. |
| 2004/0186471 A1 | 9/2004 | Trieu |
| 2004/0186482 A1 | 9/2004 | Kolb et al. |
| 2004/0186528 A1 | 9/2004 | Ries et al. |
| 2004/0186570 A1 | 9/2004 | Rapp |
| 2004/0186573 A1 | 9/2004 | Ferree |
| 2004/0186577 A1 | 9/2004 | Ferree |
| 2004/0193271 A1 | 9/2004 | Fraser et al. |
| 2004/0193277 A1 | 9/2004 | Long et al. |
| 2004/0199162 A1 | 10/2004 | Von et al. |
| 2004/0210231 A1 | 10/2004 | Boucher et al. |
| 2004/0210310 A1 | 10/2004 | Trieu |
| 2004/0215343 A1 | 10/2004 | Hochschuler et al. |
| 2004/0215344 A1 | 10/2004 | Hochschuler et al. |
| 2004/0220580 A1 | 11/2004 | Johnson et al. |

(56) References Cited

U.S. PATENT DOCUMENTS

| | | |
|---|---|---|
| 2004/0220668 A1 | 11/2004 | Eisermann et al. |
| 2004/0220669 A1 | 11/2004 | Studer |
| 2004/0220672 A1 | 11/2004 | Shadduck |
| 2004/0225292 A1 | 11/2004 | Sasso et al. |
| 2004/0225296 A1 | 11/2004 | Reiss et al. |
| 2004/0225361 A1 | 11/2004 | Glenn et al. |
| 2004/0230191 A1 | 11/2004 | Frey et al. |
| 2004/0230309 A1 | 11/2004 | Dimauro et al. |
| 2004/0243229 A1 | 12/2004 | Vidlund et al. |
| 2004/0243239 A1 | 12/2004 | Taylor |
| 2004/0243241 A1 | 12/2004 | Istephanous et al. |
| 2004/0249377 A1 | 12/2004 | Kaes et al. |
| 2004/0249461 A1 | 12/2004 | Ferree |
| 2004/0249466 A1 | 12/2004 | Liu et al. |
| 2004/0254520 A1 | 12/2004 | Porteous et al. |
| 2004/0254575 A1 | 12/2004 | Obenchain et al. |
| 2004/0254643 A1 | 12/2004 | Jackson |
| 2004/0254644 A1 | 12/2004 | Taylor |
| 2004/0260297 A1 | 12/2004 | Padget et al. |
| 2004/0260300 A1 | 12/2004 | Gorensek et al. |
| 2004/0260397 A1 | 12/2004 | Lambrecht et al. |
| 2004/0266257 A1 | 12/2004 | Ries et al. |
| 2004/0267271 A9 | 12/2004 | Scribner et al. |
| 2004/0267367 A1 | 12/2004 | O'Neil |
| 2005/0004578 A1 | 1/2005 | Lambrecht et al. |
| 2005/0010292 A1 | 1/2005 | Carrasco |
| 2005/0010293 A1 | 1/2005 | Zucherman et al. |
| 2005/0010298 A1 | 1/2005 | Zucherman et al. |
| 2005/0015147 A1 | 1/2005 | Schwardt et al. |
| 2005/0015148 A1 | 1/2005 | Jansen et al. |
| 2005/0015152 A1 | 1/2005 | Sweeney |
| 2005/0019365 A1 | 1/2005 | Frauchiger et al. |
| 2005/0021041 A1 | 1/2005 | Michelson |
| 2005/0027360 A1 | 2/2005 | Webb et al. |
| 2005/0033289 A1 | 2/2005 | Warren et al. |
| 2005/0033295 A1 | 2/2005 | Wisnewski |
| 2005/0033434 A1 | 2/2005 | Berry |
| 2005/0033440 A1 | 2/2005 | Lambrecht et al. |
| 2005/0038431 A1 | 2/2005 | Bartish et al. |
| 2005/0038515 A1 | 2/2005 | Kunzler |
| 2005/0038517 A1 | 2/2005 | Carrison et al. |
| 2005/0043737 A1 | 2/2005 | Reiley et al. |
| 2005/0043796 A1 | 2/2005 | Grant et al. |
| 2005/0043800 A1 | 2/2005 | Paul et al. |
| 2005/0054948 A1 | 3/2005 | Goldenberg |
| 2005/0055097 A1 | 3/2005 | Grunberg et al. |
| 2005/0060036 A1 | 3/2005 | Schultz et al. |
| 2005/0060038 A1 | 3/2005 | Lambrecht et al. |
| 2005/0065519 A1 | 3/2005 | Michelson |
| 2005/0065609 A1 | 3/2005 | Wardlaw |
| 2005/0065610 A1 | 3/2005 | Pisharodi |
| 2005/0069571 A1 | 3/2005 | Slivka et al. |
| 2005/0070908 A1 | 3/2005 | Cragg |
| 2005/0070911 A1 | 3/2005 | Carrison et al. |
| 2005/0070913 A1 | 3/2005 | Milbocker et al. |
| 2005/0071011 A1 | 3/2005 | Ralph et al. |
| 2005/0080443 A1 | 4/2005 | Fallin et al. |
| 2005/0080488 A1 | 4/2005 | Schultz |
| 2005/0085912 A1 | 4/2005 | Arnin et al. |
| 2005/0090443 A1 | 4/2005 | Michael John |
| 2005/0090833 A1 | 4/2005 | DiPoto |
| 2005/0090852 A1 | 4/2005 | Layne et al. |
| 2005/0090899 A1 | 4/2005 | DiPoto |
| 2005/0096745 A1 | 5/2005 | Andre et al. |
| 2005/0102202 A1 | 5/2005 | Linden et al. |
| 2005/0107880 A1 | 5/2005 | Shimp et al. |
| 2005/0113916 A1 | 5/2005 | Branch, Jr. |
| 2005/0113917 A1 | 5/2005 | Chae et al. |
| 2005/0113918 A1 | 5/2005 | Messerli et al. |
| 2005/0113919 A1 | 5/2005 | Cragg et al. |
| 2005/0113927 A1 | 5/2005 | Malek |
| 2005/0113928 A1 | 5/2005 | Cragg et al. |
| 2005/0118228 A1 | 6/2005 | Trieu |
| 2005/0118550 A1 | 6/2005 | Turri |
| 2005/0119657 A1 | 6/2005 | Goldsmith |
| 2005/0119662 A1 | 6/2005 | Reiley et al. |
| 2005/0119750 A1 | 6/2005 | Studer |
| 2005/0119751 A1 | 6/2005 | Lawson |
| 2005/0119752 A1 | 6/2005 | Williams et al. |
| 2005/0119754 A1 | 6/2005 | Trieu et al. |
| 2005/0124989 A1 | 6/2005 | Suddaby |
| 2005/0124992 A1 | 6/2005 | Ferree |
| 2005/0124999 A1 | 6/2005 | Teitelbaum et al. |
| 2005/0125061 A1* | 6/2005 | Zucherman ............ A61F 2/4425 623/17.11 |
| 2005/0125062 A1 | 6/2005 | Biedermann et al. |
| 2005/0125066 A1 | 6/2005 | McAfee |
| 2005/0130929 A1 | 6/2005 | Boyd |
| 2005/0131267 A1 | 6/2005 | Talmadge |
| 2005/0131268 A1 | 6/2005 | Talmadge |
| 2005/0131269 A1 | 6/2005 | Talmadge |
| 2005/0131406 A1 | 6/2005 | Reiley et al. |
| 2005/0131409 A1 | 6/2005 | Chervitz et al. |
| 2005/0131411 A1 | 6/2005 | Culbert |
| 2005/0131536 A1 | 6/2005 | Eisermann et al. |
| 2005/0131538 A1 | 6/2005 | Chervitz et al. |
| 2005/0131540 A1 | 6/2005 | Trieu |
| 2005/0131541 A1 | 6/2005 | Trieu |
| 2005/0137595 A1 | 6/2005 | Hoffmann et al. |
| 2005/0137602 A1 | 6/2005 | Assell et al. |
| 2005/0142211 A1 | 6/2005 | Wenz |
| 2005/0143734 A1 | 6/2005 | Cachia et al. |
| 2005/0143763 A1 | 6/2005 | Ortiz et al. |
| 2005/0143827 A1 | 6/2005 | Globerman et al. |
| 2005/0149022 A1 | 7/2005 | Shaolian et al. |
| 2005/0149030 A1 | 7/2005 | Serhan et al. |
| 2005/0149034 A1 | 7/2005 | Assell et al. |
| 2005/0149191 A1 | 7/2005 | Cragg et al. |
| 2005/0149194 A1 | 7/2005 | Ahlgren |
| 2005/0149197 A1 | 7/2005 | Cauthen |
| 2005/0154396 A1 | 7/2005 | Foley et al. |
| 2005/0154463 A1 | 7/2005 | Trieu |
| 2005/0154467 A1 | 7/2005 | Peterman et al. |
| 2005/0159819 A1 | 7/2005 | McCormack et al. |
| 2005/0165398 A1 | 7/2005 | Reiley |
| 2005/0165406 A1 | 7/2005 | Assell et al. |
| 2005/0165420 A1 | 7/2005 | Cha |
| 2005/0165483 A1 | 7/2005 | Ray et al. |
| 2005/0165484 A1 | 7/2005 | Ferree |
| 2005/0165485 A1 | 7/2005 | Trieu |
| 2005/0171539 A1 | 8/2005 | Braun et al. |
| 2005/0171541 A1 | 8/2005 | Boehm et al. |
| 2005/0171552 A1 | 8/2005 | Johnson et al. |
| 2005/0171608 A1 | 8/2005 | Peterman et al. |
| 2005/0171610 A1 | 8/2005 | Humphreys et al. |
| 2005/0177173 A1 | 8/2005 | Aebi et al. |
| 2005/0177235 A1 | 8/2005 | Baynham et al. |
| 2005/0177240 A1 | 8/2005 | Blain |
| 2005/0182412 A1 | 8/2005 | Johnson et al. |
| 2005/0182413 A1 | 8/2005 | Johnson et al. |
| 2005/0182414 A1 | 8/2005 | Manzi et al. |
| 2005/0182418 A1 | 8/2005 | Boyd et al. |
| 2005/0187556 A1 | 8/2005 | Stack et al. |
| 2005/0187558 A1 | 8/2005 | Johnson et al. |
| 2005/0187559 A1 | 8/2005 | Raymond et al. |
| 2005/0187564 A1 | 8/2005 | Jayaraman |
| 2005/0197702 A1 | 9/2005 | Coppes et al. |
| 2005/0197707 A1 | 9/2005 | Trieu et al. |
| 2005/0203512 A1 | 9/2005 | Hawkins et al. |
| 2005/0216018 A1 | 9/2005 | Sennett |
| 2005/0216026 A1 | 9/2005 | Culbert |
| 2005/0216081 A1 | 9/2005 | Taylor |
| 2005/0216087 A1 | 9/2005 | Zucherman et al. |
| 2005/0222681 A1 | 10/2005 | Richley et al. |
| 2005/0222684 A1 | 10/2005 | Ferree |
| 2005/0228383 A1 | 10/2005 | Zucherman et al. |
| 2005/0228391 A1 | 10/2005 | Levy et al. |
| 2005/0228397 A1 | 10/2005 | Malandain et al. |
| 2005/0234425 A1 | 10/2005 | Miller et al. |
| 2005/0234451 A1 | 10/2005 | Markworth |
| 2005/0234452 A1 | 10/2005 | Malandain |
| 2005/0234456 A1 | 10/2005 | Malandain |
| 2005/0240182 A1 | 10/2005 | Zucherman et al. |
| 2005/0240189 A1 | 10/2005 | Rousseau et al. |

(56) References Cited

U.S. PATENT DOCUMENTS

| | | |
|---|---|---|
| 2005/0240193 A1 | 10/2005 | Layne et al. |
| 2005/0240269 A1 | 10/2005 | Lambrecht et al. |
| 2005/0251142 A1 | 11/2005 | Hoffmann et al. |
| 2005/0251149 A1 | 11/2005 | Wenz |
| 2005/0251260 A1 | 11/2005 | Gerber et al. |
| 2005/0256525 A1 | 11/2005 | Culbert et al. |
| 2005/0256576 A1 | 11/2005 | Moskowitz et al. |
| 2005/0261682 A1 | 11/2005 | Ferree |
| 2005/0261684 A1 | 11/2005 | Shaolian et al. |
| 2005/0261695 A1 | 11/2005 | Cragg et al. |
| 2005/0261769 A1 | 11/2005 | Moskowitz et al. |
| 2005/0261781 A1 | 11/2005 | Sennett et al. |
| 2005/0267471 A1 | 12/2005 | Biedermann et al. |
| 2005/0273166 A1 | 12/2005 | Sweeney |
| 2005/0273173 A1 | 12/2005 | Gordon et al. |
| 2005/0277938 A1 | 12/2005 | Parsons |
| 2005/0278023 A1 | 12/2005 | Zwirkoski |
| 2005/0278026 A1 | 12/2005 | Gordon et al. |
| 2005/0278027 A1 | 12/2005 | Hyde, Jr. |
| 2005/0278029 A1 | 12/2005 | Trieu |
| 2005/0283238 A1 | 12/2005 | Reiley |
| 2005/0283244 A1 | 12/2005 | Gordon et al. |
| 2005/0287071 A1 | 12/2005 | Wenz |
| 2006/0004326 A1 | 1/2006 | Collins et al. |
| 2006/0004456 A1 | 1/2006 | McKay |
| 2006/0004457 A1 | 1/2006 | Collins et al. |
| 2006/0004458 A1 | 1/2006 | Collins et al. |
| 2006/0009778 A1 | 1/2006 | Collins et al. |
| 2006/0009779 A1 | 1/2006 | Collins et al. |
| 2006/0009851 A1 | 1/2006 | Collins et al. |
| 2006/0015105 A1 | 1/2006 | Warren et al. |
| 2006/0015119 A1 | 1/2006 | Plassky et al. |
| 2006/0020284 A1 | 1/2006 | Foley et al. |
| 2006/0022180 A1 | 2/2006 | Selness |
| 2006/0030850 A1 | 2/2006 | Keegan et al. |
| 2006/0030872 A1 | 2/2006 | Culbert et al. |
| 2006/0030933 A1 | 2/2006 | Delegge et al. |
| 2006/0030943 A1 | 2/2006 | Peterman |
| 2006/0032621 A1 | 2/2006 | Martin et al. |
| 2006/0036241 A1 | 2/2006 | Siegal |
| 2006/0036244 A1 | 2/2006 | Spitler et al. |
| 2006/0036246 A1 | 2/2006 | Carl et al. |
| 2006/0036256 A1 | 2/2006 | Carl et al. |
| 2006/0036259 A1 | 2/2006 | Carl et al. |
| 2006/0036261 A1 | 2/2006 | McDonnell |
| 2006/0036273 A1 | 2/2006 | Siegal |
| 2006/0036323 A1 | 2/2006 | Carl et al. |
| 2006/0036324 A1 | 2/2006 | Sachs et al. |
| 2006/0041258 A1 | 2/2006 | Galea |
| 2006/0041314 A1 | 2/2006 | Millard |
| 2006/0045904 A1 | 3/2006 | Aronson |
| 2006/0058790 A1 | 3/2006 | Carl et al. |
| 2006/0058807 A1 | 3/2006 | Landry et al. |
| 2006/0058876 A1 | 3/2006 | McKinley |
| 2006/0058880 A1 | 3/2006 | Wysocki et al. |
| 2006/0064101 A1 | 3/2006 | Arramon |
| 2006/0064102 A1 | 3/2006 | Ebner |
| 2006/0064171 A1 | 3/2006 | Trieu |
| 2006/0064172 A1 | 3/2006 | Trieu |
| 2006/0069436 A1 | 3/2006 | Sutton et al. |
| 2006/0069439 A1 | 3/2006 | Zucherman et al. |
| 2006/0069440 A1 | 3/2006 | Zucherman et al. |
| 2006/0074429 A1 | 4/2006 | Ralph et al. |
| 2006/0079908 A1 | 4/2006 | Lieberman |
| 2006/0084867 A1 | 4/2006 | Tremblay et al. |
| 2006/0084977 A1 | 4/2006 | Lieberman |
| 2006/0084988 A1 | 4/2006 | Kim |
| 2006/0085002 A1 | 4/2006 | Trieu et al. |
| 2006/0085009 A1 | 4/2006 | Truckai et al. |
| 2006/0085010 A1 | 4/2006 | Lieberman |
| 2006/0089642 A1 | 4/2006 | Diaz et al. |
| 2006/0089646 A1 | 4/2006 | Bonutti |
| 2006/0089654 A1 | 4/2006 | Lins et al. |
| 2006/0089715 A1 | 4/2006 | Truckai et al. |
| 2006/0089718 A1 | 4/2006 | Zucherman et al. |
| 2006/0089719 A1 | 4/2006 | Trieu |
| 2006/0095045 A1 | 5/2006 | Trieu |
| 2006/0095046 A1 | 5/2006 | Trieu et al. |
| 2006/0095134 A1 | 5/2006 | Trieu et al. |
| 2006/0095138 A1 | 5/2006 | Truckai et al. |
| 2006/0100622 A1 | 5/2006 | Jackson |
| 2006/0100706 A1 | 5/2006 | Shadduck et al. |
| 2006/0100707 A1 | 5/2006 | Stinson et al. |
| 2006/0106381 A1 | 5/2006 | Ferree et al. |
| 2006/0106397 A1 | 5/2006 | Lins |
| 2006/0106459 A1 | 5/2006 | Truckai et al. |
| 2006/0111715 A1 | 5/2006 | Jackson |
| 2006/0111728 A1 | 5/2006 | Abdou |
| 2006/0111785 A1 | 5/2006 | O'Neil |
| 2006/0119629 A1 | 6/2006 | An et al. |
| 2006/0122609 A1 | 6/2006 | Mirkovic et al. |
| 2006/0122610 A1 | 6/2006 | Culbert et al. |
| 2006/0122701 A1 | 6/2006 | Kiester |
| 2006/0122703 A1 | 6/2006 | Aebi et al. |
| 2006/0122704 A1 | 6/2006 | Vresilovic et al. |
| 2006/0129244 A1 | 6/2006 | Ensign |
| 2006/0136062 A1 | 6/2006 | Dinello et al. |
| 2006/0136064 A1 | 6/2006 | Sherman |
| 2006/0142759 A1 | 6/2006 | Arnin et al. |
| 2006/0142765 A9 | 6/2006 | Dixon et al. |
| 2006/0142776 A1 | 6/2006 | Iwanari |
| 2006/0142858 A1 | 6/2006 | Colleran et al. |
| 2006/0142864 A1 | 6/2006 | Cauthen |
| 2006/0149136 A1 | 7/2006 | Seto et al. |
| 2006/0149229 A1 | 7/2006 | Kwak et al. |
| 2006/0149237 A1 | 7/2006 | Markworth et al. |
| 2006/0149252 A1 | 7/2006 | Markworth et al. |
| 2006/0149379 A1 | 7/2006 | Kuslich et al. |
| 2006/0149380 A1 | 7/2006 | Lotz et al. |
| 2006/0149385 A1 | 7/2006 | McKay |
| 2006/0155379 A1 | 7/2006 | Heneveld et al. |
| 2006/0161162 A1 | 7/2006 | Lambrecht et al. |
| 2006/0161166 A1 | 7/2006 | Johnson et al. |
| 2006/0167547 A1 | 7/2006 | Suddaby |
| 2006/0167553 A1 | 7/2006 | Cauthen et al. |
| 2006/0173545 A1 | 8/2006 | Cauthen et al. |
| 2006/0178743 A1 | 8/2006 | Carter |
| 2006/0178745 A1 | 8/2006 | Bartish et al. |
| 2006/0178746 A1 | 8/2006 | Bartish et al. |
| 2006/0184192 A1 | 8/2006 | Markworth et al. |
| 2006/0184247 A1 | 8/2006 | Edidin et al. |
| 2006/0184248 A1 | 8/2006 | Edidin et al. |
| 2006/0189999 A1 | 8/2006 | Zwirkoski |
| 2006/0190083 A1 | 8/2006 | Arnin et al. |
| 2006/0190085 A1 | 8/2006 | Cauthen |
| 2006/0195102 A1 | 8/2006 | Malandain |
| 2006/0195103 A1 | 8/2006 | Padget et al. |
| 2006/0195191 A1 | 8/2006 | Sweeney et al. |
| 2006/0200139 A1 | 9/2006 | Michelson |
| 2006/0200164 A1 | 9/2006 | Michelson |
| 2006/0200239 A1 | 9/2006 | Rothman et al. |
| 2006/0200240 A1 | 9/2006 | Rothman et al. |
| 2006/0200241 A1 | 9/2006 | Rothman et al. |
| 2006/0200242 A1 | 9/2006 | Rothman et al. |
| 2006/0200243 A1 | 9/2006 | Rothman et al. |
| 2006/0206116 A1 | 9/2006 | Yeung |
| 2006/0206207 A1 | 9/2006 | Dryer et al. |
| 2006/0212118 A1 | 9/2006 | Abernathie |
| 2006/0217711 A1 | 9/2006 | Stevens et al. |
| 2006/0229627 A1 | 10/2006 | Hunt et al. |
| 2006/0229629 A1 | 10/2006 | Manzi et al. |
| 2006/0229724 A1 | 10/2006 | Lechmann et al. |
| 2006/0235403 A1 | 10/2006 | Blain |
| 2006/0235412 A1 | 10/2006 | Blain |
| 2006/0235423 A1 | 10/2006 | Cantu |
| 2006/0235521 A1 | 10/2006 | Zucherman et al. |
| 2006/0235531 A1 | 10/2006 | Buettner-Janz |
| 2006/0241643 A1 | 10/2006 | Lim et al. |
| 2006/0241663 A1 | 10/2006 | Rice et al. |
| 2006/0241770 A1 | 10/2006 | Rhoda et al. |
| 2006/0247634 A1 | 11/2006 | Warner et al. |
| 2006/0247770 A1 | 11/2006 | Peterman |
| 2006/0247771 A1 | 11/2006 | Peterman et al. |
| 2006/0247781 A1 | 11/2006 | Francis |

(56) References Cited

U.S. PATENT DOCUMENTS

| | | |
|---|---|---|
| 2006/0253120 A1 | 11/2006 | Anderson et al. |
| 2006/0253201 A1 | 11/2006 | McLuen |
| 2006/0254784 A1 | 11/2006 | Hartmann et al. |
| 2006/0264896 A1 | 11/2006 | Palmer |
| 2006/0264939 A1 | 11/2006 | Zucherman et al. |
| 2006/0264945 A1 | 11/2006 | Edidin et al. |
| 2006/0265067 A1 | 11/2006 | Zucherman et al. |
| 2006/0265075 A1 | 11/2006 | Baumgartner et al. |
| 2006/0265077 A1 | 11/2006 | Zwirkoski |
| 2006/0271049 A1 | 11/2006 | Zucherman et al. |
| 2006/0271061 A1 | 11/2006 | Beyar et al. |
| 2006/0276897 A1 | 12/2006 | Winslow et al. |
| 2006/0276899 A1 | 12/2006 | Zipnick et al. |
| 2006/0276901 A1 | 12/2006 | Zipnick et al. |
| 2006/0276902 A1 | 12/2006 | Zipnick et al. |
| 2006/0282167 A1 | 12/2006 | Lambrecht et al. |
| 2006/0287726 A1 | 12/2006 | Segal et al. |
| 2006/0287727 A1 | 12/2006 | Segal et al. |
| 2006/0293662 A1 | 12/2006 | Boyer et al. |
| 2006/0293663 A1 | 12/2006 | Walkenhorst et al. |
| 2006/0293753 A1 | 12/2006 | Thramann |
| 2007/0006692 A1 | 1/2007 | Phan |
| 2007/0010716 A1 | 1/2007 | Malandain et al. |
| 2007/0010717 A1 | 1/2007 | Cragg |
| 2007/0010824 A1 | 1/2007 | Malandain et al. |
| 2007/0010826 A1 | 1/2007 | Rhoda et al. |
| 2007/0010844 A1 | 1/2007 | Gong et al. |
| 2007/0010845 A1 | 1/2007 | Gong et al. |
| 2007/0010846 A1 | 1/2007 | Leung et al. |
| 2007/0010848 A1 | 1/2007 | Leung et al. |
| 2007/0010886 A1 | 1/2007 | Banick et al. |
| 2007/0010889 A1 | 1/2007 | Francis |
| 2007/0016191 A1 | 1/2007 | Culbert et al. |
| 2007/0032703 A1 | 2/2007 | Sankaran et al. |
| 2007/0032790 A1 | 2/2007 | Aschmann et al. |
| 2007/0032791 A1 | 2/2007 | Greenhalgh |
| 2007/0043361 A1 | 2/2007 | Malandain et al. |
| 2007/0043362 A1 | 2/2007 | Malandain et al. |
| 2007/0043363 A1 | 2/2007 | Malandain et al. |
| 2007/0043440 A1 | 2/2007 | William et al. |
| 2007/0048382 A1 | 3/2007 | Meyer et al. |
| 2007/0049849 A1 | 3/2007 | Schwardt et al. |
| 2007/0049934 A1 | 3/2007 | Edidin et al. |
| 2007/0049935 A1 | 3/2007 | Edidin et al. |
| 2007/0050034 A1 | 3/2007 | Schwardt et al. |
| 2007/0050035 A1 | 3/2007 | Schwardt et al. |
| 2007/0055201 A1 | 3/2007 | Seto et al. |
| 2007/0055236 A1 | 3/2007 | Hudgins et al. |
| 2007/0055237 A1 | 3/2007 | Edidin et al. |
| 2007/0055246 A1 | 3/2007 | Zucherman et al. |
| 2007/0055264 A1 | 3/2007 | Parmigiani |
| 2007/0055265 A1 | 3/2007 | Schaller |
| 2007/0055266 A1 | 3/2007 | Osorio et al. |
| 2007/0055267 A1 | 3/2007 | Osorio et al. |
| 2007/0055271 A1 | 3/2007 | Schaller |
| 2007/0055272 A1 | 3/2007 | Schaller |
| 2007/0055273 A1 | 3/2007 | Schaller |
| 2007/0055274 A1 | 3/2007 | Appenzeller et al. |
| 2007/0055275 A1 | 3/2007 | Schaller |
| 2007/0055276 A1 | 3/2007 | Edidin |
| 2007/0055277 A1 | 3/2007 | Osorio et al. |
| 2007/0055278 A1 | 3/2007 | Osorio et al. |
| 2007/0055281 A1 | 3/2007 | Osorio et al. |
| 2007/0055284 A1 | 3/2007 | Osorio et al. |
| 2007/0055300 A1 | 3/2007 | Osorio et al. |
| 2007/0055377 A1 | 3/2007 | Hanson et al. |
| 2007/0060933 A1 | 3/2007 | Sankaran et al. |
| 2007/0060935 A1 | 3/2007 | Schwardt et al. |
| 2007/0067034 A1 | 3/2007 | Chirico et al. |
| 2007/0067035 A1 | 3/2007 | Falahee |
| 2007/0068329 A1 | 3/2007 | Phan et al. |
| 2007/0073292 A1 | 3/2007 | Kohm et al. |
| 2007/0073399 A1 | 3/2007 | Zipnick et al. |
| 2007/0078436 A1 | 4/2007 | Leung et al. |
| 2007/0078463 A1 | 4/2007 | Malandain |
| 2007/0093689 A1 | 4/2007 | Steinberg |
| 2007/0093897 A1 | 4/2007 | Gerbec et al. |
| 2007/0093899 A1 | 4/2007 | Dutoit et al. |
| 2007/0093901 A1 | 4/2007 | Grotz et al. |
| 2007/0093906 A1 | 4/2007 | Hudgins et al. |
| 2007/0118132 A1 | 5/2007 | Culbert et al. |
| 2007/0118222 A1 | 5/2007 | Lang |
| 2007/0118223 A1 | 5/2007 | Allard et al. |
| 2007/0123868 A1 | 5/2007 | Culbert et al. |
| 2007/0123891 A1 | 5/2007 | Ries et al. |
| 2007/0123892 A1 | 5/2007 | Ries et al. |
| 2007/0123986 A1 | 5/2007 | Schaller |
| 2007/0129730 A1 | 6/2007 | Woods et al. |
| 2007/0135922 A1 | 6/2007 | Trieu |
| 2007/0142843 A1 | 6/2007 | Dye |
| 2007/0149978 A1 | 6/2007 | Shezifi et al. |
| 2007/0150059 A1 | 6/2007 | Ruberte et al. |
| 2007/0150060 A1 | 6/2007 | Trieu |
| 2007/0150061 A1 | 6/2007 | Trieu |
| 2007/0150063 A1 | 6/2007 | Ruberte et al. |
| 2007/0150064 A1 | 6/2007 | Ruberte et al. |
| 2007/0161992 A1 | 7/2007 | Kwak et al. |
| 2007/0162005 A1 | 7/2007 | Peterson et al. |
| 2007/0162127 A1 | 7/2007 | Peterman et al. |
| 2007/0162132 A1 | 7/2007 | Messerli |
| 2007/0162138 A1 | 7/2007 | Heinz |
| 2007/0167945 A1 | 7/2007 | Lange et al. |
| 2007/0168036 A1 | 7/2007 | Ainsworth et al. |
| 2007/0168038 A1 | 7/2007 | Trieu |
| 2007/0173939 A1 | 7/2007 | Kim et al. |
| 2007/0173940 A1 | 7/2007 | Hestad et al. |
| 2007/0178222 A1 | 8/2007 | Storey et al. |
| 2007/0179612 A1 | 8/2007 | Johnson et al. |
| 2007/0179615 A1 | 8/2007 | Heinz et al. |
| 2007/0179616 A1 | 8/2007 | Braddock et al. |
| 2007/0179618 A1 | 8/2007 | Trieu et al. |
| 2007/0185578 A1 | 8/2007 | O'Neil et al. |
| 2007/0191953 A1 | 8/2007 | Trieu |
| 2007/0191954 A1 | 8/2007 | Hansell et al. |
| 2007/0191959 A1 | 8/2007 | Hartmann et al. |
| 2007/0197935 A1 | 8/2007 | Reiley et al. |
| 2007/0198023 A1 | 8/2007 | Sand et al. |
| 2007/0198025 A1 | 8/2007 | Trieu et al. |
| 2007/0198089 A1 | 8/2007 | Moskowitz et al. |
| 2007/0203491 A1 | 8/2007 | Pasquet et al. |
| 2007/0208423 A1 | 9/2007 | Messerli et al. |
| 2007/0208426 A1 | 9/2007 | Trieu |
| 2007/0213717 A1 | 9/2007 | Trieu et al. |
| 2007/0213737 A1 | 9/2007 | Schermerhorn et al. |
| 2007/0213826 A1 | 9/2007 | Smith et al. |
| 2007/0219634 A1 | 9/2007 | Greenhalgh et al. |
| 2007/0225706 A1 | 9/2007 | Clark et al. |
| 2007/0225726 A1 | 9/2007 | Dye et al. |
| 2007/0225807 A1 | 9/2007 | Phan et al. |
| 2007/0225815 A1 | 9/2007 | Keith et al. |
| 2007/0233074 A1 | 10/2007 | Anderson et al. |
| 2007/0233076 A1 | 10/2007 | Trieu |
| 2007/0233083 A1 | 10/2007 | Abdou |
| 2007/0233089 A1 | 10/2007 | Dipoto et al. |
| 2007/0233130 A1 | 10/2007 | Suddaby |
| 2007/0233244 A1 | 10/2007 | Lopez et al. |
| 2007/0233254 A1 | 10/2007 | Grotz et al. |
| 2007/0250167 A1 | 10/2007 | Bray et al. |
| 2007/0260245 A1 | 11/2007 | Malandain et al. |
| 2007/0260255 A1 | 11/2007 | Haddock et al. |
| 2007/0260314 A1 | 11/2007 | Biyani |
| 2007/0270823 A1 | 11/2007 | Trieu et al. |
| 2007/0270954 A1 | 11/2007 | Wu |
| 2007/0270957 A1 | 11/2007 | Heinz |
| 2007/0270968 A1 | 11/2007 | Baynham et al. |
| 2007/0276373 A1 | 11/2007 | Malandain |
| 2007/0276375 A1 | 11/2007 | Rapp |
| 2007/0276497 A1 | 11/2007 | Anderson |
| 2007/0282443 A1 | 12/2007 | Globerman et al. |
| 2007/0282449 A1 | 12/2007 | De et al. |
| 2007/0288091 A1 | 12/2007 | Braddock et al. |
| 2007/0299521 A1 | 12/2007 | Glenn et al. |
| 2008/0009877 A1 | 1/2008 | Sankaran et al. |
| 2008/0015694 A1 | 1/2008 | Tribus |

(56) References Cited

U.S. PATENT DOCUMENTS

| | | |
|---|---|---|
| 2008/0015701 A1 | 1/2008 | Garcia et al. |
| 2008/0021556 A1 | 1/2008 | Edie |
| 2008/0021557 A1 | 1/2008 | Trieu |
| 2008/0021558 A1 | 1/2008 | Thramann |
| 2008/0021559 A1 | 1/2008 | Thramann |
| 2008/0027437 A1 | 1/2008 | Johnson et al. |
| 2008/0027438 A1 | 1/2008 | Abdou |
| 2008/0027453 A1 | 1/2008 | Johnson et al. |
| 2008/0027454 A1 | 1/2008 | Johnson et al. |
| 2008/0027544 A1 | 1/2008 | Melkent |
| 2008/0027550 A1 | 1/2008 | Link et al. |
| 2008/0033440 A1 | 2/2008 | Moskowitz et al. |
| 2008/0045966 A1 | 2/2008 | Buttermann et al. |
| 2008/0051890 A1 | 2/2008 | Waugh et al. |
| 2008/0051897 A1 | 2/2008 | Lopez et al. |
| 2008/0051902 A1 | 2/2008 | Dwyer |
| 2008/0058598 A1 | 3/2008 | Ries et al. |
| 2008/0058937 A1 | 3/2008 | Malandain et al. |
| 2008/0058944 A1 | 3/2008 | Duplessis et al. |
| 2008/0065082 A1 | 3/2008 | Chang et al. |
| 2008/0065219 A1 | 3/2008 | Dye |
| 2008/0071356 A1 | 3/2008 | Greenhalgh et al. |
| 2008/0071380 A1 | 3/2008 | Sweeney |
| 2008/0077148 A1 | 3/2008 | Ries et al. |
| 2008/0077150 A1 | 3/2008 | Nguyen |
| 2008/0077241 A1 | 3/2008 | Nguyen |
| 2008/0082172 A1 | 4/2008 | Jackson |
| 2008/0082173 A1 | 4/2008 | Delurio et al. |
| 2008/0097436 A1 | 4/2008 | Culbert et al. |
| 2008/0097454 A1 | 4/2008 | Deridder et al. |
| 2008/0097611 A1 | 4/2008 | Mastrorio et al. |
| 2008/0103601 A1 | 5/2008 | Biro et al. |
| 2008/0108990 A1 | 5/2008 | Mitchell et al. |
| 2008/0108996 A1 | 5/2008 | Padget et al. |
| 2008/0119935 A1 | 5/2008 | Alvarez |
| 2008/0125865 A1 | 5/2008 | Abdelgany |
| 2008/0132934 A1 | 6/2008 | Reiley et al. |
| 2008/0133012 A1 | 6/2008 | McGuckin |
| 2008/0133017 A1 | 6/2008 | Beyar et al. |
| 2008/0140085 A1 | 6/2008 | Gately et al. |
| 2008/0140207 A1 | 6/2008 | Olmos et al. |
| 2008/0147129 A1 | 6/2008 | Biedermann et al. |
| 2008/0147193 A1 | 6/2008 | Matthis et al. |
| 2008/0154377 A1 | 6/2008 | Voellmicke |
| 2008/0154379 A1 | 6/2008 | Steiner et al. |
| 2008/0161922 A1 | 7/2008 | Rhoda |
| 2008/0161927 A1 | 7/2008 | Savage et al. |
| 2008/0167657 A1 | 7/2008 | Greenhalgh |
| 2008/0172128 A1 | 7/2008 | Perez-Cruet et al. |
| 2008/0177306 A1 | 7/2008 | Lamborne et al. |
| 2008/0177312 A1 | 7/2008 | Perez-Cruet et al. |
| 2008/0177388 A1 | 7/2008 | Patterson et al. |
| 2008/0183204 A1 | 7/2008 | Greenhalgh et al. |
| 2008/0188945 A1 | 8/2008 | Boyce et al. |
| 2008/0195096 A1 | 8/2008 | Frei |
| 2008/0195209 A1 | 8/2008 | Garcia et al. |
| 2008/0195210 A1 | 8/2008 | Milijasevic et al. |
| 2008/0208255 A1 | 8/2008 | Siegal |
| 2008/0208344 A1 | 8/2008 | Kilpela et al. |
| 2008/0221586 A1 | 9/2008 | Garcia-Bengochea et al. |
| 2008/0221687 A1 | 9/2008 | Viker |
| 2008/0228225 A1 | 9/2008 | Trautwein et al. |
| 2008/0229597 A1 | 9/2008 | Malandain |
| 2008/0234732 A1 | 9/2008 | Landry et al. |
| 2008/0234733 A1 | 9/2008 | Scrantz et al. |
| 2008/0243126 A1 | 10/2008 | Gutierrez et al. |
| 2008/0243251 A1 | 10/2008 | Stad et al. |
| 2008/0243254 A1 | 10/2008 | Butler |
| 2008/0249622 A1 | 10/2008 | Gray |
| 2008/0249628 A1 | 10/2008 | Altarac et al. |
| 2008/0255563 A1 | 10/2008 | Farr et al. |
| 2008/0255574 A1 | 10/2008 | Dye |
| 2008/0255618 A1 | 10/2008 | Fisher et al. |
| 2008/0262619 A1 | 10/2008 | Ray |
| 2008/0269904 A1 | 10/2008 | Voorhies |
| 2008/0281346 A1 | 11/2008 | Greenhalgh et al. |
| 2008/0281364 A1 | 11/2008 | Chirico et al. |
| 2008/0281425 A1 | 11/2008 | Thalgott et al. |
| 2008/0287981 A1 | 11/2008 | Culbert et al. |
| 2008/0287997 A1 | 11/2008 | Altarac et al. |
| 2008/0300685 A1 | 12/2008 | Carls et al. |
| 2008/0306537 A1 | 12/2008 | Culbert |
| 2008/0312743 A1 | 12/2008 | Vila et al. |
| 2008/0319477 A1 | 12/2008 | Justis et al. |
| 2009/0005870 A1 | 1/2009 | Hawkins et al. |
| 2009/0005873 A1 | 1/2009 | Slivka et al. |
| 2009/0018524 A1 | 1/2009 | Greenhalgh et al. |
| 2009/0030423 A1 | 1/2009 | Puno |
| 2009/0048631 A1 | 2/2009 | Bhatnagar et al. |
| 2009/0048678 A1 | 2/2009 | Saal et al. |
| 2009/0054898 A1 | 2/2009 | Gleason |
| 2009/0054911 A1 | 2/2009 | Mueller et al. |
| 2009/0054988 A1 | 2/2009 | Hess |
| 2009/0054991 A1 | 2/2009 | Biyani et al. |
| 2009/0062807 A1 | 3/2009 | Song |
| 2009/0069813 A1 | 3/2009 | Von et al. |
| 2009/0069895 A1 | 3/2009 | Gittings et al. |
| 2009/0076607 A1 | 3/2009 | Aalsma et al. |
| 2009/0076610 A1 | 3/2009 | Afzal |
| 2009/0088789 A1 | 4/2009 | O'Neil et al. |
| 2009/0099568 A1 | 4/2009 | Lowry et al. |
| 2009/0105712 A1 | 4/2009 | Dauster et al. |
| 2009/0105745 A1 | 4/2009 | Culbert |
| 2009/0112217 A1 | 4/2009 | Hester |
| 2009/0112320 A1 | 4/2009 | Kraus |
| 2009/0112324 A1 | 4/2009 | Refai et al. |
| 2009/0131986 A1 | 5/2009 | Lee et al. |
| 2009/0143859 A1 | 6/2009 | McClellan et al. |
| 2009/0149857 A1 | 6/2009 | Culbert et al. |
| 2009/0164020 A1 | 6/2009 | Janowski et al. |
| 2009/0177281 A1 | 7/2009 | Swanson et al. |
| 2009/0177284 A1 | 7/2009 | Rogers et al. |
| 2009/0182429 A1 | 7/2009 | Humphreys et al. |
| 2009/0192613 A1 | 7/2009 | Wing et al. |
| 2009/0192614 A1 | 7/2009 | Beger et al. |
| 2009/0198339 A1 | 8/2009 | Kleiner et al. |
| 2009/0216234 A1 | 8/2009 | Farr et al. |
| 2009/0221967 A1 | 9/2009 | Thommen et al. |
| 2009/0222043 A1 | 9/2009 | Altarac et al. |
| 2009/0222096 A1 | 9/2009 | Trieu |
| 2009/0222099 A1 | 9/2009 | Liu et al. |
| 2009/0222100 A1 | 9/2009 | Cipoletti et al. |
| 2009/0234364 A1 | 9/2009 | Crook |
| 2009/0234389 A1 | 9/2009 | Chuang et al. |
| 2009/0234398 A1 | 9/2009 | Chirico et al. |
| 2009/0240333 A1 | 9/2009 | Trudeau et al. |
| 2009/0240334 A1 | 9/2009 | Richelsoph |
| 2009/0240335 A1 | 9/2009 | Arcenio et al. |
| 2009/0248159 A1 | 10/2009 | Aflatoon |
| 2009/0248163 A1 | 10/2009 | King et al. |
| 2009/0275890 A1 | 11/2009 | Leibowitz et al. |
| 2009/0276049 A1 | 11/2009 | Weiland |
| 2009/0276051 A1 | 11/2009 | Arramon et al. |
| 2009/0292361 A1 | 11/2009 | Lopez |
| 2009/0299479 A1 | 12/2009 | Jones et al. |
| 2010/0016905 A1 | 1/2010 | Greenhalgh et al. |
| 2010/0016968 A1 | 1/2010 | Moore |
| 2010/0030217 A1 | 2/2010 | Mitusina |
| 2010/0040332 A1 | 2/2010 | Van et al. |
| 2010/0042218 A1 | 2/2010 | Nebosky et al. |
| 2010/0049324 A1 | 2/2010 | Valdevit et al. |
| 2010/0057204 A1 | 3/2010 | Kadaba et al. |
| 2010/0070036 A1 | 3/2010 | Implicito |
| 2010/0076492 A1 | 3/2010 | Warner et al. |
| 2010/0076502 A1 | 3/2010 | Guyer et al. |
| 2010/0076559 A1 | 3/2010 | Bagga et al. |
| 2010/0082109 A1 | 4/2010 | Greenhalgh et al. |
| 2010/0094422 A1 | 4/2010 | Hansell et al. |
| 2010/0094424 A1 | 4/2010 | Woodburn et al. |
| 2010/0094426 A1 | 4/2010 | Grohowski et al. |
| 2010/0100098 A1 | 4/2010 | Norton et al. |
| 2010/0100183 A1 | 4/2010 | Prewett et al. |
| 2010/0106191 A1 | 4/2010 | Yue et al. |
| 2010/0114105 A1 | 5/2010 | Butters et al. |

(56) References Cited

U.S. PATENT DOCUMENTS

| | | |
|---|---|---|
| 2010/0114147 A1 | 5/2010 | Biyani |
| 2010/0125334 A1 | 5/2010 | Krueger |
| 2010/0174314 A1 | 7/2010 | Mirkovic et al. |
| 2010/0179594 A1 | 7/2010 | Theofilos et al. |
| 2010/0185290 A1 | 7/2010 | Compton et al. |
| 2010/0185292 A1 | 7/2010 | Hochschuler et al. |
| 2010/0191241 A1 | 7/2010 | McCormack et al. |
| 2010/0191334 A1 | 7/2010 | Keller |
| 2010/0191336 A1 | 7/2010 | Greenhalgh |
| 2010/0204795 A1 | 8/2010 | Greenhalgh |
| 2010/0204796 A1 | 8/2010 | Bae et al. |
| 2010/0211107 A1 | 8/2010 | Muhanna |
| 2010/0211176 A1 | 8/2010 | Greenhalgh |
| 2010/0211182 A1 | 8/2010 | Zimmermann |
| 2010/0217269 A1 | 8/2010 | Landes |
| 2010/0222884 A1 | 9/2010 | Greenhalgh |
| 2010/0234849 A1 | 9/2010 | Bouadi |
| 2010/0234956 A1 | 9/2010 | Attia et al. |
| 2010/0241231 A1 | 9/2010 | Marino et al. |
| 2010/0249935 A1 | 9/2010 | Slivka et al. |
| 2010/0256768 A1 | 10/2010 | Lim et al. |
| 2010/0262240 A1 | 10/2010 | Chavatte et al. |
| 2010/0268231 A1 | 10/2010 | Kuslich et al. |
| 2010/0268338 A1 | 10/2010 | Melkent et al. |
| 2010/0274358 A1 | 10/2010 | Mueller et al. |
| 2010/0286783 A1 | 11/2010 | Lechmann et al. |
| 2010/0292700 A1 | 11/2010 | Ries |
| 2010/0298938 A1 | 11/2010 | Humphreys et al. |
| 2010/0305700 A1 | 12/2010 | Ben-Arye et al. |
| 2010/0305704 A1 | 12/2010 | Messerli et al. |
| 2010/0324607 A1 | 12/2010 | Davis |
| 2010/0331845 A1 | 12/2010 | Foley et al. |
| 2010/0331891 A1 | 12/2010 | Culbert et al. |
| 2011/0004216 A1 | 1/2011 | Amendola et al. |
| 2011/0004308 A1 | 1/2011 | Marino et al. |
| 2011/0004310 A1 | 1/2011 | Michelson |
| 2011/0009970 A1 | 1/2011 | Puno |
| 2011/0015747 A1 | 1/2011 | McManus et al. |
| 2011/0029082 A1 | 2/2011 | Hall |
| 2011/0029083 A1 | 2/2011 | Hynes et al. |
| 2011/0029085 A1 | 2/2011 | Hynes et al. |
| 2011/0029086 A1 | 2/2011 | Glazer et al. |
| 2011/0035011 A1 | 2/2011 | Cain |
| 2011/0046674 A1 | 2/2011 | Calvosa et al. |
| 2011/0054538 A1 | 3/2011 | Zehavi et al. |
| 2011/0066186 A1 | 3/2011 | Boyer et al. |
| 2011/0071527 A1 | 3/2011 | Nelson et al. |
| 2011/0082552 A1 | 4/2011 | Wistrom et al. |
| 2011/0093074 A1 | 4/2011 | Glerum et al. |
| 2011/0093076 A1 | 4/2011 | Reo et al. |
| 2011/0098531 A1 | 4/2011 | To |
| 2011/0098628 A1 | 4/2011 | Yeung et al. |
| 2011/0098818 A1 | 4/2011 | Brodke et al. |
| 2011/0112586 A1 | 5/2011 | Guyer et al. |
| 2011/0130835 A1 | 6/2011 | Ashley et al. |
| 2011/0130838 A1 | 6/2011 | Morgenstern Lopez |
| 2011/0144692 A1 | 6/2011 | Saladin et al. |
| 2011/0144753 A1 | 6/2011 | Marchek et al. |
| 2011/0153020 A1 | 6/2011 | Abdelgany et al. |
| 2011/0159070 A1 | 6/2011 | Jin et al. |
| 2011/0160773 A1 | 6/2011 | Aschmann et al. |
| 2011/0160866 A1 | 6/2011 | Laurence et al. |
| 2011/0172716 A1 | 7/2011 | Glerum |
| 2011/0172774 A1 | 7/2011 | Varela |
| 2011/0190816 A1 | 8/2011 | Sheffer et al. |
| 2011/0190891 A1 | 8/2011 | Suh et al. |
| 2011/0238072 A1 | 9/2011 | Tyndall |
| 2011/0270261 A1 | 11/2011 | Mast et al. |
| 2011/0276142 A1 | 11/2011 | Niemiec et al. |
| 2011/0282453 A1 | 11/2011 | Greenhalgh et al. |
| 2011/0282459 A1 | 11/2011 | McClellan et al. |
| 2011/0301711 A1 | 12/2011 | Palmatier et al. |
| 2011/0301712 A1 | 12/2011 | Palmatier et al. |
| 2011/0307010 A1 | 12/2011 | Pradhan |
| 2011/0313465 A1 | 12/2011 | Warren et al. |
| 2011/0320000 A1 | 12/2011 | O'Neil et al. |
| 2012/0004726 A1 | 1/2012 | Greenhalgh et al. |
| 2012/0004732 A1 | 1/2012 | Goel et al. |
| 2012/0010715 A1 | 1/2012 | Spann |
| 2012/0022654 A1 | 1/2012 | Farris et al. |
| 2012/0029636 A1 | 2/2012 | Ragab et al. |
| 2012/0029639 A1 | 2/2012 | Blackwell et al. |
| 2012/0035730 A1 | 2/2012 | Spann |
| 2012/0059474 A1 | 3/2012 | Weiman |
| 2012/0059475 A1 | 3/2012 | Weiman |
| 2012/0071977 A1 | 3/2012 | Oglaza et al. |
| 2012/0071980 A1 | 3/2012 | Purcell et al. |
| 2012/0083889 A1 | 4/2012 | Purcell et al. |
| 2012/0123546 A1 | 5/2012 | Medina |
| 2012/0136443 A1 | 5/2012 | Wenzel |
| 2012/0150304 A1 | 6/2012 | Glerum et al. |
| 2012/0150305 A1 | 6/2012 | Glerum et al. |
| 2012/0158146 A1 | 6/2012 | Glerum et al. |
| 2012/0158147 A1 | 6/2012 | Glerum et al. |
| 2012/0158148 A1 | 6/2012 | Glerum et al. |
| 2012/0185049 A1 | 7/2012 | Varela |
| 2012/0197299 A1 | 8/2012 | Fabian, Jr. |
| 2012/0197403 A1 | 8/2012 | Merves |
| 2012/0197405 A1 | 8/2012 | Cuevas et al. |
| 2012/0203290 A1 | 8/2012 | Warren et al. |
| 2012/0203347 A1 | 8/2012 | Glerum et al. |
| 2012/0209383 A1 | 8/2012 | Tsuang et al. |
| 2012/0215262 A1 | 8/2012 | Culbert et al. |
| 2012/0215315 A1 | 8/2012 | Hochschuler et al. |
| 2012/0215316 A1 | 8/2012 | Mohr et al. |
| 2012/0226357 A1 | 9/2012 | Varela |
| 2012/0232552 A1 | 9/2012 | Morgenstern et al. |
| 2012/0232658 A1 | 9/2012 | Morgenstern et al. |
| 2012/0253395 A1 | 10/2012 | Linares |
| 2012/0253406 A1 | 10/2012 | Bae et al. |
| 2012/0265309 A1 | 10/2012 | Glerum et al. |
| 2012/0277795 A1 | 11/2012 | Von et al. |
| 2012/0277869 A1 | 11/2012 | Siccardi et al. |
| 2012/0277877 A1 | 11/2012 | Smith et al. |
| 2012/0283837 A1 | 11/2012 | Bae et al. |
| 2012/0290090 A1 | 11/2012 | Glerum et al. |
| 2012/0290097 A1 | 11/2012 | Cipoletti et al. |
| 2012/0310350 A1 | 12/2012 | Farris et al. |
| 2012/0310352 A1 | 12/2012 | Dimauro et al. |
| 2012/0323327 A1 | 12/2012 | McAfee |
| 2012/0323328 A1 | 12/2012 | Weiman |
| 2012/0330421 A1 | 12/2012 | Weiman |
| 2012/0330422 A1 | 12/2012 | Weiman |
| 2013/0006361 A1 | 1/2013 | Glerum et al. |
| 2013/0023993 A1 | 1/2013 | Weiman |
| 2013/0023994 A1 | 1/2013 | Glerum |
| 2013/0030536 A1 | 1/2013 | Rhoda et al. |
| 2013/0030544 A1 | 1/2013 | Studer |
| 2013/0053966 A1 | 2/2013 | Jimenez et al. |
| 2013/0060337 A1 | 3/2013 | Petersheim et al. |
| 2013/0073044 A1 | 3/2013 | Gamache |
| 2013/0079790 A1 | 3/2013 | Stein et al. |
| 2013/0085572 A1 | 4/2013 | Glerum et al. |
| 2013/0085574 A1 | 4/2013 | Sledge |
| 2013/0109925 A1 | 5/2013 | Horton et al. |
| 2013/0110240 A1 | 5/2013 | Hansell et al. |
| 2013/0116791 A1 | 5/2013 | Theofilos |
| 2013/0123924 A1 | 5/2013 | Butler et al. |
| 2013/0123927 A1 | 5/2013 | Malandain |
| 2013/0138214 A1 | 5/2013 | Greenhalgh et al. |
| 2013/0144387 A1 | 6/2013 | Walker et al. |
| 2013/0144388 A1 | 6/2013 | Emery et al. |
| 2013/0150906 A1 | 6/2013 | Kerboul et al. |
| 2013/0158663 A1 | 6/2013 | Miller et al. |
| 2013/0158664 A1 | 6/2013 | Palmatier et al. |
| 2013/0158667 A1 | 6/2013 | Tabor et al. |
| 2013/0158668 A1 | 6/2013 | Nichols et al. |
| 2013/0158669 A1 | 6/2013 | Sungarian et al. |
| 2013/0173004 A1 | 7/2013 | Greenhalgh et al. |
| 2013/0190875 A1 | 7/2013 | Shulock et al. |
| 2013/0190876 A1 | 7/2013 | Drochner et al. |
| 2013/0190877 A1 | 7/2013 | Medina |
| 2013/0197647 A1 | 8/2013 | Wolters et al. |
| 2013/0204371 A1 | 8/2013 | McLuen et al. |

(56) References Cited

U.S. PATENT DOCUMENTS

| | | |
|---|---|---|
| 2013/0211525 A1 | 8/2013 | McLuen et al. |
| 2013/0211526 A1 | 8/2013 | Alheidt et al. |
| 2013/0218276 A1 | 8/2013 | Fiechter et al. |
| 2013/0231747 A1 | 9/2013 | Olmos et al. |
| 2013/0238006 A1 | 9/2013 | O'Neil et al. |
| 2013/0253585 A1 | 9/2013 | Garcia et al. |
| 2013/0261746 A1 | 10/2013 | Linares et al. |
| 2013/0261747 A1 | 10/2013 | Geisert |
| 2013/0268077 A1 | 10/2013 | You et al. |
| 2013/0310937 A1 | 11/2013 | Luiz |
| 2013/0310939 A1 | 11/2013 | Fabian et al. |
| 2013/0325128 A1 | 12/2013 | Perloff et al. |
| 2014/0018816 A1 | 1/2014 | Fenn et al. |
| 2014/0025169 A1 | 1/2014 | Lechmann et al. |
| 2014/0039622 A1 | 2/2014 | Glerum et al. |
| 2014/0039626 A1 | 2/2014 | Dale |
| 2014/0046333 A1 | 2/2014 | Johnson et al. |
| 2014/0046446 A1 | 2/2014 | Robinson |
| 2014/0052259 A1 | 2/2014 | Garner et al. |
| 2014/0058512 A1 | 2/2014 | Petersheim |
| 2014/0058513 A1 | 2/2014 | Gahman et al. |
| 2014/0067073 A1 | 3/2014 | Hauck |
| 2014/0081267 A1 | 3/2014 | Orsak et al. |
| 2014/0086962 A1 | 3/2014 | Jin et al. |
| 2014/0094916 A1 | 4/2014 | Glerum et al. |
| 2014/0100662 A1 | 4/2014 | Patterson et al. |
| 2014/0114414 A1 | 4/2014 | Abdou et al. |
| 2014/0114423 A1 | 4/2014 | Suedkamp et al. |
| 2014/0128977 A1 | 5/2014 | Glerum et al. |
| 2014/0128980 A1 | 5/2014 | Kirschman |
| 2014/0135934 A1 | 5/2014 | Hansell et al. |
| 2014/0142706 A1 | 5/2014 | Hansell et al. |
| 2014/0163682 A1 | 6/2014 | Lott et al. |
| 2014/0163683 A1 | 6/2014 | Seifert et al. |
| 2014/0172103 A1 | 6/2014 | O'Neil et al. |
| 2014/0172105 A1 | 6/2014 | Frasier et al. |
| 2014/0172106 A1 | 6/2014 | To et al. |
| 2014/0180421 A1 | 6/2014 | Glerum et al. |
| 2014/0188225 A1 | 7/2014 | Dmuschewsky |
| 2014/0228959 A1 | 8/2014 | Niemiec et al. |
| 2014/0236296 A1 | 8/2014 | Wagner et al. |
| 2014/0243981 A1 | 8/2014 | Davenport et al. |
| 2014/0243982 A1 | 8/2014 | Miller |
| 2014/0249629 A1 | 9/2014 | Moskowitz et al. |
| 2014/0249630 A1 | 9/2014 | Weiman |
| 2014/0257484 A1 | 9/2014 | Flower et al. |
| 2014/0257486 A1 | 9/2014 | Alheidt |
| 2014/0257494 A1 | 9/2014 | Thorwarth et al. |
| 2014/0277139 A1 | 9/2014 | Vrionis et al. |
| 2014/0277204 A1 | 9/2014 | Sandhu |
| 2014/0277464 A1 | 9/2014 | Richter et al. |
| 2014/0277474 A1 | 9/2014 | Robinson et al. |
| 2014/0277476 A1 | 9/2014 | McLean et al. |
| 2014/0277481 A1 | 9/2014 | Lee et al. |
| 2014/0303731 A1 | 10/2014 | Glerum |
| 2014/0303732 A1 | 10/2014 | Rhoda et al. |
| 2014/0324171 A1 | 10/2014 | Glerum et al. |
| 2014/0336771 A1 | 11/2014 | Zambiasi et al. |
| 2015/0012097 A1 | 1/2015 | Ibarra et al. |
| 2015/0012098 A1 | 1/2015 | Eastlack et al. |
| 2015/0045894 A1 | 2/2015 | Hawkins et al. |
| 2015/0051701 A1 | 2/2015 | Glerum et al. |
| 2015/0066145 A1 | 3/2015 | Rogers et al. |
| 2015/0088256 A1 | 3/2015 | Ballard |
| 2015/0094610 A1 | 4/2015 | Morgenstern et al. |
| 2015/0094812 A1 | 4/2015 | Cain |
| 2015/0094813 A1 | 4/2015 | Lechmann et al. |
| 2015/0100128 A1 | 4/2015 | Glerum et al. |
| 2015/0112398 A1 | 4/2015 | Morgenstern et al. |
| 2015/0112437 A1 | 4/2015 | Davis et al. |
| 2015/0112438 A1 | 4/2015 | McLean |
| 2015/0157470 A1 | 6/2015 | Voellmicke et al. |
| 2015/0164655 A1 | 6/2015 | Dimauro |
| 2015/0173914 A1 | 6/2015 | Dimauro et al. |
| 2015/0173916 A1 | 6/2015 | Cain |
| 2015/0182347 A1 | 7/2015 | Robinson |
| 2015/0190242 A1 | 7/2015 | Blain et al. |
| 2015/0196400 A1 | 7/2015 | Dace |
| 2015/0196401 A1 | 7/2015 | Dimauro et al. |
| 2015/0202052 A1 | 7/2015 | Dimauro |
| 2015/0216671 A1 | 8/2015 | Cain |
| 2015/0216672 A1 | 8/2015 | Cain |
| 2015/0216673 A1 | 8/2015 | Dimauro |
| 2015/0230932 A1 | 8/2015 | Schaller |
| 2015/0238324 A1 | 8/2015 | Nebosky et al. |
| 2015/0250606 A1 | 9/2015 | McLean |
| 2015/0320571 A1 | 11/2015 | Lechmann et al. |
| 2016/0000577 A1 | 1/2016 | Dimauro |
| 2016/0016309 A1 | 1/2016 | Swift et al. |
| 2016/0022437 A1 | 1/2016 | Kelly et al. |
| 2016/0038301 A1 | 2/2016 | Wickham |
| 2016/0038304 A1 | 2/2016 | Aquino et al. |
| 2016/0045333 A1 | 2/2016 | Baynham |
| 2016/0051376 A1 | 2/2016 | Serhan et al. |
| 2016/0058573 A1 | 3/2016 | Dimauro et al. |
| 2016/0067055 A1 | 3/2016 | Hawkins et al. |
| 2016/0074170 A1 | 3/2016 | Rogers et al. |
| 2016/0074175 A1 | 3/2016 | O'Neil |
| 2016/0081814 A1 | 3/2016 | Baynham |
| 2016/0089247 A1 | 3/2016 | Nichols et al. |
| 2016/0100954 A1 | 4/2016 | Rumi et al. |
| 2016/0106551 A1 | 4/2016 | Grimberg et al. |
| 2016/0113776 A1 | 4/2016 | Capote |
| 2016/0120662 A1 | 5/2016 | Schaller |
| 2016/0128843 A1 | 5/2016 | Tsau et al. |
| 2016/0199196 A1 | 7/2016 | Serhan et al. |
| 2016/0228258 A1 | 8/2016 | Schaller et al. |
| 2016/0242929 A1 | 8/2016 | Voellmicke et al. |
| 2016/0256291 A1 | 9/2016 | Miller |
| 2016/0296342 A1 | 10/2016 | Woods |
| 2016/0310296 A1 | 10/2016 | Dimauro et al. |
| 2016/0317313 A1 | 11/2016 | Dimauro |
| 2016/0317317 A1 | 11/2016 | Marchek et al. |
| 2016/0317714 A1 | 11/2016 | Dimauro et al. |
| 2016/0331541 A1 | 11/2016 | Dimauro et al. |
| 2016/0331546 A1 | 11/2016 | Lechmann et al. |
| 2016/0331548 A1 | 11/2016 | Dimauro et al. |
| 2016/0338854 A1 | 11/2016 | Serhan et al. |
| 2016/0367265 A1 | 12/2016 | Morgenstern Lopez |
| 2016/0367380 A1 | 12/2016 | Dimauro |
| 2016/0374821 A1 | 12/2016 | Dimauro et al. |
| 2017/0000622 A1 | 1/2017 | Thommen et al. |
| 2017/0035578 A1 | 2/2017 | Dimauro et al. |
| 2017/0065427 A1 | 3/2017 | Songer |
| 2017/0095341 A1 | 4/2017 | Smith |
| 2017/0100255 A1 | 4/2017 | Hleihil et al. |
| 2017/0100260 A1 | 4/2017 | Duffield et al. |
| 2017/0119542 A1 | 5/2017 | Logan et al. |
| 2017/0290674 A1 | 10/2017 | Olmos et al. |
| 2017/0290675 A1 | 10/2017 | Olmos et al. |
| 2017/0290677 A1 | 10/2017 | Olmos et al. |
| 2017/0304074 A1 | 10/2017 | Dimauro et al. |
| 2018/0028200 A1 | 2/2018 | O'Neil et al. |
| 2018/0036141 A1 | 2/2018 | ONeil et al. |
| 2018/0055649 A1 | 3/2018 | Kelly et al. |
| 2018/0078379 A1 | 3/2018 | Serhan et al. |
| 2018/0161171 A1 | 6/2018 | Frasier et al. |
| 2018/0161175 A1 | 6/2018 | Frasier et al. |
| 2018/0256360 A1 | 9/2018 | Cain |
| 2018/0256362 A1 | 9/2018 | Slivka et al. |
| 2019/0083276 A1 | 3/2019 | Dimauro |
| 2019/0105171 A1 | 4/2019 | Rogers et al. |
| 2019/0142602 A1 | 5/2019 | Olmos et al. |
| 2019/0388238 A1 | 12/2019 | Lechmann et al. |
| 2020/0008950 A1 | 1/2020 | Serhan et al. |
| 2020/0015982 A1 | 1/2020 | O'Neil |
| 2020/0030114 A1 | 1/2020 | Cain |
| 2020/0297506 A1 | 9/2020 | Olmos et al. |
| 2020/0375754 A1 | 12/2020 | Cain |
| 2020/0375755 A1 | 12/2020 | Cain |
| 2020/0383799 A1 | 12/2020 | Cain |
| 2020/0405497 A1 | 12/2020 | Olmos et al. |
| 2021/0000160 A1 | 1/2021 | Olmos et al. |

(56) References Cited

U.S. PATENT DOCUMENTS

FOREIGN PATENT DOCUMENTS

| | | |
|---|---|---|
| CA | 2617872 A1 | 2/2007 |
| CN | 1177918 A | 4/1998 |
| CN | 1383790 A | 12/2002 |
| CN | 1819805 A | 8/2006 |
| CN | 101031260 A | 9/2007 |
| CN | 101087566 A | 12/2007 |
| CN | 101185594 A | 5/2008 |
| CN | 101631516 A | 1/2010 |
| CN | 101909548 A | 12/2010 |
| CN | 102164552 A | 8/2011 |
| CN | 107510524 A | 12/2017 |
| DE | 2804936 A1 | 8/1979 |
| DE | 3023353 A1 | 4/1981 |
| DE | 3801459 A1 | 8/1989 |
| DE | 3911610 A1 | 10/1990 |
| DE | 4012622 C1 | 7/1991 |
| DE | 9407806 U1 | 7/1994 |
| DE | 19710392 C1 | 7/1999 |
| DE | 19832798 C1 | 11/1999 |
| DE | 20101793 U1 | 5/2001 |
| DE | 202006005868 U1 | 6/2006 |
| DE | 202008001079 U1 | 3/2008 |
| DE | 10357960 B4 | 9/2015 |
| EP | 0077159 A1 | 4/1983 |
| EP | 0260044 A1 | 3/1988 |
| EP | 0270704 A1 | 6/1988 |
| EP | 0282161 A1 | 9/1988 |
| EP | 0433717 A1 | 6/1991 |
| EP | 0509084 A1 | 10/1992 |
| EP | 0525352 A1 | 2/1993 |
| EP | 0529275 A2 | 3/1993 |
| EP | 0609084 A2 | 8/1994 |
| EP | 0611557 A2 | 8/1994 |
| EP | 0621020 A1 | 10/1994 |
| EP | 0625336 A2 | 11/1994 |
| EP | 0678489 A1 | 10/1995 |
| EP | 0743045 A2 | 11/1996 |
| EP | 0853929 A2 | 7/1998 |
| EP | 1046376 A1 | 10/2000 |
| EP | 1157676 A1 | 11/2001 |
| EP | 1283026 A2 | 2/2003 |
| EP | 1290985 A2 | 3/2003 |
| EP | 1308132 A2 | 5/2003 |
| EP | 1374784 A1 | 1/2004 |
| EP | 1378205 A1 | 1/2004 |
| EP | 1405602 A1 | 4/2004 |
| EP | 1532949 A1 | 5/2005 |
| EP | 1541096 A1 | 6/2005 |
| EP | 1605836 A1 | 12/2005 |
| EP | 1385449 B1 | 7/2006 |
| EP | 1683593 A2 | 7/2006 |
| EP | 1698305 A1 | 9/2006 |
| EP | 1829486 A1 | 9/2007 |
| EP | 1843723 A1 | 10/2007 |
| EP | 1845874 A1 | 10/2007 |
| EP | 1924227 A2 | 5/2008 |
| EP | 1925272 | 5/2008 |
| EP | 2331023 A2 | 6/2011 |
| EP | 2368529 A1 | 9/2011 |
| EP | 2237748 B1 | 9/2012 |
| EP | 2641571 A1 | 9/2013 |
| EP | 2705809 A1 | 3/2014 |
| EP | 2764851 A1 | 8/2014 |
| EP | 2645965 B1 | 8/2016 |
| FR | 2649311 A1 | 1/1991 |
| FR | 2699065 A1 | 6/1994 |
| FR | 2712486 A1 | 5/1995 |
| FR | 2718635 A1 | 10/1995 |
| FR | 2728778 A1 | 7/1996 |
| FR | 2730159 A1 | 8/1996 |
| FR | 2745709 A1 | 9/1997 |
| FR | 2800601 A1 | 5/2001 |
| FR | 2801189 A1 | 5/2001 |
| FR | 2808182 A1 | 11/2001 |
| FR | 2874814 A1 | 3/2006 |
| FR | 2913331 A1 | 9/2008 |
| FR | 2948277 | 1/2011 |
| GB | 2157788 A | 10/1985 |
| GB | 2173565 A | 10/1986 |
| JP | 64-052439 A | 2/1989 |
| JP | 06-500039 A | 1/1994 |
| JP | 06-319742 A | 11/1994 |
| JP | 07-502419 A | 3/1995 |
| JP | 07-184922 A | 7/1995 |
| JP | 07-213533 A | 8/1995 |
| JP | 10-085232 A | 4/1998 |
| JP | 11-089854 A | 4/1999 |
| JP | 2003-010197 A | 1/2003 |
| JP | 2003-126266 A | 5/2003 |
| JP | 2003-526457 A | 9/2003 |
| JP | 2006-501901 A | 1/2006 |
| JP | 2006-516456 | 7/2006 |
| JP | 2007-054666 A | 3/2007 |
| JP | 2007-530243 A | 11/2007 |
| JP | 2008-507363 A | 3/2008 |
| JP | 2008-126085 A | 6/2008 |
| JP | 2011-509766 A | 3/2011 |
| JP | 2011-520580 A | 7/2011 |
| JP | 2012-020153 A | 2/2012 |
| JP | 2012-508048 A | 4/2012 |
| JP | 4988203 B2 | 8/2012 |
| JP | 2013-508031 | 3/2013 |
| JP | 5164571 B2 | 3/2013 |
| JP | 2014-502867 A | 2/2014 |
| KR | 20-0290058 Y1 | 9/2002 |
| WO | 91/09572 A1 | 7/1991 |
| WO | 92/04423 A2 | 3/1992 |
| WO | 92/07594 A1 | 5/1992 |
| WO | 92/14423 A1 | 9/1992 |
| WO | 93/04634 A1 | 3/1993 |
| WO | 93/04652 A1 | 3/1993 |
| WO | 93/17669 A1 | 9/1993 |
| WO | 94/04100 A1 | 3/1994 |
| WO | 95/31158 | 11/1995 |
| WO | 96/28100 A1 | 9/1996 |
| WO | 97/00054 A1 | 1/1997 |
| WO | 97/26847 A1 | 7/1997 |
| WO | 98/34552 A1 | 8/1998 |
| WO | 98/34568 A1 | 8/1998 |
| WO | 99/02214 A1 | 1/1999 |
| WO | 99/26562 A1 | 6/1999 |
| WO | 99/42062 A1 | 8/1999 |
| WO | 99/52478 A1 | 10/1999 |
| WO | 99/53871 A1 | 10/1999 |
| WO | 99/60956 A1 | 12/1999 |
| WO | 99/62417 A1 | 12/1999 |
| WO | 99/63914 A1 | 12/1999 |
| WO | 00/12033 | 3/2000 |
| WO | 00/13620 A1 | 3/2000 |
| WO | 00/24343 A1 | 5/2000 |
| WO | 00/67652 | 5/2000 |
| WO | 00/44288 A1 | 8/2000 |
| WO | 00/53127 A1 | 9/2000 |
| WO | 00/67650 A1 | 11/2000 |
| WO | 00/67651 A1 | 11/2000 |
| WO | 00/74605 A1 | 12/2000 |
| WO | 00/76409 A1 | 12/2000 |
| WO | 01/01893 A1 | 1/2001 |
| WO | 01/01895 A1 | 1/2001 |
| WO | 01/10316 A1 | 2/2001 |
| WO | 01/12054 A2 | 2/2001 |
| WO | 01/17464 A1 | 3/2001 |
| WO | 01/80751 A1 | 11/2001 |
| WO | 01/95838 A1 | 12/2001 |
| WO | 02/03870 A1 | 1/2002 |
| WO | 02/17824 A2 | 3/2002 |
| WO | 02/17825 A2 | 3/2002 |
| WO | 02/30338 A1 | 4/2002 |
| WO | 02/43601 A2 | 6/2002 |
| WO | 02/43628 A1 | 6/2002 |
| WO | 02/45627 A1 | 6/2002 |
| WO | 02/47563 A1 | 6/2002 |

(56) References Cited

FOREIGN PATENT DOCUMENTS

| | | |
|---|---|---|
| WO | 02/71921 A2 | 9/2002 |
| WO | 02/85250 A2 | 10/2002 |
| WO | 03/02021 A2 | 1/2003 |
| WO | 03/05937 A1 | 1/2003 |
| WO | 03/07854 A1 | 1/2003 |
| WO | 03/20169 A2 | 3/2003 |
| WO | 03/21308 A2 | 3/2003 |
| WO | 03/22165 A1 | 3/2003 |
| WO | 03/28587 A2 | 4/2003 |
| WO | 03/43488 A2 | 5/2003 |
| WO | 03/03951 A1 | 6/2003 |
| WO | 2003/101308 A1 | 12/2003 |
| WO | 2004/008949 A2 | 1/2004 |
| WO | 03/59180 A2 | 3/2004 |
| WO | 2004/030582 A2 | 4/2004 |
| WO | 2004/034924 A2 | 4/2004 |
| WO | 2004/062505 A1 | 7/2004 |
| WO | 2004/064603 A2 | 8/2004 |
| WO | 2004/069033 A2 | 8/2004 |
| WO | 2004/073563 A2 | 9/2004 |
| WO | 2004/078220 A2 | 9/2004 |
| WO | 2004/078221 A2 | 9/2004 |
| WO | 2004/080316 A1 | 9/2004 |
| WO | 2004/082526 A2 | 9/2004 |
| WO | 2004/098420 A2 | 11/2004 |
| WO | 2004/098453 A2 | 11/2004 |
| WO | 2004/108022 A1 | 12/2004 |
| WO | 2005/027734 A2 | 3/2005 |
| WO | 2005/032433 A2 | 4/2005 |
| WO | 2005/039455 A1 | 5/2005 |
| WO | 2005/051246 A2 | 6/2005 |
| WO | 2005/081877 A2 | 9/2005 |
| WO | 2005/094297 A2 | 10/2005 |
| WO | 2005/112834 A2 | 12/2005 |
| WO | 2005/112835 A2 | 12/2005 |
| WO | 2005/115261 A1 | 12/2005 |
| WO | 2006/017507 A2 | 2/2006 |
| WO | 2006/044920 A2 | 4/2006 |
| WO | 2006/047587 A2 | 5/2006 |
| WO | 2006/047645 A2 | 5/2006 |
| WO | 2006/058079 A2 | 6/2006 |
| WO | 2006/058281 A2 | 6/2006 |
| WO | 2006/060420 A1 | 6/2006 |
| WO | 2006/063083 A1 | 6/2006 |
| WO | 2006/065419 A2 | 6/2006 |
| WO | 2006/066228 A2 | 6/2006 |
| WO | 2006/072941 A2 | 7/2006 |
| WO | 2006/081843 A1 | 8/2006 |
| WO | 2006/108067 A2 | 10/2006 |
| WO | 2006/118944 A1 | 11/2006 |
| WO | 2007/009107 A2 | 1/2007 |
| WO | 2007/022194 A2 | 2/2007 |
| WO | 2007/028098 A2 | 3/2007 |
| WO | 2007/048012 A2 | 4/2007 |
| WO | 2007/067726 A2 | 6/2007 |
| WO | 2007/084427 A2 | 7/2007 |
| WO | 2007/119212 A2 | 10/2007 |
| WO | 2007/124130 A2 | 11/2007 |
| WO | 2008/005627 A2 | 1/2008 |
| WO | 2008/011378 A1 | 1/2008 |
| WO | 2008/044057 A1 | 4/2008 |
| WO | 2008/064842 A2 | 6/2008 |
| WO | 2008/070863 A2 | 6/2008 |
| WO | 2008/103781 A2 | 8/2008 |
| WO | 2008/103832 A2 | 8/2008 |
| WO | 2009/064787 A2 | 5/2009 |
| WO | 2009/092102 A1 | 7/2009 |
| WO | 2009/124269 A1 | 10/2009 |
| WO | 2009/143496 A1 | 11/2009 |
| WO | 2009/147527 A2 | 12/2009 |
| WO | 2009/152919 A1 | 12/2009 |
| WO | 2010/011348 A1 | 1/2010 |
| WO | 2010/068725 A2 | 6/2010 |
| WO | 2010/075451 A1 | 7/2010 |
| WO | 2010/075555 A2 | 7/2010 |
| WO | 2010/088766 A1 | 8/2010 |
| WO | 2010/121002 A1 | 10/2010 |
| WO | 2010/136170 A1 | 12/2010 |
| WO | 2010/148112 A1 | 12/2010 |
| WO | 2011/013047 A2 | 2/2011 |
| WO | 2011/046459 A1 | 4/2011 |
| WO | 2011/046460 A1 | 4/2011 |
| WO | 2011/060087 A1 | 5/2011 |
| WO | 2011/079910 A2 | 7/2011 |
| WO | 2011/119617 A1 | 9/2011 |
| WO | 2011/142761 A1 | 11/2011 |
| WO | 2011/150350 A1 | 12/2011 |
| WO | 2012/009152 A1 | 1/2012 |
| WO | 2012/027490 A2 | 3/2012 |
| WO | 2012/028182 A1 | 3/2012 |
| WO | 2012/030331 A1 | 3/2012 |
| WO | 2012/089317 A1 | 7/2012 |
| WO | 2012/103254 A2 | 8/2012 |
| WO | 2012/122294 A1 | 9/2012 |
| WO | 2012/129197 A1 | 9/2012 |
| WO | 2012/135764 A1 | 10/2012 |
| WO | 2013/006669 A2 | 1/2013 |
| WO | 2013/023096 A1 | 2/2013 |
| WO | 2013/025876 A1 | 2/2013 |
| WO | 2013/043850 A2 | 3/2013 |
| WO | 2013/062903 A1 | 5/2013 |
| WO | 2013/082184 A1 | 6/2013 |
| WO | 2013/149611 A1 | 10/2013 |
| WO | 2013/158294 A1 | 10/2013 |
| WO | 2013/173767 A1 | 11/2013 |
| WO | 2013/184946 A1 | 12/2013 |
| WO | 2014/014610 A1 | 1/2014 |
| WO | 2014/018098 A1 | 1/2014 |
| WO | 2014/026007 A1 | 2/2014 |
| WO | 2014/035962 A1 | 3/2014 |
| WO | 2014/088521 A2 | 6/2014 |
| WO | 2014/116891 A1 | 7/2014 |
| WO | 2014/144696 A1 | 9/2014 |
| WO | 2015/048997 A1 | 4/2015 |
| WO | 2016/069796 A1 | 5/2016 |
| WO | 2016/127139 A1 | 8/2016 |

OTHER PUBLICATIONS

Alfen et al., "Developments in the area of Endoscopic Spine Surgery", European Musculoskeletal Review 2006, pp. 23-24, ThessysTM, Transforaminal Endoscopic Spine Systems, joi max Medical Solutions.

Brochure for Perpos PLS System Surgical Technique by Interventional Spine, 2008, 8 pages.

Brooks et al., "Efficacy of Supplemental Posterior Transfacet Pedicle Device Fixation in the Setting of One- or Two-Level Anterior Lumbar Interbody Fusion", Retrieved Jun. 19, 2017, 6 pages.

Bruder et al., Identification and characterization of a cell surface differentiation antigen on human osteoprogenitor cells. 42nd Annual Meeting of the Orthopaedic Research Society. p. 574, Feb. 19-22, 1996, Atlanta, Georgia.

Bruder et al., Monoclonal antibodies reactive with human osteogenic cell surface antigens. Bone. Sep. 1997;21 (3):225-235.

Burkoth et al., A review of photocrosslinked polyanhydrides: in situ forming degradable networks. Biomaterials. Dec. 2000; 21 (23): 2395-2404.

Cambridge Scientific News, FDA Approves Cambridge Scientific, Inc.'s Orthopedic WISORB (TM) Malleolar Screw [online], Jul. 30, 2002 [retrieved on Oct. 14, 2003]. Retrieved from the Internet <URL: http://www.cambridgescientificinc.com>.

Carrino, John A., Roxanne Chan and Alexander R. Vaccaro, "Vertebral Augmentation: Vertebroplasty and Kyphoplasty", Seminars in Roentgenology, vol. 39, No. 1 (Jan. 2004): pp. 68-84.

Cheng, B.C., Ph.D., Biomechanical pullout strength and histology of Plasmapore Registered XP coated implants: Ovine multi time point survival study. Aesculap Implant Systems, LLC, 2013, 12 pages.

Chiang, "Biomechanical Comparison of Instrumented Posterior Lumbar Interbody Fusion with One or Two Cages by Finite Element Analysis", Spine, Sep. 2006, pp. E682-E689, vol. 31(19), Lippincott Williams & Wilkins, Inc.

(56) References Cited

OTHER PUBLICATIONS

Chin, "Early Results of the Triage Medical Percutaneous Transfacet Pedicular Bone-LOK Compression Device for Lumbar Fusion", Accessed online Jul. 10, 2017, 10 pages.
Edeland, H.G., "Some Additional Suggestions For An Intervertebral Disc Prosthesis", J of Bio Medical Engr., vol. 7(1) pp. 57-62, Jan. 1985.
European Search Report EP03253921 dated Nov. 13, 2003, 4 pages.
Flemming et al., Monoclonal anitbody against adult marrow-derived mesenchymal stem cells recognizes developing vasculature in embryonic human skin. Developmental Dynamics. 1998;212:119-132.
Folman, Posterior Lumbar Interbody Fusion for Degenerative Disc Disease Using a Minimally Invasive B-Twin Expandable Spinal Spacer, Journal of Spinal Disorders & Techniques, 2003, pp. 455-460, vol. 16(5).
Fuchs, "The use of an interspinous implant in conjuction with a graded facetectomy procedure", Spine vol. 30, No. 11, pp. 1266-1272, 2005.
Gore, "Technique of Cervical Interbody Fusion", Clinical Orthopaedics and Related Research, Sep. 1984, pp. 191-195, No. 188.
Gray's Anatomy, Crown Publishers, Inc., 1977, pp. 33-54.
Ha et al. (Topographical characterization and microstructural interface analysis of vacuum-plasma-sprayed titanium and hydroxyapatite coatings on carbon fiber-reinforced poly(etheretherketone), Journal of Materials Science: Materials in Science 9 (1997), pp. 891-896.
Haas, Norbert P., New Products from AO Development [online], May 2002 [retrieved on Oct. 14, 2003]. Retrieved from the Internet <URL: http://www.ao.asif.ch/development/pdf_tk_news_02.pdf>.
Hao et al., Investigation of nanocomposites based on semi-interpenetrating network of [L-poly (epsilon-caprolactone )]/[net-poly (epsilon-caprolactone)] and hydroxyapatite nanocrystals. Biomaterials. Apr. 2003;24(9): 1531-9.
Harsha et al., Tribo performance of polyaryletherketone composites, Polymer Testing (21) (2002) pp. 697-709.
Haynesworth et al., Cell surface antigens on human marrow-derived mesenchymal cells are detected by monoclonal antibodies. Bone. 1992;13(1):69-80.
Hitchon et al., Comparison of the biomechanics of hydroxyapatite and polymethylmethacrylate vertebroplasty in a cadaveric spinal compression fracture model. J Neurosurg. Oct. 2001;95(2 Suppl):215-20.
Hoogland et al., "Total Lumar Intervertebral Disc Replacement: Testing a New Articulating Space in Human Cadaver Spines-24 1", Annual ORS, Dallas, TX, Feb. 21-23, 1978, 8 pages.
Hunt, "Expandable Cage Placement Via a Posterolateral Approach in Lumbar Spine Reconstructions", Journal of Neurosurgery: Spine, Sep. 2006, pp. 271-274, vol. 5.
International Patent Application No. PCT /US2013/029014, International Search Report dated Jul. 1, 2013, 7 pages.
International Patent Application No. PCT/US2013/029014, International Search Report dated Jul. 1, 2013, 2 pages.
Iprenburg et al., "Transforaminal Endocopic Surgery in Lumbar Disc Herniation in an Economic crises—The Tessys Method", US Musculoskeletal, 2008, pp. 47-49.
Joshi, Ajeya P., M.D. and Paul A. Glazer, M.D., "Vertebroplasty: Current Concepts and Outlook for the Future", 2003, (5 pages), From: http://www.orthojournalhms.org/html/pdfs/manuscript-15.pdf.
Kambin et al., "Percutaneous Lateral Discectomy of the Lumbar Spine: A Preliminary Report", Clin. Orthop,: 1983, 174: 127-132.
Kandziora, Frank, et al., "Biomechanical Analysis of Biodegradable Interbody Fusion Cages Augmented with Poly (propylene Glycol-co-Fumaric Acid)," Spine, 27(15): 1644-1651 (2002).
King., "Internal Fixation for Lumbosacral Fusion", The Journal of Bone and Joint Surgery, J. Bone Joint Surg. Am., 1948; 30: 560-578.
Kotsias, A., Clinical trial of titanium-coated PEEL cages anterior cervical discectomy and fusion. [Klinishe Untersuching zum Einsatz von titanbeschichteten Polyetheretherketon—Implantaten bei der cervikalen interkorporalen fusion]. Doctoral thesis. Department of Medicine, Charite, University of Medicine Berlin, 2014, 73 pages. (German Tanguage document/Engl. summary).
Krbec, "Replacement of the Vertebral Body with an Expansion Implant (Synex)", Acta Chir Orthop Traumatol Cech, 2002, pp. 158-162, vol. 69(3).
Kroschwitz et al., eds., Hydrogels. Concise Encyclopedia of Polymer Science and Engineering. Wiley and Sons, pp. 458-459, 1990.
Lendlein et al., AB-polymer networks based on oligo(epsilon-caprolactone) segments showing shape-memory properties. Proc Natl Acad Sci US A. Jan. 30, 2001;98(3):842-7. Epub Jan. 23, 2001.
Link SB Charite Brochure—Intervertebral Prosthesis 1988, 29 pages.
Mahar et al., "Biomechanical Comparison of Novel Percutaneous Transfacet Device and a Traditional Posterior System for Single Level Fusion", Journal of Spinal Disorders & Techniques, Dec. 2006, vol. 19, No. 8, pp. 591-594.
Malberg. M.I., MD; Pimenta, L., MD; Millan, M.M., MD, 9th International Meeting on Advanced Spine Techniques, May 23-25, 2002, Montreux, Switzerland. Paper #54, Paper #60, and E-Poster#54, 5 pages.
McAfee et al., Minimally invasive anterior retroperitoneal approach to the lumbar spine: Emphasis on the lateral BAK. Spine. 1998;23(13):1476-84.
Medco Forum, "Percutaneous Lumbar Fixation Via Perpos PLS System Interventional Spine", Sep. 2008, vol. 15, No. 37.
Medco Forum, "Percutaneous Lumbar Fixation via Perpos System From Interventional Spine", Oct. 2007, vol. 14, No. 49.
Mendez et al., Self-curing acrylic formulations containing PMMA/PCL composites: properties and antibiotic release behavior. J Biomed Mater Res. Jul. 2002;61 (1 ):66-74.
Morgenstern, "Transforaminal Endoscopic Stenosis Surgery—A Comparative Study of Laser and Reamed Foraminoplasty", in European Musculoskeletal Review, Issue 1, 2009.
Nguyen et al., Poly(Aryl-Ether-Ether-Ketone) and its Advanced Composites: A Review, Polymer Composites, Apr. 1987, vol. 8, No. 2, pp. 57-73.
Niosi, "Biomechanical Characterization of the three-dimentional kinematic behavior of the dynesys dynamic stabilization system: an in vitro study", Eur Spine J. (2006), 15: pp. 913-922.
Osteoset Registered DBM Pellets (Important Medical Information) [online], Nov. 2002 [retrieved on Oct. 14, 2003]. Retrieved from the Internet <URL: http://www.wmt.com/Literature>.
Polikeit, "The Importance of the Endplate for Interbody Cages in the Lumbar Spine", Eur. Spine J., 2003, pp. 556-561, vol. 12.
Porocoat(R) Porous Coating, 1 Page, https://emea.depuysynthese.com/hcp/hip/products/qs/porocoat-porous-coatingemea Accessed on Jul. 31, 2017.
CN Office Action dated Apr. 24, 2020 for CN Application No. 201780040910.
ProMap TM EMG Navigation Probe. Technical Brochure Spineology Inc, Dated May 2009.
Regan et al., Endoscopic thoracic fusion cage. Atlas of Endoscopic Spine Surgery. Quality Medical Publishing, Inc. 1995;350-354.
Shin, "Posterior Lumbar Interbody Fusion via a Unilateral Approach", Yonsei Medical Journal, 2006, pp. 319-325, vol. 47(3).
Siddiqui, "The Positional Magnetic Resonance Imaging Changes in the Lumbar Spine Following Insertion of a Novel Interspinous Process Distraction Device", Spine, vol. 30, No. 23, pp. 2677-2682, 2005.
Slivka et al., In vitro compression testing of fiber-reinforced, bioabsorbable, porous implants. Synthetic Bioabsorbable Polymers for Implants. STP1396, pp. 124-135, ATSM International, Jul. 2000.
Sonic Accelerated Fracture Healing System/Exogen 3000. Premarket Approval. U.S. Food & Drug Administration. Date believed to be May 10, 2000. Retrieved Jul. 23, 2012 from <http://www.accessdata.fda.gov/scripts/cdrh/cfdocs/cfPMA/pma.cfm2id-14736#>. 4 pages, 2012.
Spine Solutions Brochure—Prodisc 2001, 16 pages.
Stewart et al., Co-expression of the stro-1 anitgen and alkaline phosphatase in cultures of human bone and marrow cells. ASBMR 18th Annual Meeting. Bath Institute for Rheumatic Diseases, Bath, Avon, UK. Abstract No. P208, p. S142, 1996.

(56) References Cited

OTHER PUBLICATIONS

Talwar "Insertion loads of the X Stop interspinous process distraction system designed to treat neurogenic intermittent claudication", Eur Spine J. (2006) 15: pp. 908-912.
Timmer et al., In vitro degradation of polymeric networks of polypropylene fumarate) and the crosslinking macromer polypropylene fumarate)-diacrylate. Biomaterials. Feb. 2003;24(4):571-7.
U.S. Appl. No. 60/424,055, Method and apparatus for spinal fixation, filed Nov. 5, 2002.
U.S. Appl. No. 60/794,171, Method and apparatus for spinal fixation, filed Apr. 21, 2006.
U.S. Appl. No. 60/397,588, Method and apparatus for spinal fixation, filed Jul. 19, 2002.
U.S. Appl. No. 61/675,975, Expandable Implant, filed Jul. 26, 2012.
U.S. Appl. No. 60/942,998, Method and Apparatus for Spinal Stabilization, filed Jun. 8, 2007.
United States Disctrict Court, Central District of California, Case No. 1:10-CV-00849-LPS, *Nuvasive, Inc.*, vs., *Globus Medical, Inc.*, Videotaped Deposition of: Luiz Pimenta, M.D., May 9, 2012, 20 pages.
U.S. Appl. No. 14/640,220, filed Mar. 6, 2015, entitled Expandable Intervertebral Implant.
U.S. Appl. No. 14/685,358, filed Apr. 13, 2015, entitled Expandable Intervertebral Implant.
U.S. Appl. No. 14/685,402, filed Apr. 13, 2015, entitled Expandable Intervertebral Implant.
U.S. Appl. No. 14/790,866, filed Jul. 2, 2015, entitled Expandable Implant.
Walsh et al., Preparation of porous composite implant materials by in situ polymerization of porous apatite containing epsilon-caprolactone or methyl methacrylate Biomaterials. Jun. 2001;22(11):1205-12.
Zimmer.com, Longer BAK/L Sterile Interbody Fusion Devices. Date believed to be 1997. Product Data Sheet.Zimmer. Retrieved Jul. 23, 2012 from <http:/catalog.zimmer.com/contenUzpc/products/600/600/620/S20/S045.html>, 2 pages.

Zucherman, "A Multicenter, Prospective, Randomized Trial Evaluating the X Stop Interspinous Process Decompression System for the Treatment of Neurogenic Intermittent Claudication", Spine, vol. 30, No. 12, pp. 1351-1358, 2005.
US 5,545,827, 10/1995, Aust (withdrawn)
Allcock, "Polyphosphazenes"; The Encyclopedia of Polymer Science; 1988; pp. 31-41; vol. 13; Wiley Intersciences, John Wiley & Sons.
Cohn, "Biodegradable PEO/PLA Block Copolymers"; Journal of Biomedical Materials Research; 1988; pp. 993-1009; vol. 22; John Wiley & Sons, Inc.
Cohn, "Polymer Preprints"; Journal of Biomaterials Research; 1989; p. 498; Biomaterials Research Labortatory, Casali Institute of Applied Chemistry, Israel.
Heller, "Poly (Otrho Esters)"; Handbook of Biodegradable Polymers; edited by Domb; et al; Hardwood Academic Press; 1997; pp. 99-118.
Japanese Office Action for Application No. 2013-542047, dated Sep. 8, 2015 (12 pages).
Japanese Office Action for Application No. 2016-135826, dated Jun. 6, 2017, (7 pages).
Kemnitzer, "Degradable Polymers Derived From the Amino Acid L-Tyrosine"; 1997; pp. 251-272; edited by Domb, et. al., Hardwood Academic Press.
Khoo, "Minimally Invasive Correction of Grade I and II Isthmic Spondylolisthesis using AxiaLIF for L5/S1 Fusion", pp. 1-7, Rev B Sep. 15, 2008.
Khoo, Axilif address spongy from the caudal approach. Minimally Invasive Correction of Grage I and II Isthmic Spondylolisthesis using AsiaLiF for L5/S1 Fusion, pp. 45-0123 Rev B Sep. 15, 2008.
U.S. Appl. No. 61/009,546, filed Dec. 28, 2007 Rodgers.
U.S. Appl. No. 61/140,926, filed Dec. 26, 2008 Spann.
U.S. Appl. No. 61/178,315, filed May 14, 2009 Spann.
U.S. Appl. No. 62/950,180, filed Dec. 19, 2019, Spitler et al.
Vandorpe, "Biodegradable Polyphosphazenes for Biomedical Applications"; Handbook of Biodegradable Polymers; 1997; pp. 161-182; Hardwood Academic Press.

\* cited by examiner

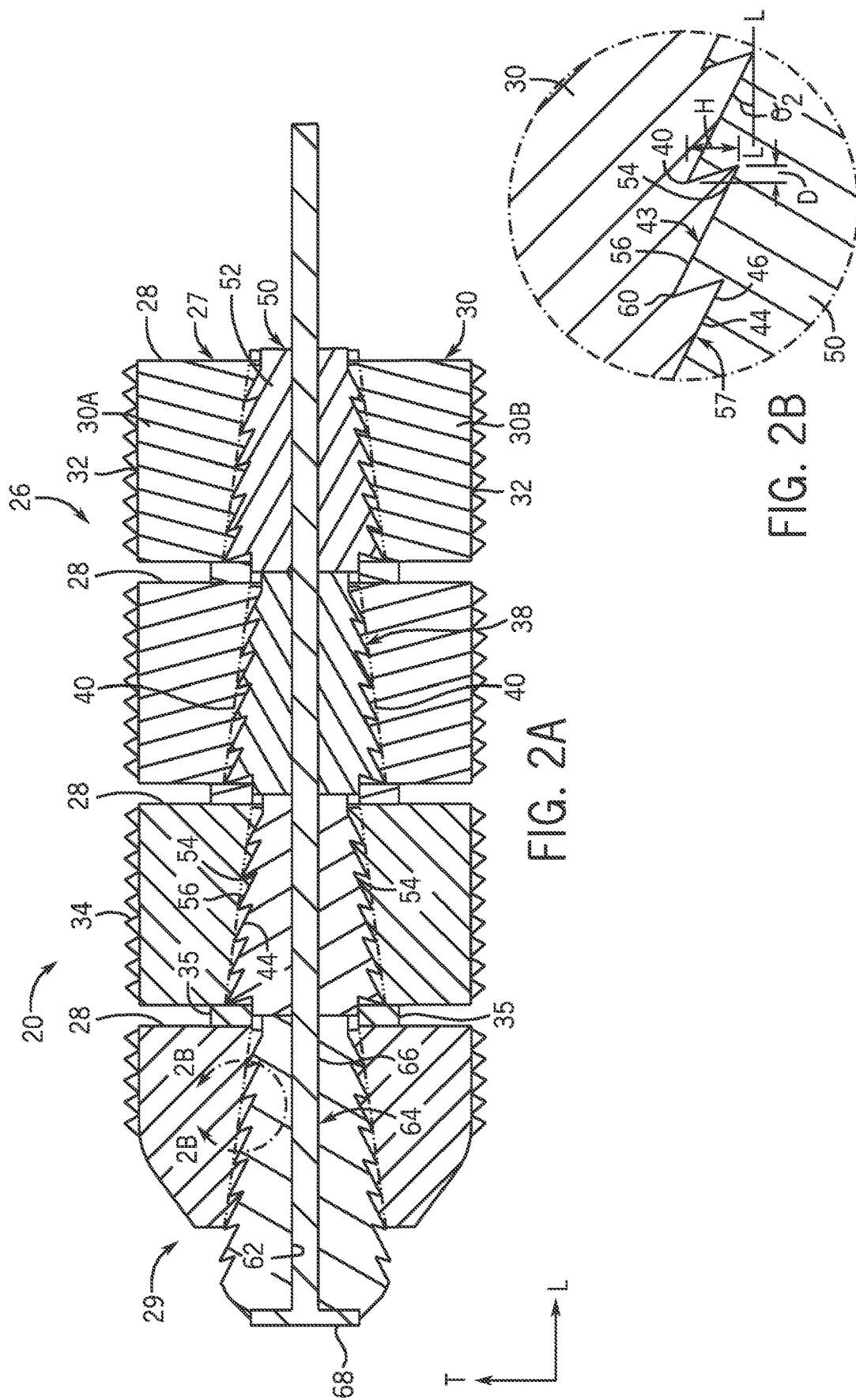

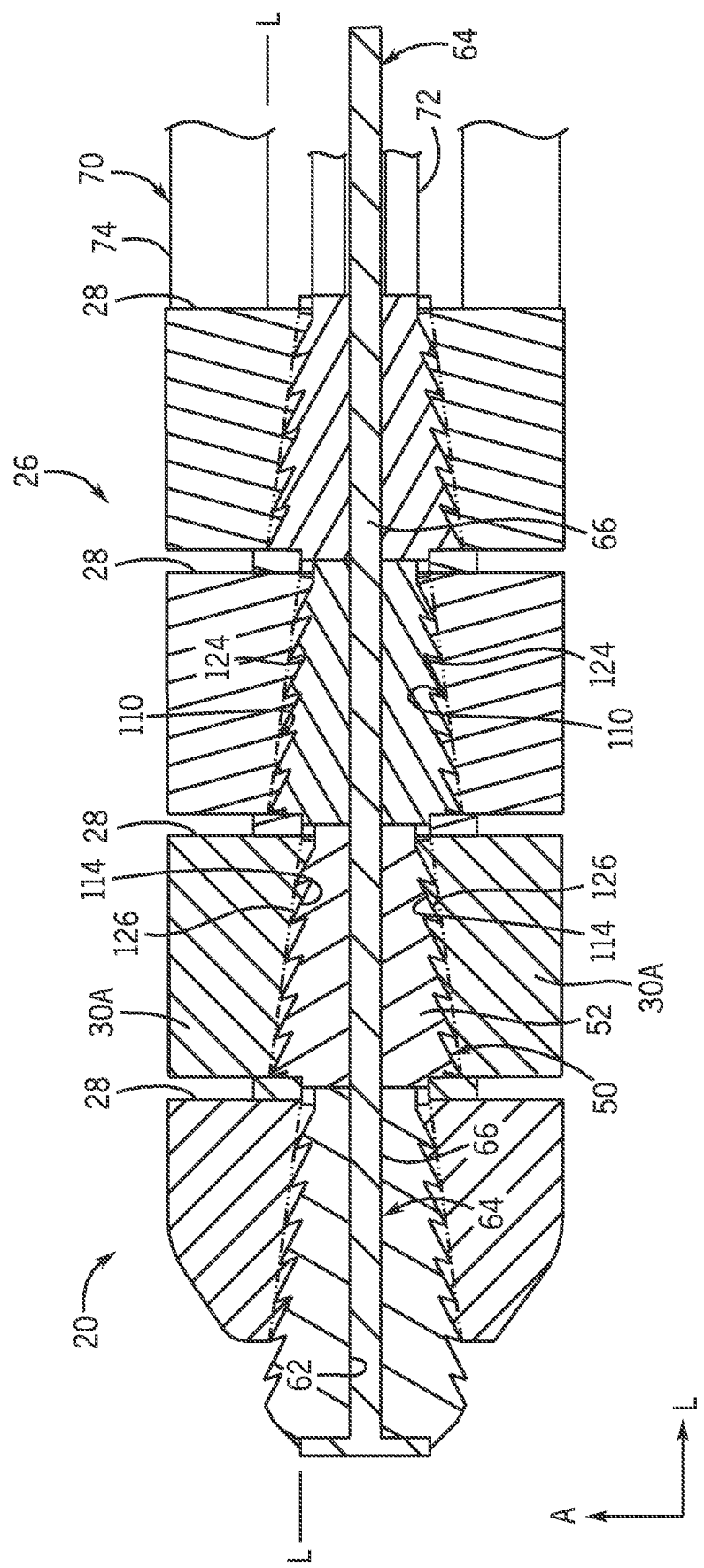

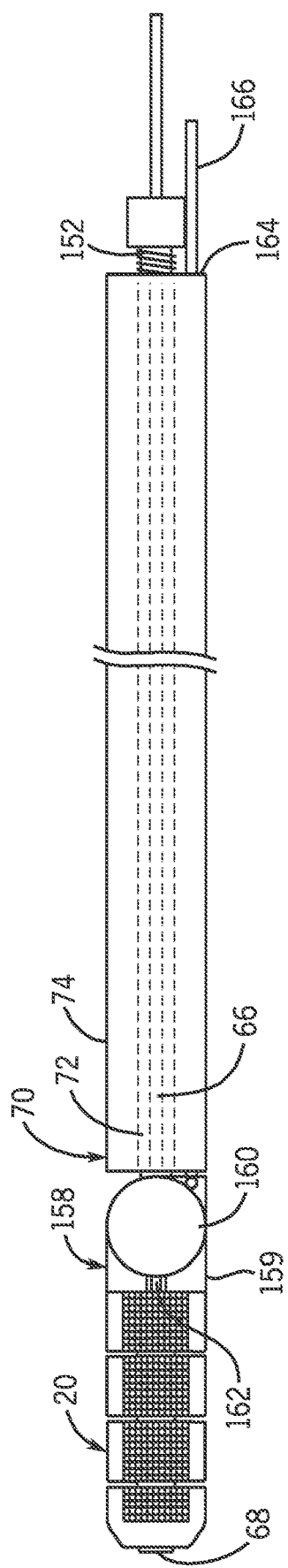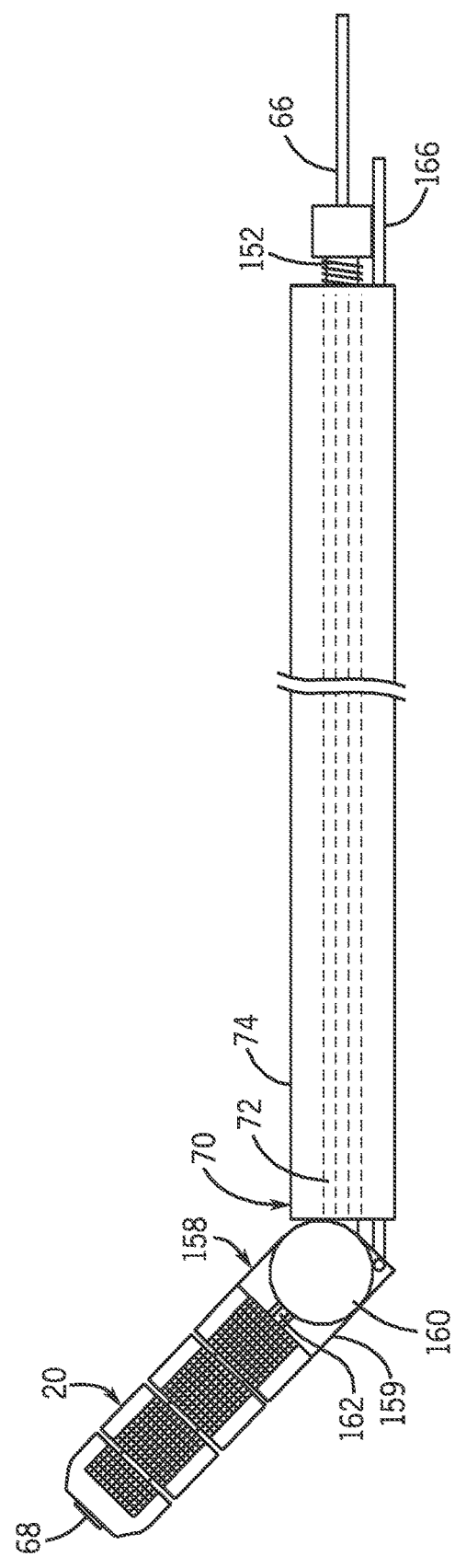
FIG. 18A
FIG. 18B

EXPANDABLE INTERVERTEBRAL IMPLANT

CROSS-REFERENCE TO RELATED APPLICATIONS

This is a continuation of U.S. patent application Ser. No. 16/593,430 filed Oct. 4, 2019, which is a continuation of U.S. patent application Ser. No. 15/926,247 filed Mar. 20, 2018, which is a continuation of U.S. patent application Ser. No. 15/235,160 filed Aug. 12, 2016, which is a continuation of U.S. patent application Ser. No. 14/565,611 filed Dec. 10, 2014, which is a continuation of U.S. patent application Ser. No. 12/936,466 filed Oct. 5, 2010 now issued as U.S. Pat. No. 8,936,641, which is a National Stage of International Application Serial No. PCT/US2009/039501, filed Apr. 3, 2009, which claims the benefit of U.S. Provisional Application Ser. No. 61/042,724, filed on Apr. 5, 2008, the disclosure of each of which is hereby incorporated by reference as if set forth in its entirety herein.

FIELD OF THE INVENTION

This disclosure relates generally to intervertebral implants, and in particular relates to an intervertebral implant that can expand to create a desired spacing and/or angular orientation of adjacent vertebrae.

BACKGROUND OF THE INVENTION

Degenerative disc disease or degeneration of a vertebral body often results in a loss of disc height, which in turn can cause facet and nerve impingement, among other things. One standard of care is to replace the damaged intervertebral disc with an intervertebral implant or a damaged portion or an entire vertebral body with an intervertebral implant.

Thus, an intervertebral implant may be inserted into the intervertebral disc space of two adjacent vertebral bodies or into the space created by removal of portions of, or the entire, vertebral body after removal of damaged portions of the spine. Preferably, the intervertebral implant restores the spine, as much as possible, to a natural state. That is, the implant preferably restores the original height of the intervertebral disc and thus the original distance between the two adjacent vertebral bodies or vertebral bodies in various levels of the spine. These implants are sized and shaped to fill at least the physiological height between the vertebral bodies and are inserted through a relatively narrow and small incision with nerves and vascular structure proximate sides of the incision. Accordingly, it is advantageous to develop an implant that may be inserted in a reduced size or configuration and expanded when positioned between the vertebrae to minimize the required incision and limit the potential for the implant to contact the neural and vascular structure during implantation.

It is desirable to construct an intervertebral implant that restores the spine to its natural state, is relatively compact during insertion and may be expanded when positioned between adjacent vertebrae. It is also desirable to construct an expandable intervertebral implant that may be inserted and expanded utilizing the same instrument.

BRIEF SUMMARY OF THE INVENTION

The following Summary is provided to introduce a selection of concepts in a simplified form that are further described below in the Detailed Description of Illustrative Embodiments. This Summary is not intended to identify key features or essential features of the invention, nor is it intended to be used to limit the scope of the invention. Reference is made to the claims for that purpose.

Certain embodiments are directed to an expandable intervertebral implant for insertion into an intervertebral disc space and expandable from an initial position to an expanded position. The expandable intervertebral implant includes a linkage that includes a plurality of links connected in a longitudinal direction. Each link includes an outer sleeve having a first outer sleeve portion and a second outer sleeve portion that is movable with respect to the first outer sleeve portion. The second outer sleeve portion defines a first engagement surface that is sloped with respect to the longitudinal direction. Each link further includes an inner core disposed between the first and second outer sleeve portions. The inner core defines a second engagement surface that is sloped with respect to the longitudinal direction, wherein the second engagement surface abuts the first engagement surface. Relative movement between the inner core and the second outer sleeve portion along the longitudinal direction causes the first engagement surface to ride along the second engagement surface, thereby causing the second outer sleeve portion to deflect away from the first outer sleeve portion in a direction substantially perpendicular to the longitudinal direction.

Additional features and advantages will be made apparent from the following detailed description of illustrative embodiments with reference to the accompanying drawings.

BRIEF DESCRIPTION OF THE SEVERAL VIEWS OF THE DRAWINGS

The foregoing summary, as well as the following detailed description, is better understood when read in conjunction with the appended drawings. There is shown in the drawings example embodiments, in which like reference numerals correspond to like reference numerals throughout. The expandable intervertebral implant and related methods are not limited to the specific embodiments and methods disclosed, and reference is made to the claims for that purpose.

FIG. 2A is a sectional side elevation view of the expandable intervertebral implant illustrated in FIG. 1 constructed as a linkage that includes a plurality of expandable intervertebral links in accordance with one embodiment, wherein the implant is in a first contracted position;

FIG. 2B is an enlarged portion of the expandable intervertebral implant illustrated in FIG. 2A;

FIG. 15A is a top sectional view of an expandable intervertebral implant similar to that illustrated in FIG. 6, but further configured for lateral expansion in accordance with an alternative embodiment, wherein the expandable intervertebral implant is shown in a laterally contracted position;

FIG. 18A is a top plan view of an expandable intervertebral implant coupled to an angulated insertion device constructed in accordance with an alternative embodiment;

FIG. 18B is a top plan view of the expandable intervertebral implant coupled to the angulated insertion device illustrated in FIG. 18A, showing the insertion device in an angulated position;

DETAILED DESCRIPTION OF THE INVENTION

Figure 1A:
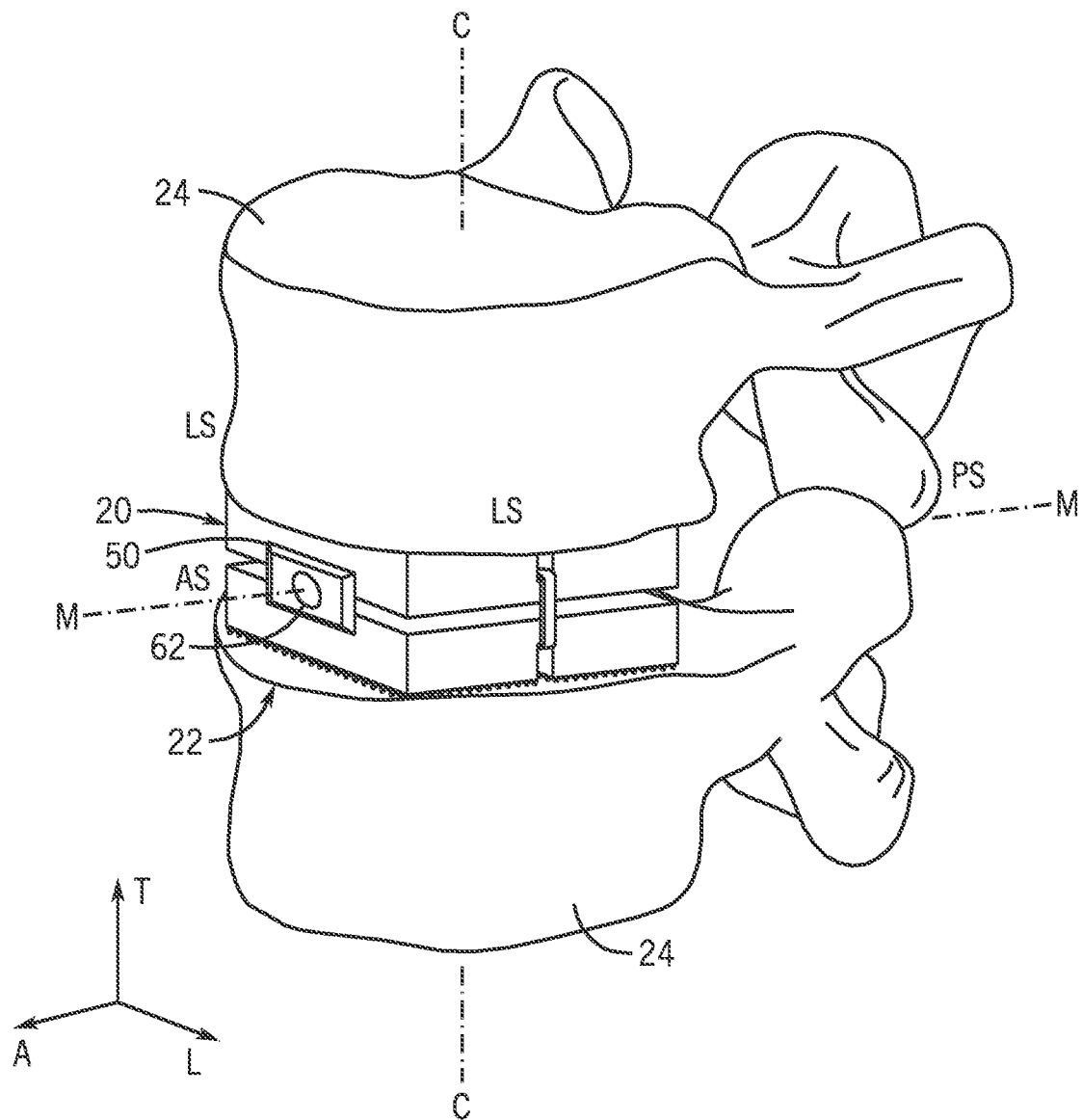
FIG. 1A is a perspective view of an expandable intervertebral implant constructed in accordance with one embodiment installed in an intervertebral space.

Certain terminology is used in the following description for convenience only and is not limiting. The words "right", "left", "lower" and "upper" designate directions in the drawings to which reference is made. The words "inwardly" or "distally" and "outwardly" or "proximally" refer to directions toward and away from, respectively, the geometric center of the expandable implant, instruments and related parts thereof. The words, "anterior", "posterior", "superior," "inferior" and related words and/or phrases designate preferred positions and orientations in the human body to which reference is made and are not meant to be limiting. The terminology includes the above-listed words, derivatives thereof and words of similar import.

Referring to FIG. 1A, an expandable intervertebral implant 20 is shown installed into an intervertebral disc space 22 defined by a pair of adjacent, or neighboring, upper and lower vertebrae 24. The expandable intervertebral implant 20 can be configured to fuse with the vertebrae 24. The vertebrae 24 can be lumbar vertebrae that define an anterior side AS, an opposing posterior side PS. The vertebrae 24 further define opposing lateral sides LS that are disposed on opposing sides of a central medial axis M-M that extends along a mediolateral direction. The vertebrae 24 are illustrated as being spaced along a caudocranial axis C-C. The expandable intervertebral implant 20 extends generally along a longitudinal direction L, a lateral direction A, and a transverse direction T.

Various structure is therefore described as extending horizontally along a longitudinal direction "L" and lateral direction "A", and vertically along a transverse direction "T". The housing is elongate in the longitudinal direction L. Unless otherwise specified herein, the terms "lateral," "longitudinal," and "transverse" are used to describe the orthogonal directional components of various components.

The directional terms "inboard" and "inner," "outboard" and "outer," and derivatives thereof are used herein with respect to a given apparatus to refer to directions along the directional component toward and away from the geometric center of the apparatus.

It should be appreciated that while the longitudinal and lateral directions are illustrated as extending along a horizontal plane, and that the transverse direction is illustrated as extending along a vertical plane, the planes that encompass the various directions may differ during use. Accordingly, the directional terms "vertical" and "horizontal" are used to describe the expandable intervertebral implant 20 and its components as illustrated merely for the purposes of clarity and illustration.

In the illustrated embodiment, the longitudinal direction L extends in an anteroposterior direction, the lateral direction A extends in the mediolateral direction, and the transverse direction T extends in the caudocranial direction. It should be appreciated, however, that the directions defined by the expandable intervertebral implant 20 could alternatively be oriented at any desirable angle between 0° and 180° with respect to the various directions defined by the vertebrae 24. For instance, the longitudinal and lateral directions of the implant could be oriented at any desirable angle between 0° and 180° with respect to the mediolateral and anteroposterior directions. As will become appreciated from the description below, the expandable intervertebral implant 20 can be inserted into the disc space 22 in an anterior direction, a posterior direction, or any alternative direction between 0° and 180° with respect to the anterior and posterior sides.

Figure 1B:
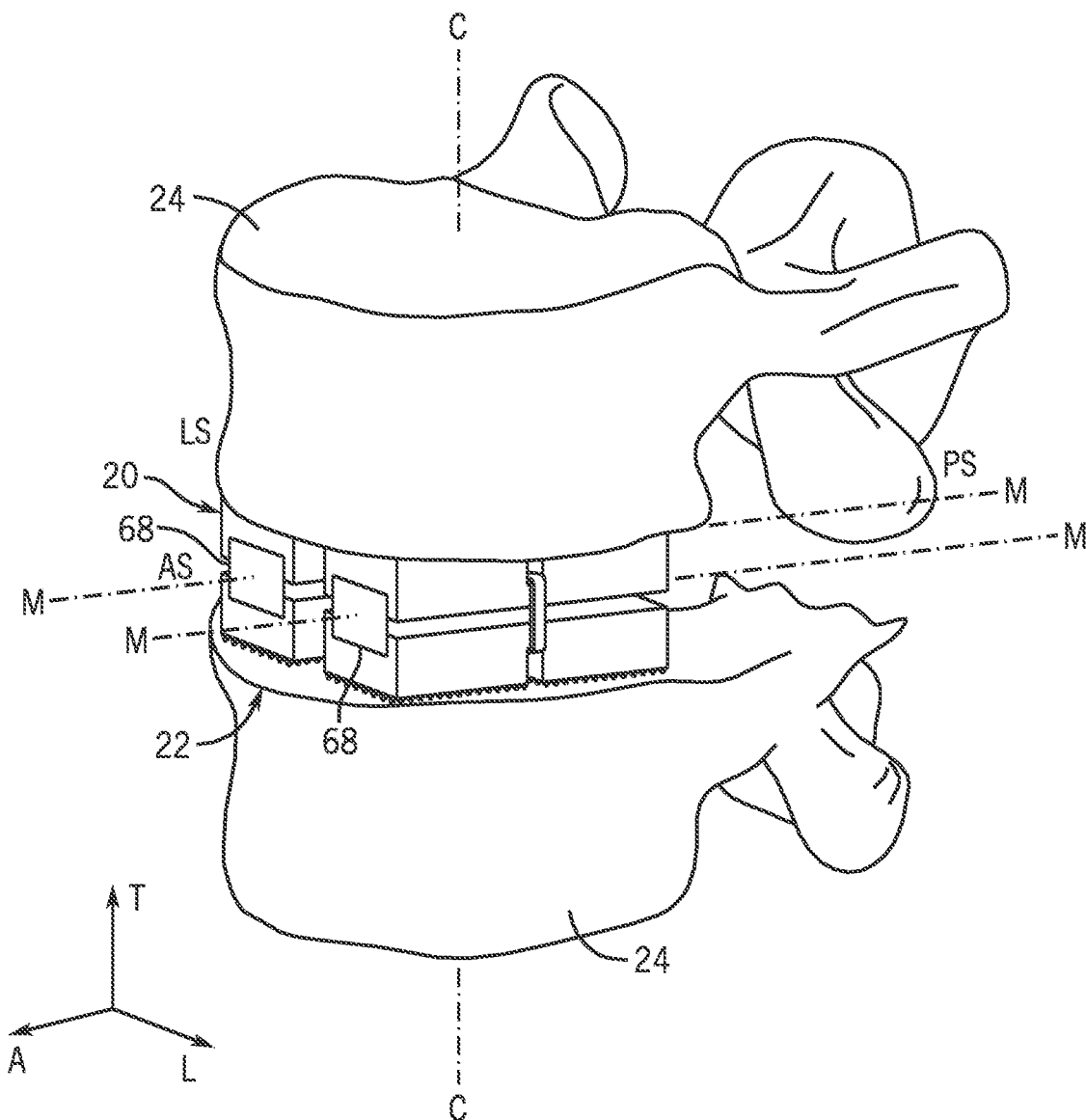
FIG. 1B is a perspective view similar to FIG. 1A, but with the intervertebral implant installed in the intervertebral space in accordance with an alternative embodiment

For instance, FIG. 1B illustrates the expandable intervertebral implant 20 installed into the intervertebral space 22 in an orientation that is 180° rotated with respect to the orientation illustrated in FIG. 1A. In this regard, it should be appreciated that the implant 20 can be inserted into the intervertebral space 22 from the anterior or posterior direction, or a direction that is angularly offset from the anterior or posterior direction. When inserting the implant 20 into the intervertebral space 22, for instance from the posterior, posterior anatomical elements can be removed, such as ligaments, a part or all of the lamina, the posterior arch, and some or all of the facet joints that are aligned with the vertebral space that receives the implant. While one implant 20 is illustrated as being inserted into the intervertebral space 22 in FIG. 1A, and a pair of implants 20 as being inserted into the intervertebral space 22 in FIG. 1B, any desired number of implants 20 can be inserted into a given intervertebral space as desired, such as between one and four implants. It should further be appreciated that one or more implants 20 can be installed into the intervertebral space 22 when performing a corpectomy or hemicorpectomy.

Figure 3A:
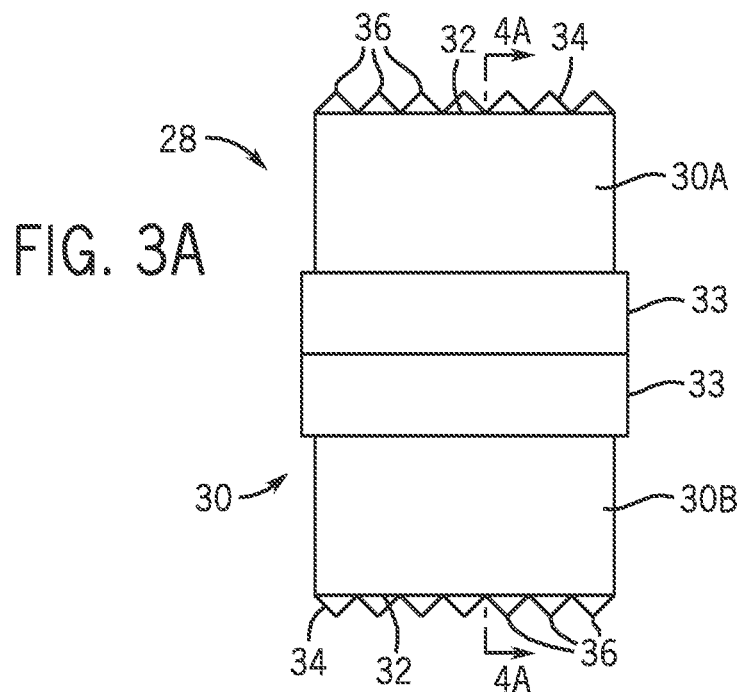
FIG. 3A is a side elevation view of an expandable intervertebral link of the intervertebral implant illustrated in FIG. 2A.
Figure 4A:
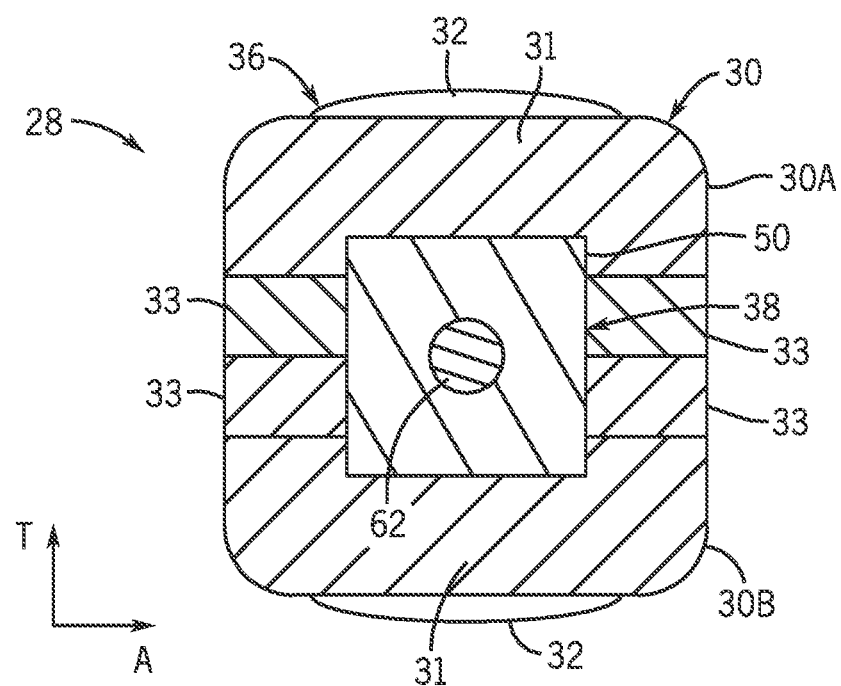
FIG. 4A is a sectional end elevation view of the expandable intervertebral link illustrated in FIG. 3A.

Referring now to FIGS. 2A, 3A, and 4A, the expandable intervertebral implant 20 can be provided as a longitudinally elongate linkage 26 that includes one or more links 28. The implant 20 can be made from any suitable biocompatible radiolucent or metallic material, such as titanium. The links 28 of the linkage 26 can be substantially similarly or identically constructed unless otherwise indicated. Each link includes an outer sleeve 30 formed from a pair of vertically opposing upper and lower outer sleeve portions 30A and 30B. The outer sleeve portions 30A and 30B each define a laterally elongate cross-beam 31 connected to a pair of outer legs 33 that each project transversely inward from the opposing outer lateral ends of the cross beams 31. Thus, the upper sleeve portion 30A includes legs 33 that project down from the laterally outer ends of the corresponding cross-beam 31, and the lower sleeve portion 30B includes legs 33 that project up from the laterally outer ends of the corresponding cross-beam 31. When the link 28 is in a first or initial contracted position, the inner transverse ends of the laterally aligned legs 33 can abut each other as illustrated so as to minimize the height of the implant 20 prior to installation into the intervertebral space 22, or they can alternatively be spaced apart.

The cross-beams 31 can each define respective vertebral engagement surfaces 32, such that the vertebral engagement surface of the upper sleeve portion 30A is an upwardly-facing surface, and the vertebral engagement surface of the lower sleeve portion 30B is a downwardly-facing surface. Each vertebral engagement surface 32 is configured to abut the corresponding upper and lower adjacent vertebrae 24.

Figure 3B:
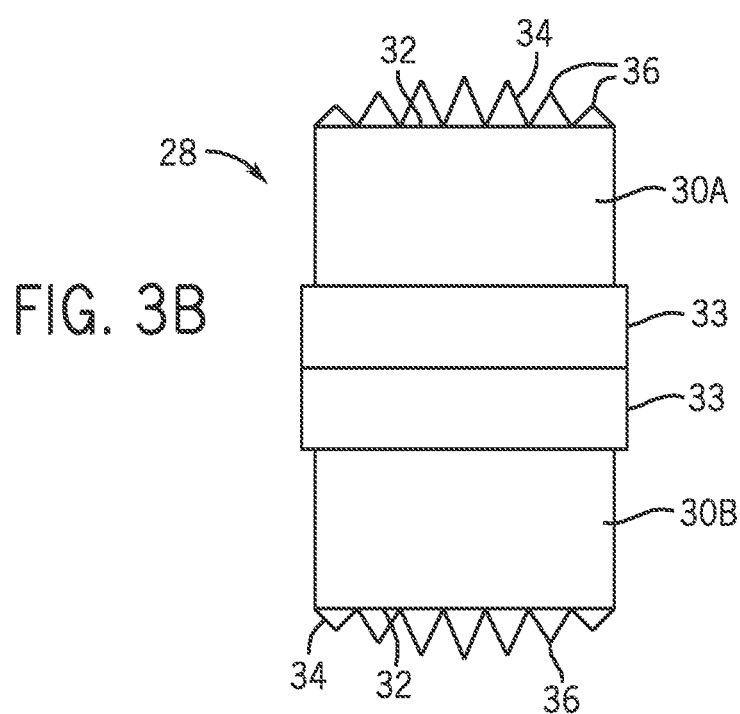
FIG. 3B is a side elevation view of the expandable intervertebral link similar to FIG. 3A, but constructed in accordance with an alternative embodiment.

Each outer sleeve portion 30A and 30B can include a plurality of teeth 34 projecting transversely out from the respective vertebral engagement surfaces 32. The teeth 34 can be laterally elongate, and can be arranged as a plurality of longitudinally spaced rows 36 as illustrated. The teeth 34 can have a substantially constant height across the plurality of rows 36, thereby defining a substantially linear toothed profile as illustrated in FIG. 3A. Alternatively, the teeth 34 can define a nonlinear profile across the rows. For instance, as illustrated in FIG. 3B, the rows of teeth of one or more links 28 can define a bowed profile, or a convexity, whereby the teeth 34 of the longitudinally middle rows have a height greater than the teeth of the longitudinally outer rows. The profile can be symmetrical or asymmetrical about a lateral axis passing through the longitudinal midpoint of the link 28.

Figure 4B:
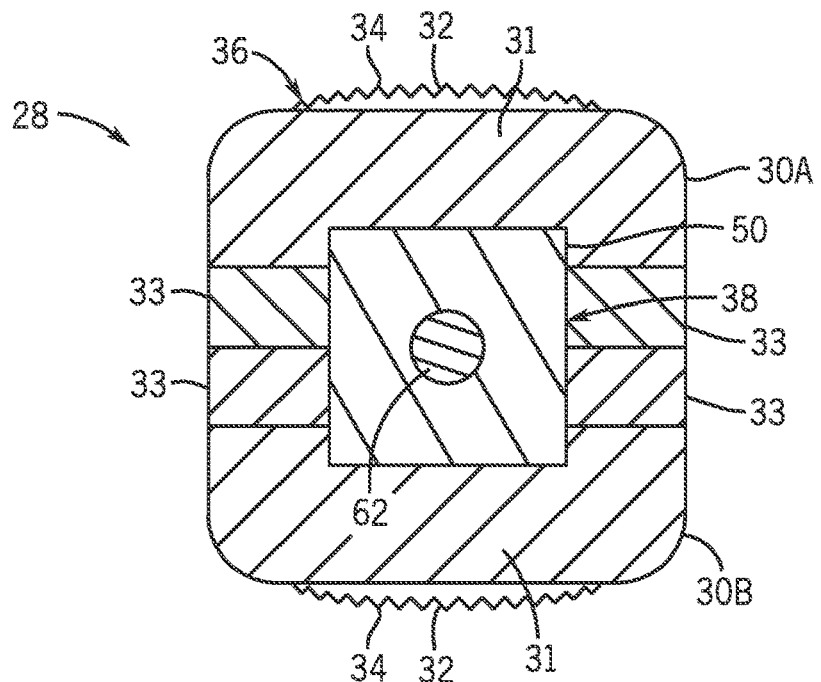
FIG. 4B is a sectional end elevation view of an expandable intervertebral link similar to that illustrated in FIG. 4A, but constructed in accordance with an alternative embodiment.

Alternatively or additionally, referring to FIG. 4A, one or more of the rows 36 of teeth 34, up to all of the rows of teeth, can be bowed along the lateral direction, such that the laterally middle portions of the teeth 34 have a height that is greater than the laterally outer portions of the teeth. The profile can be symmetrical or asymmetrical about a longitudinal axis passing through the lateral midpoint of the link 28. Thus, the teeth 34 can define a profile that is convex, or bowed, along more than one direction. While the teeth 34 are shown as being laterally elongate, it should be appreciated that the teeth 34 can alternatively be discontinuous in a lateral direction across the vertebral engagement surfaces 32 in a lateral direction. For instance, referring to FIG. 4B, a second plurality of teeth 34 can project out from the vertebral engagement surfaces 32 along the lateral direction. Thus each row 36 may include one or more teeth 34 so as to form an array of laterally spaced and longitudinally spaced teeth 34 along the vertebral engagement surfaces 32. The teeth 34 can be in substantial vertical alignment along a lateral axis, or can be bowed as shown in FIG. 4B to define a convex profile along the lateral direction such that laterally central teeth 34 have a height greater than that of the laterally outer teeth of a given row 36. Alternatively or additionally, the teeth 34 can be bowed as shown in FIG. 3B to define a convex profile along the longitudinal direction.

Figure 3C:
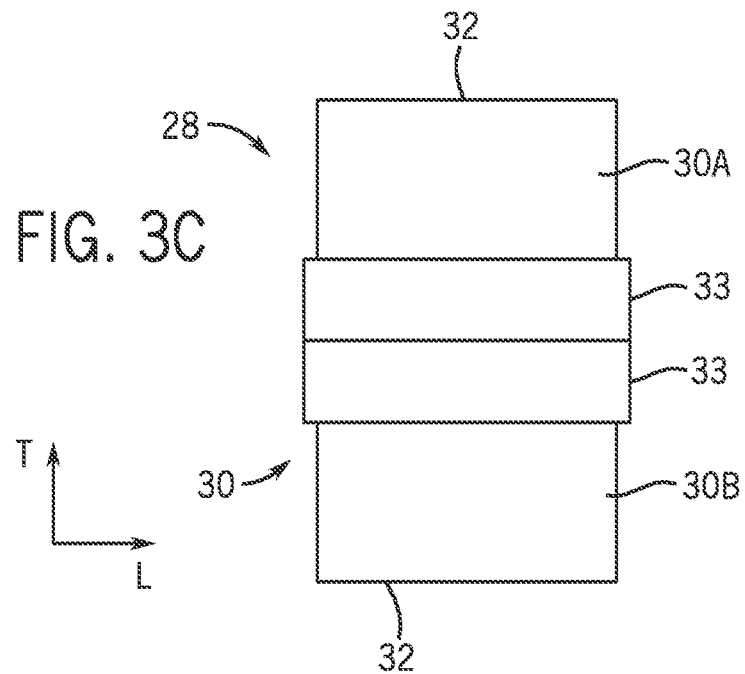
FIG. 3C is a side elevation view of the expandable intervertebral link similar to FIG. 3A, but constructed in accordance with another alternative embodiment.

The teeth 34 can assist in roughening the vertebral surface to assist in fusing the expandable intervertebral implant to the adjacent vertebrae, can provide a surface that grips against the vertebrae, and can also define an increased surface area that fuses with the adjacent vertebrae with respect to a flat vertebral engagement surface. Alternatively, one or both of the opposing vertebral engagement surfaces 32 can be substantially smooth, or non-toothed, along both the lateral and longitudinal directions, as illustrated in FIG. 3C. The smooth surface can extend substantially along a longitudinal-lateral plane, or can be bowed in either or both of the lateral and longitudinal directions.

With continuing reference to FIG. 2A, the linkage 26 can include one or more links 28, such as a plurality of adjoined links 28 as illustrated. Each link 28 can include a lateral cross beam 31 and a pair of opposing transverse legs 33 in the manner described above. Each link 28 can define a generally rectangular or square with straight or curved corners, edges, and surfaces, or any suitable alternative geometric shape. The linkage 26 defines a longitudinal front end 27 and an opposing longitudinal rear end 29. The rear end 29 of the linkage 26 can be geometrically configured for insertion into the intervertebral disc space 22. For instance, the cross beams of the link 28 disposed at the rear end 29 of the linkage can be curved transversely inward along a direction from front end 27 toward the rear end 29, thereby providing a guide surface when inserting the implant 20 into the intervertebral disc space 22.

Adjacent links 28 can be integrally connected or can alternatively be discreetly fastened to each other at a coupling location using any suitable mechanical or adhesive coupling member. For instance, a coupling member 35 can project longitudinally out from each leg 33 of adjacent links 28 toward the adjacent link 28, such that a coupling member 35 of the upper sleeve portion 30A of one link 28 is attached to a corresponding coupling member 35 of the upper sleeve portion 30A of an adjacent link 28. Likewise, a coupling member 35 of the lower sleeve portion 30B of one link 28 is attached to a corresponding coupling member 35 of the lower sleeve portion 30B of an adjacent link 28. The coupling members 35 can be flexible or rigid, and can be integrally formed with, or discreetly connected to, the corresponding legs 33. The linkage 26 can include any number of links 28 as desired, such that the upper sleeve portions 30A of each link 28 are connected, and the lower sleeve portions 30B of each link 28 are connected.

Figure 5:
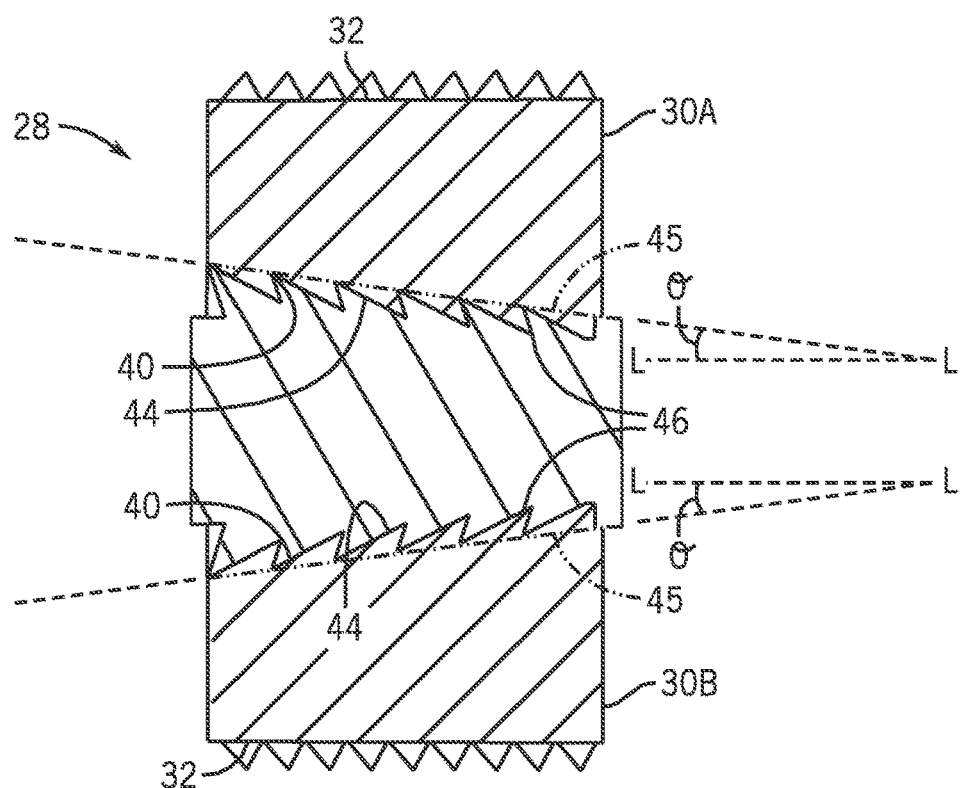
FIG. 5 is a sectional side elevation view of the expandable intervertebral link illustrated in FIG. 2A.

Referring now to FIGS. 2A and 5, the cross beam 31 of each outer sleeve portion 30A and 30B defines an outer vertebral engagement surface 32 as described above, and further defines an opposing transverse inner engagement surface 40 that extends laterally between the opposing transverse legs 33. The inner engagement surface 40 is sloped vertically so as to define an angle θ with respect to a longitudinal axis L-L that can be between 0° and 90°, for instance between about 10° and about 50°, such that the engagement surface 40 of each outer sleeve portion slopes transversely in along a longitudinal direction from the rear end 29 toward the front end 27 of the linkage 26. Thus, the inner engagement surface 40 of the upper sleeve portion 30A slopes vertically down along a longitudinal direction from the rear end 29 toward the front end 27, and the inner engagement surface 40 of the lower sleeve portion 30B slopes vertically up along a longitudinal direction from the rear end 29 toward the front end 27.

The engagement surfaces 40 of the upper sleeve portions 30A can define an angle greater θ or less than that of the engagement surfaces 40 of the lower sleeve portions 30B, thereby causing the upper sleeve portion 30A to expand at a higher or lower expansion rate, respectively, relative to the lower sleeve portion 30B. In this regard, it should be appreciated that the angle θ of one of the inner engagement surfaces 40 relative to the longitudinal axis L-L could be zero, while the angle θ of the other engagement surface 40 relative to the longitudinal axis L-L is non-zero, thereby causing only the outer sleeve portion of the other engagement surface to expand during operation.

The inner engagement surfaces 40 of each link 28 can be aligned with, and extend parallel to, the engagement surfaces 40 of the other links 28 of the linkage 26. Thus, the outer sleeve 30 of each link 28 can extend transversely a distance at its front end greater than at its rear end. Each link 28 can further include an engagement member as one or more projections or that extends transversely in from the engagement surfaces 40. The projections can be in the form of ridges, teeth, or like structure that is configured to mate with a complementary structure to fixes the implant in an expanded position. In the illustrated embodiment, the projections are shown as reverse angled teeth 44 that project transversely in from the engagement surface 40. Thus, for the purposes of description, the engagement member, or one or more projections, is referred to herein as teeth.

The teeth 44 project down from the engagement surface 40 of the upper sleeve portion 30A, and teeth project up from the engagement surface 40 of the lower sleeve portion 30B. The teeth 44 can define a root end 45 that is substantially in-line with the corresponding engagement surfaces 40, and triangular tips 46 that are transversely offset from the engagement surface. Adjacent tips 46 can be spaced apart any desired distance, such as between about 0.5 mm and about 5 mm. The teeth 44 of each link 28 can be substantially identically sized and shaped, such that a line connecting the tips 46 of adjacent teeth 40 extends parallel to the engagement surface 40. The outer sleeve portions 30A and 30B further define pockets 43 disposed between and defined by adjacent teeth 44. The pockets 43 thus have a size and shape substantially identical to the adjacent teeth 44 that define the pockets 43.

Each link 28 defines an internal void 38 that extends transversely between opposing cross beams 31 and laterally between opposing legs 33 of each outer sleeve portion 30A and 30B. The linkage 26 includes an inner core 50 that is disposed within the internal void 38 of each link 28, and is retained by the outer sleeve portions 30A and 30B. The inner core 50 can abut the transverse inner surfaces 40 of the cross beams 31 such that, during operation, longitudinal movement of the inner core 50 relative to the outer sleeve 30 causes the outer sleeve 30 to expand in a first direction, such as the vertical direction (see FIG. 7) and alternatively or additionally a second direction perpendicular to the transverse or vertical direction, such as the horizontal direction (see FIGS. 15A-C).

In the embodiment illustrated in FIGS. 2A-2B, the inner core 50 includes a core body 52 that defines opposing lateral surfaces that can face or abut the legs 33 of the outer sleeve, and opposing transverse outer, or upper and lower, engagement surfaces 54. The portion of the inner core 50 disposed within one of the links 28 can be integrally connected or alternatively fastened to the portions of the inner core 50 that are disposed in the other links 28 of the linkage 26 using any suitable mechanical or adhesive fastening member.

When the inner core 50 is installed in the internal void 38 of the outer sleeve 30, the engagement surfaces 54 can mate with, or abut, the corresponding sloped engagement surfaces 40 of the outer sleeve portions 30A and 30B. The engagement surfaces 54 are thus transversely sloped with respect to the longitudinal axis L-L, and thus extend parallel to the corresponding engagement surfaces 40. The inner core 50 can further include an engagement member as one or more projections that extend transversely out from the engagement surfaces 54. The projections can be in the form of ridges, teeth, or like structure that is configured to mate with a complementary structure to fix the implant in an expanded position. In the illustrated embodiment, the projections are shown as reverse angled teeth 56 that project transversely out from the engagement surfaces 54. Thus, for the purposes of description, the engagement member, or one or more projections, is referred to herein as teeth 56.

The teeth 56 can be sized and shaped substantially identical with respect to teeth 44, so as to mate with teeth 44. The teeth 56 define a root end that is substantially in-line with the corresponding engagement surfaces 54, and triangular tips 60 that are transversely offset from the engagement surface. The teeth 56 are identically sized and shaped, such that a line connecting the tips 60 of adjacent teeth 56 extends parallel to the engagement surface 54. Thus, the teeth of the inner core 50 become transversely inwardly disposed along a direction from the rear of the link 28 toward the front of the link 28. The inner core body 52 further defines pockets 57 disposed between and defined by adjacent teeth 56. The pockets 57 thus have a size and shape substantially identical to the adjacent teeth 56 that define the pockets 57.

With continuing reference to FIG. 2B, the teeth 44 are sized and shaped to interlock with mating teeth 56, and reside in the pockets 57 defined between adjacent teeth 56. Likewise, the teeth 56 are sized and shaped to interlock with mating teeth 44, and reside in the pockets 43 defined between adjacent teeth 44. The teeth 44 and 56 can define a sawtooth shape that is undercut such that the tips 46 and 60 of interlocking teeth 44 and 56 overlap each other a distance D, which can be greater than 0 mm and less than or equal to 2 mm. Accordingly, a transverse compressive force applied to the link 28 causes the teeth 44 and 56 to cam along each other to an interlocked position, such that interference between the tip ends 46 and 60 resists vertical separation of the outer sleeve 30 from the inner core 50 during insertion of the implant 20 into the intervertebral space. Moreover, as the implant 20 is inserted into the disc space 22, the bodily tissue will apply a forward longitudinal force against the outer sleeve 30, thereby biasing the teeth 44 and 56 into their interlocked position, whereby motion of the core 50 relative to the outer sleeve 30 is permitted in the longitudinally forward direction, but prevented in a longitudinally rearward direction.

The opposing tips 46 and 60 of interlocking teeth 44 and 56 can be spaced a transverse distance so as to define a height H that can be within a range between 0 mm and about 3 mm. The teeth 44 and 56 can further define an angle θ2 between about 10° and about 50° with respect to the longitudinal axis L-L.

Figure 6:
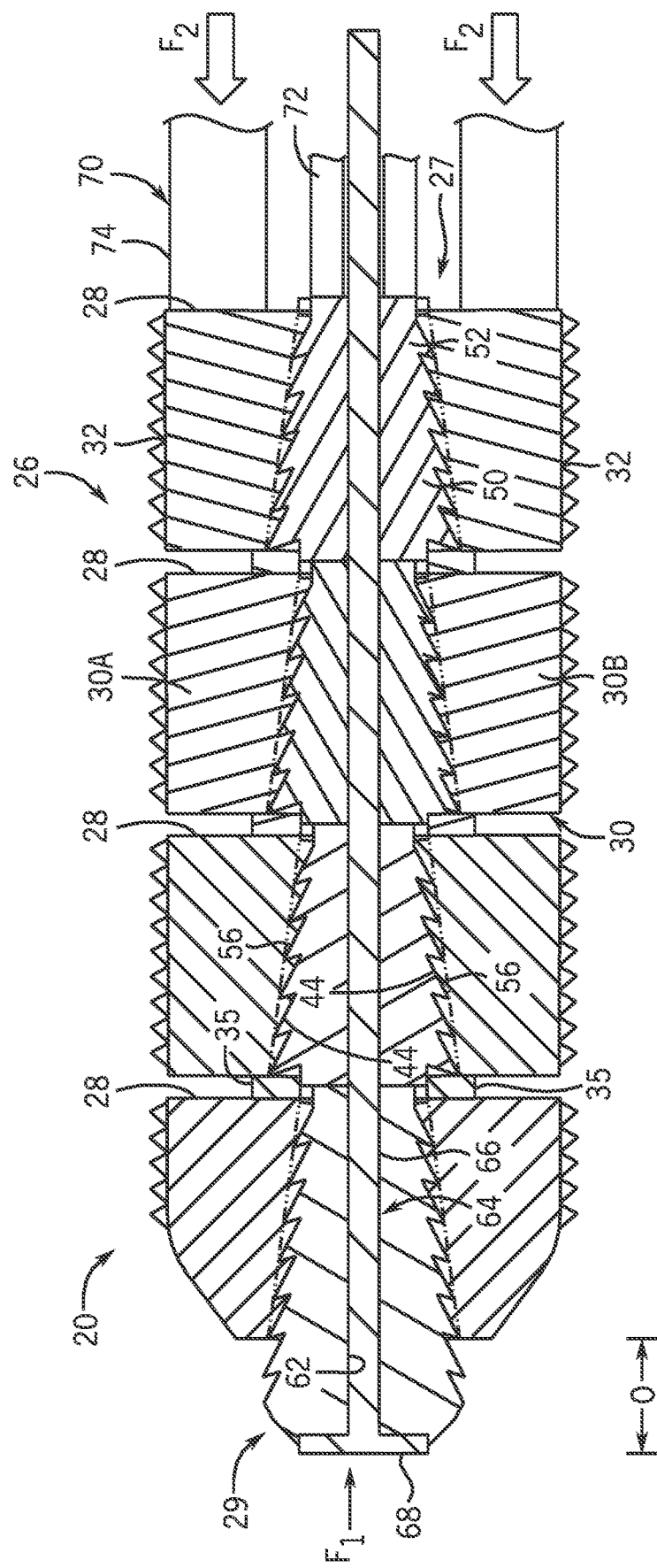
FIG. 6 is a sectional side elevation view of the expandable intervertebral implant illustrated in FIG. 5A, connected to an insertion device.

Referring now to FIG. 6, the linkage 26 can be coupled to an insertion tool 70, which includes a biasing member 64, an inner holding sleeve 72, and an outer holding sleeve 74. The biasing member 64 is operable to move the inner core member 50 longitudinally forward relative to the outer sleeve 30. In the illustrated embodiment, the inner core body 52 defines an internal longitudinally elongate bore 62 that is sized and shaped to receive the biasing member 64, which can be provided as a longitudinally extending rod or wire 66 connected to a transverse stopper 68 at one longitudinal end of the wire 66. The wire 64 can be made from vitalium, titanium, or the like. The stopper 68 is sized and shaped to abut the rear surface of the inner core 50, but not the outer sleeve, of the rearmost link 28, and the wire 66 can extend through the bore 62 of all inner core bodies 52 along the linkage 26, and project forward from the front end 27 of the linkage. The wire 66 can be held in place inside the bore 62 by an interference fit or any suitable fixation mechanism.

The inner annular holding sleeve 72 surrounds the wire 66 at a location forward from the front end 27 of the linkage 26, and can guide the wire 66 during operation. The wire 66 can be pulled in a longitudinal forward direction relative to the inner holding sleeve 72 such that the inner holding sleeve 72 abuts the front end of the core body 52 of the front-most link. The engagement of the inner holding sleeve 72 and the core body 52 allows a user to maintain control of the position of the implant 20 during insertion into the intervertebral space 22 as tension is applied to the wire 66.

The outer annular holding sleeve 74 is configured to abut the front end of the forwardmost outer sleeve 30 at a location that is out of transverse alignment with the core body 52. The outer holding sleeve 74 provides reciprocal biasing member that is operable to provide a biasing force that is equal and opposite to the force applied from the biasing member 64 to the core 50. In this regard, the outer holding sleeve 74 can be referred to as a brace member.

Accordingly, as a first force $F_1$ is applied to the wire 66 along a longitudinally forward direction, the stopper 68 applies a corresponding longitudinally forward biasing force to the rear link 28. The outer holding sleeve 74 applies a force $F_2$ into the outer linkage sleeve 30 that is equal and opposite with respect to the force $F_1$. The force $F_1$ applied to the wire 62 thus causes the inner core 50 to translate longitudinally forward with respect to the outer sleeve 30.

Figure 7:
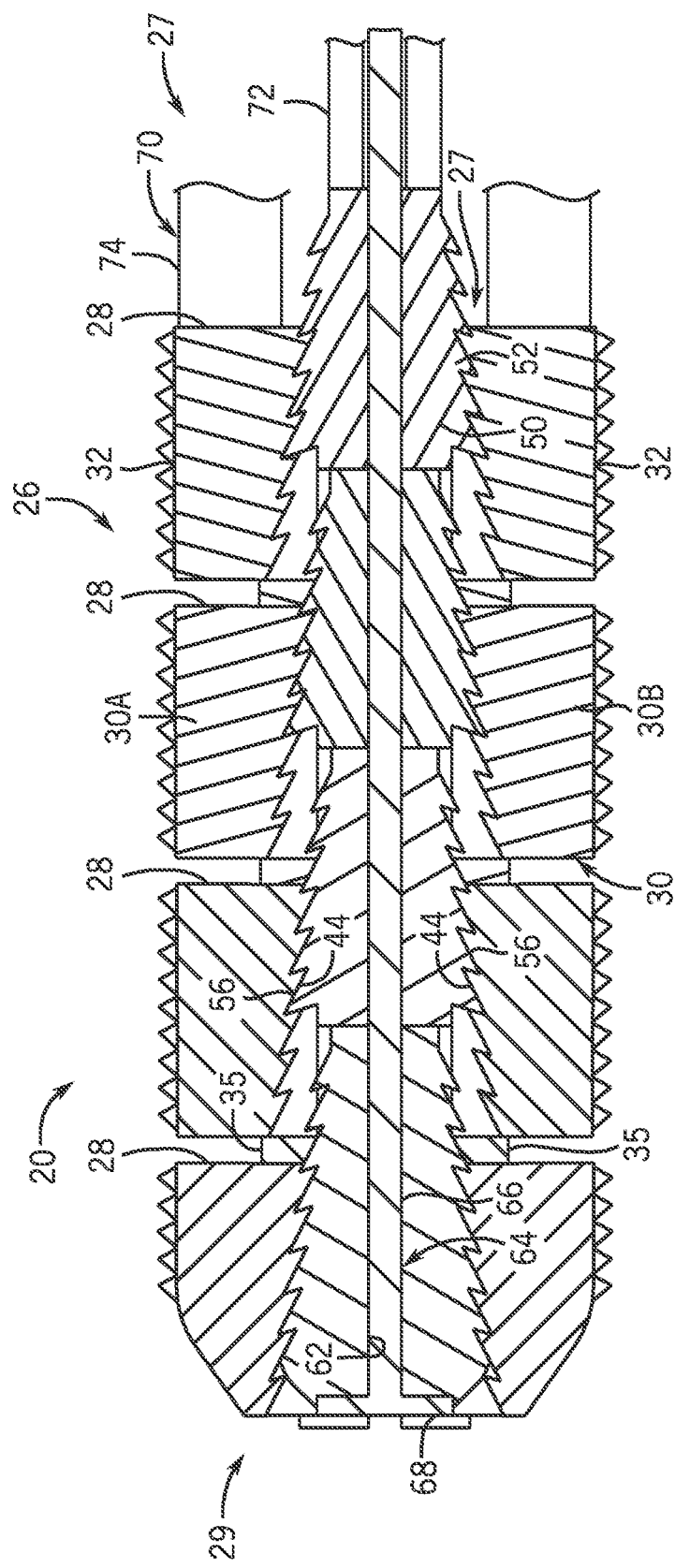
FIG. 7 is a sectional side elevation view of the expandable intervertebral implant illustrated in FIG. 6, but illustrated in a second vertically expanded position.

Referring also to FIG. 7, as the inner core 50 translates forward with respect to the outer sleeve 30, the engagement surfaces 40 ride along the complementary engagement surfaces 54, thereby causing the outer sleeve portions 30A and 30B to deflect vertically away from each other. As the outer sleeve portions 30A and 30B deflect away from each other, the intervertebral implant 20 expands in the transverse, or vertical, direction. The slope of the upper and lower mating engagement surfaces 40 and 54 determines the rate at which the upper and lower sleeves 30A and 30B expand, respectively.

As the inner core 50 moves in the forward direction with respect to the outer sleeve 30, the tips 46 and 60 of the engagement members, or teeth 44 and 56, cam over each other, thus causing the height of the implant 20 to increase in increments substantially equal to the height H of the teeth 44 and 56. Once a desired height is achieved and the biasing force is removed from the wire 62, the engaging teeth 44 and 56 can allow slight relative motion of the outer linkage sleeve 30 relative to the inner core 50 in the longitudinally forward direction, which can cause the outer teeth 34 of the sleeve to scuff the inner surfaces of the adjacent vertebrae 24, thereby facilitating fusion of the sleeve portions 30A and 30B to the vertebrae 24.

Once the teeth 44 and 56 become interlocked, relative motion between the inner core 50 and the outer sleeve 30 is prevented in the absence of the application of another biasing force to the cable 66. It should thus be appreciated that the linear forward motion of the inner core 50 relative to the outer sleeve 30 causes the intervertebral implant 20, or outer sleeve portions 30A and 30B, to expand from an initial, or relaxed position having a first height, to a second or an expanded position having a second height that is greater than the first height. The teeth 44 and 56 provide engagement members that prevent the outer sleeve portions 30A and 30B from contracting toward each other once the intervertebral implant 20, sleeve outer portions 30A and 30B, have reached the desired expanded position. It should be appreciated that while the engagement surfaces 40 and 54 of each link 28 each include a plurality of corresponding teeth, each engagement surfaces 40 and 54 could alternatively comprise one or more teeth.

During operation, the implant 20 is inserted into the intervertebral space 22 in the initial position, and subsequently expanded to a second expanded position so as to abut and position the adjacent vertebrae 24 to a desired vertical position that causes the intervertebral space to achieve a desired height. The intervertebral implant 20 can thus be referred to as an intervertebral spacer that causes the intervertebral space 22 between adjacent vertebrae to increase to a desired caudocranial height. An autograft or bone substitute can be placed around the implant 20 in the intervertebral space 22 if desired.

It should be appreciated that, as shown in FIG. 6, the core body 52 of the rear link 28 can be sized having a longitudinal length that is substantially longer than that of the corresponding outer sleeve 30. As a result, the core 50 can project rearward with respect to the sleeve 30 of the rearmost link 28 by an offset distance "O" when the implant 20 is in the initial or relaxed position. The offset distance O can be preselected based, for instance, on the slope of the engagement surfaces 44 and 54 and the desired expansion of the outer sleeve 30, such that once the implant 20 has reached the desired final height, the rear surface of the core 50 can be substantially flush with the rear surface of the outer sleeve 30 the rear link 28, as shown in FIG. 7.

Moreover, FIG. 6 shows the front end of the core body 52 of the front linkage 28 as being substantially flush with the front end of the outer sleeve 30 of the front linkage 28 when the implant 20 is in the initial position. Accordingly, as shown in FIG. 7, when the implant is in the expanded position, the front end of the core body 52 of the front linkage 28 extends forward from the front end of the outer sleeve 30 of the front linkage 28. It should be appreciated, however, that the front end of the core body 52 of the front linkage 28 could alternatively be recessed with respect to the front end of the outer sleeve 30 of the front linkage 28 a distance equal to the offset distance O when the implant 20 is in the initial position. Accordingly, when the implant 20 is in the expanded position, the front end of the core body 52 of the front linkage 28 could be substantially flush with the front end of the outer sleeve 30 of the front linkage 28.

Figure 8A:
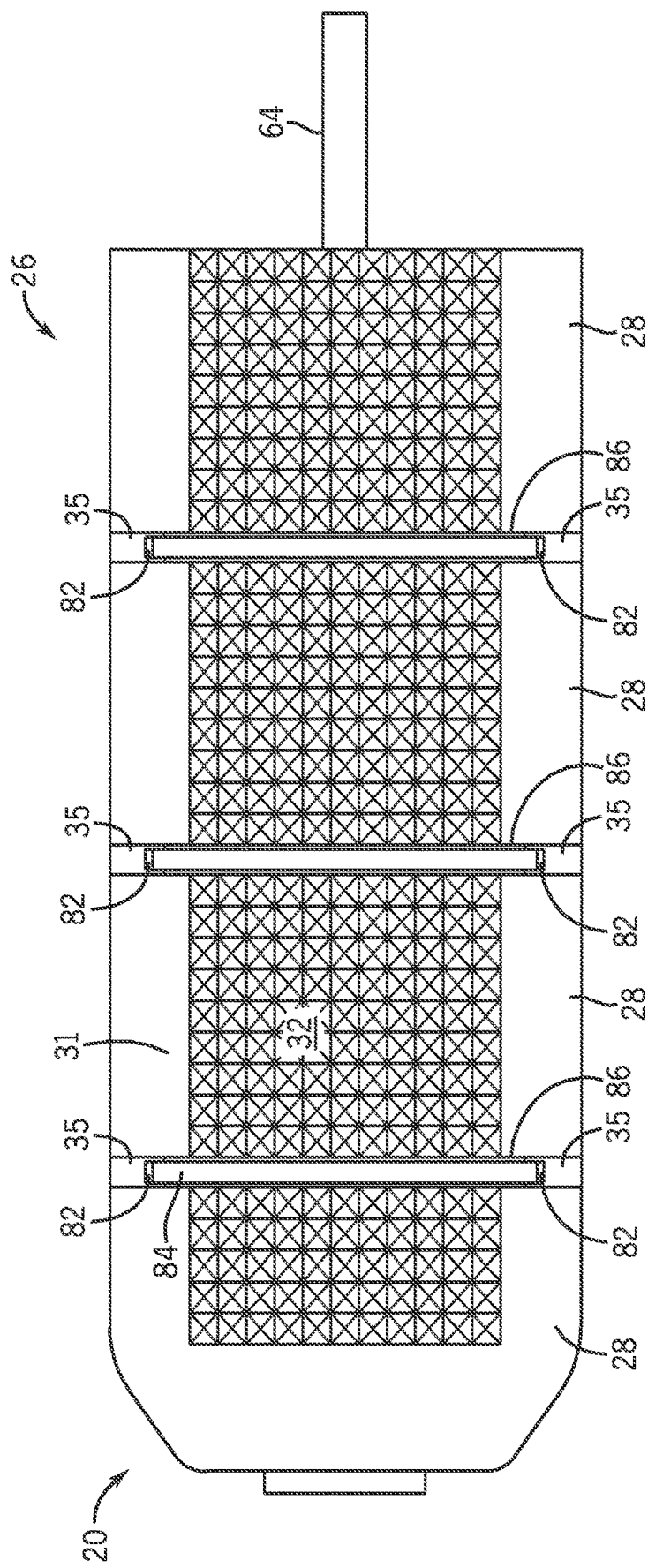
FIG. 8A is a top plan view of the expandable intervertebral implant illustrated in FIG. 7, including a retainer that secures various components of the expandable intervertebral implant.
Figure 8B:
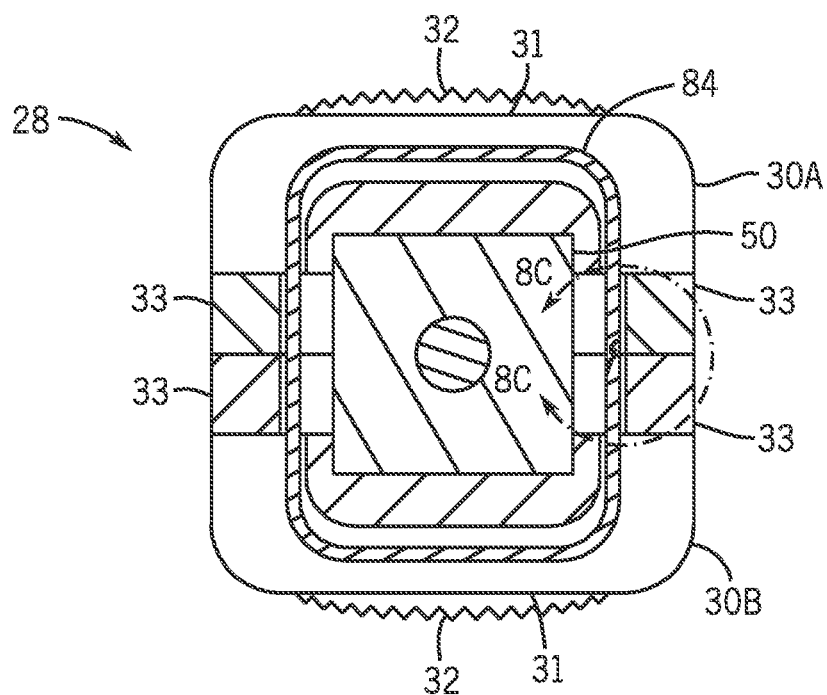
FIG. 8B is a sectional end view of the expandable intervertebral implant as illustrated in FIG. 8A.
Figure 8C:
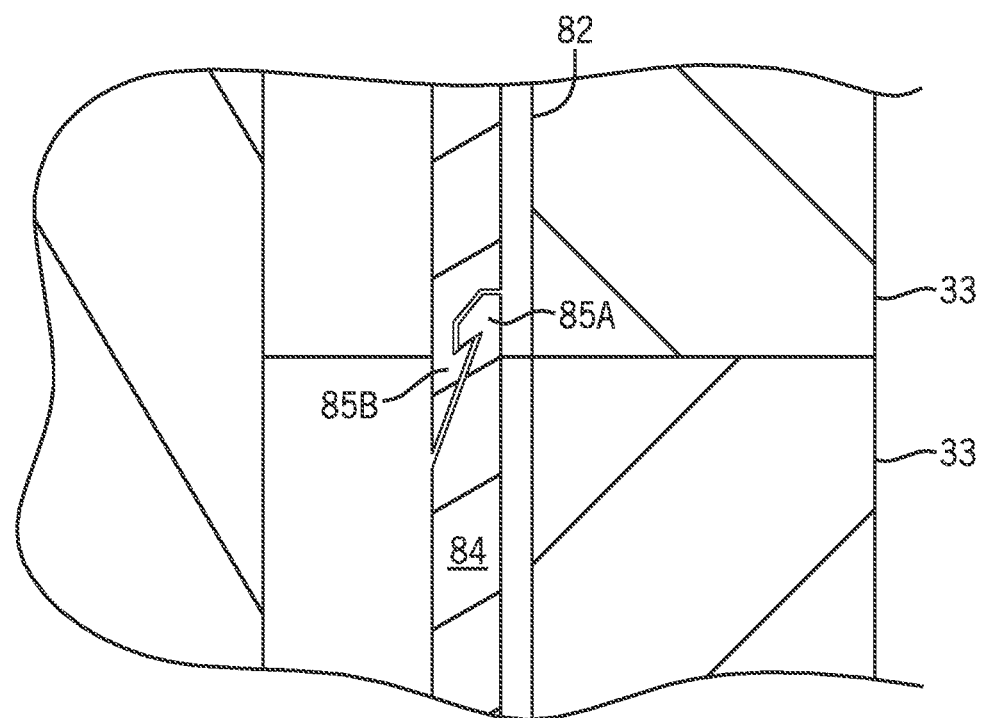
FIG. 8C is an enlarged view of a portion of the expandable intervertebral implant illustrated in FIG. 8B.

Referring now to FIGS. 8A-C, the expandable intervertebral implant 20 can include a retainer member in the form of one or more, such as a plurality of, bands 84 that are configured to apply a compressive retention force against the links 28 that can assist in maintaining the structural integrity of the implant 20 as the implant 20 is inserted into the intervertebral space 22 and expanded to the vertically expanded position. In particular, the linkage 26 can include laterally opposing transverse slots 82 that extend vertically through the coupling members 35. The coupling members 35 can include a lateral portion that extends in a laterally extending groove 86 disposed between adjacent links 28.

A metallic or elasticized band 84 can be inserted through the laterally opposing slots 82 and sit in the grooves 86 such that the band 84 surrounds the legs 33 of the outer sleeve portions 30A and 30B. The band 84 can include terminal ends 85A and 85B that form an interlocking tongue-and-groove. Thus, the terminal ends 85A and 85B can be clipped together, and the terminal ends can be placed inside one of the slots 82 so as to reduce the possibility that the band 84 would be inadvertently separated. The bands 84 can apply a compressive force that biases the outer sleeve portions 30A and 30B against each other and against the inner core 50, thereby assisting in the retention of the teeth 44 and 56 in their interlocked configuration. The bands 84 can be radiolucent so as to provide an indication of the position and angular orientation of the implant 20 during the implantation procedure.

Figure 9A:
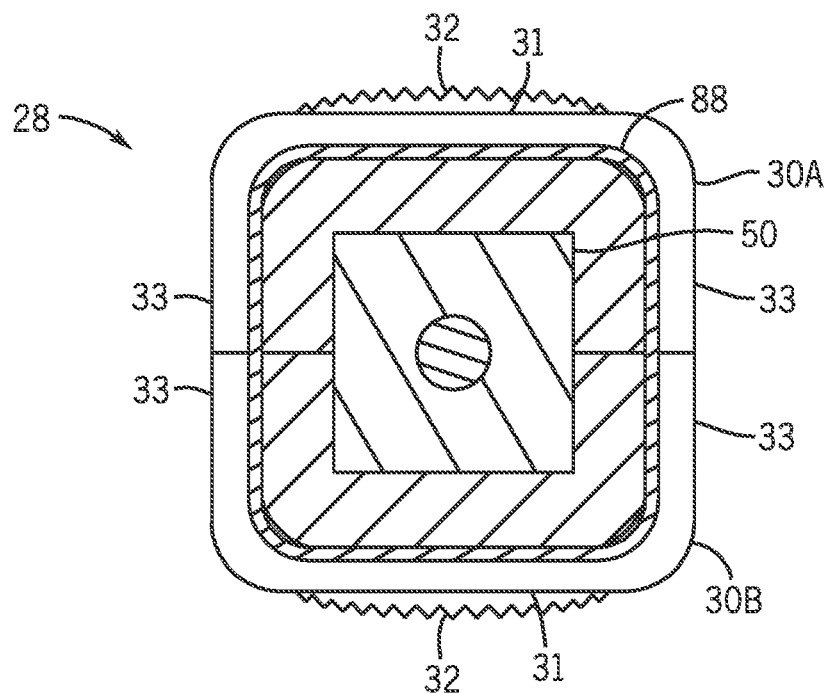
FIG. 9A is a sectional end view of the expandable intervertebral implant similar to FIG. 8B, but showing a retainer constructed in accordance with an alternative embodiment.
Figure 9B:
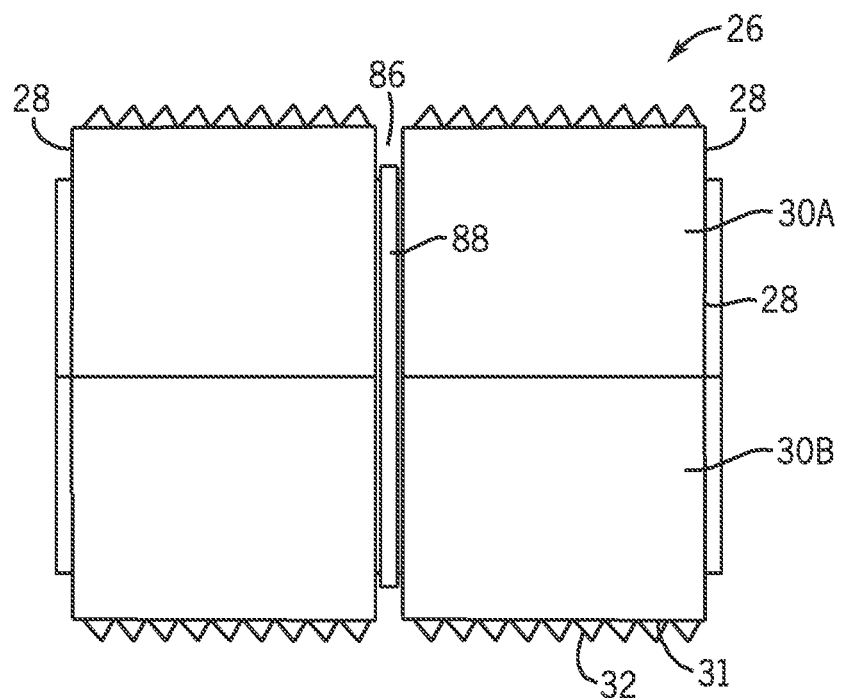
FIG. 9B is a side elevation view of the expandable intervertebral implant illustrated in FIG. 9A.

Referring now to FIG. 9A-B, the expandable intervertebral implant 20 can include a retainer member constructed in accordance with an alternative embodiment. In particular, the legs 33 do not define a transverse slot extending vertically therethrough. Instead, an elasticized band 88 can be stretched over one or more of the links 82 and inserted into the groove 86. The elasticity of the band 88 can apply a compressive force that biases the outer sleeve portions 30A and 30B against each other and against the inner core 50, thereby assisting in the retention of the teeth 44 and 56 in their interlocked configuration. The plurality of bands 88 can be radiolucent so as to provide an indication of the position and angular orientation of the implant 20 during the implantation procedure.

Figure 10:
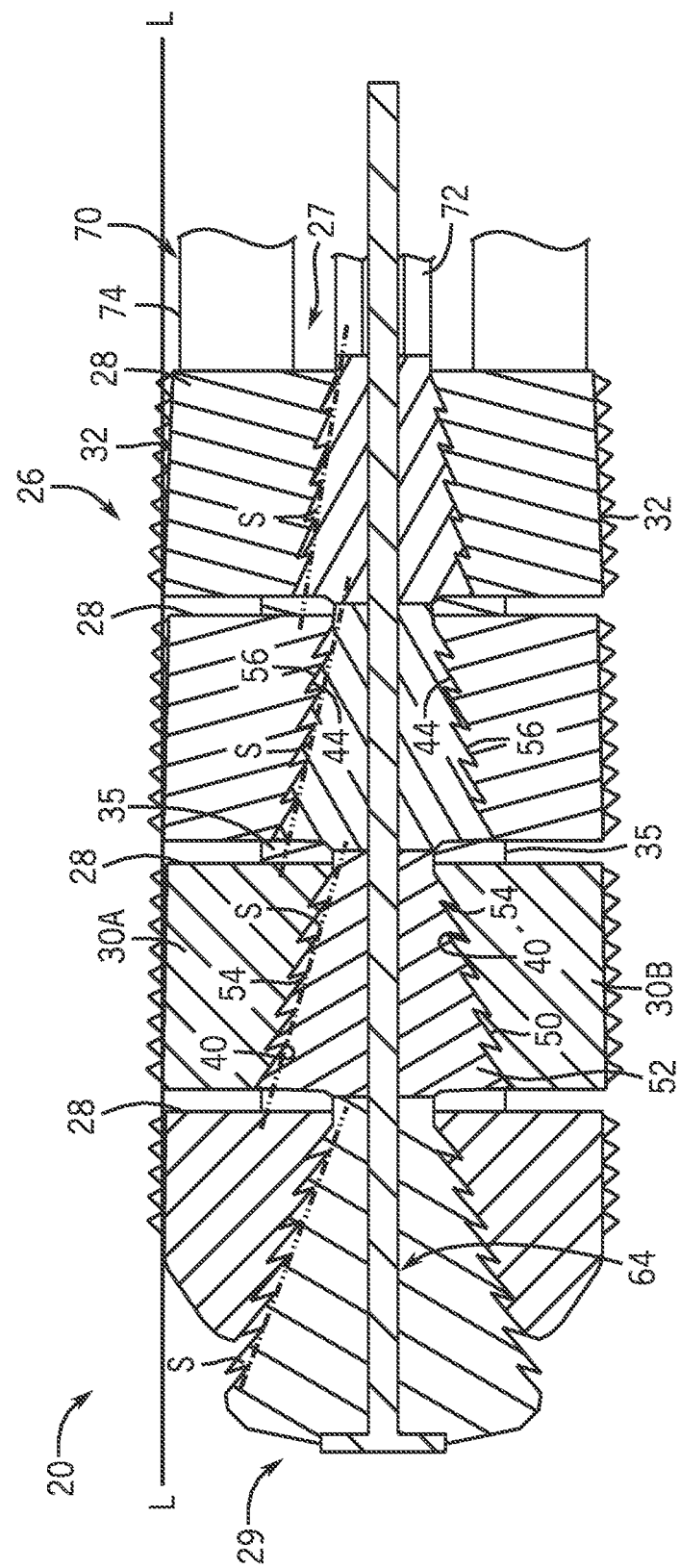
FIG. 10 is a sectional side elevation view of an expandable intervertebral implant similar to FIG. 6, but configured to provide a lordotic outer profile when expanded, in accordance with an alternative embodiment.

Referring now to FIG. 10, the expandable intervertebral implant can be constructed such that the vertebral engagement surfaces 32 define a lordotic profile when the implant 20 is in the expanded position. In accordance with the illustrated embodiment, the slope S of the engagement surfaces 40 and 54 relative to the longitudinal axis L-L of each link 28 vary from link to link. Thus, the opposing engagement surfaces 40 and 54 of one link are angled, or not parallel, with respect to the corresponding opposing engagement surfaces 40 and 54 of an adjacent link. For instance, the slope of each interfacing engagement surfaces 40 and 50 of each link 28 relative to the longitudinal axis L-L has a magnitude that decreases along a direction from the rear link 28 toward the front link 28. Thus, the magnitude of the slope of the complementary engagement surfaces 40 and 54 of a given link 28 is greater than that of forwardly disposed links 28, and less than that of rearwardly disposed links 28.

Accordingly, as the implant 20 expands, the outer sleeve portions 30A and 30B of each link 28 will become vertically displaced at different rates. In the illustrated embodiment, the rate of outer sleeve vertical displacement will decrease in a direction from the rear link 28 toward the front link 28. It should, of course, be appreciated that the slope of the engagement surfaces 40 and 50 of each link could alternatively decrease in a direction from the front link 28 toward the rear link 28 such that the rate of vertical displacement would decrease in a direction from the front link 28 toward the rear link 28. Alternatively still, the middle links 28 can expand at a rate that is greater than or less than the forward and rearward spaced links 28.

In the embodiment illustrated in FIG. 10, the vertebral engagement surfaces 32 of the opposing outer sleeve portions 30A and 30B can be substantially flat in the longitudinal direction. The slope of opposing vertebral engagement surfaces 32 of each link 28 can vary from link to link. Thus, the vertebral engagement surfaces 32 of one link are angled, or not parallel, with respect to the engagement surfaces 32 of an adjacent link. It can also be said that the engagement surfaces 32 of each link 28 are sloped at an angle with respect to the longitudinal direction that is different than the angle at which the engagement surfaces 32 of the other links are sloped relative to the longitudinal direction.

The opposing engagement surfaces 32 of the outer sleeve portions 30A and 30B of a given link 28 can be equal and opposite relative to the longitudinal axis L-L. As illustrated, the vertebral engagement surfaces 32 of the links 28 each define a slope having a magnitude with respect to the longitudinal axis L-L that decrease from link to link as the slope of the corresponding engagement surfaces 40 and 50 increase when the implant 20 is in the initial position. Thus, in the illustrated embodiment, the slope of each of the vertebral engagement surfaces 32 of the links 28 has a magnitude that decrease in direction from the front end 27 of the linkage 26 toward the rear end 29 of the linkage. The magnitude of the slope of the opposing vertebral engagement surface 32 of a given link 28 is greater than that of rearwardly disposed links 28, and less than that of forwardly disposed links. Alternatively, the slope of the opposing vertebral engagement surfaces 32 of each link 28 could be substantially identical from link to link.

Figure 11:
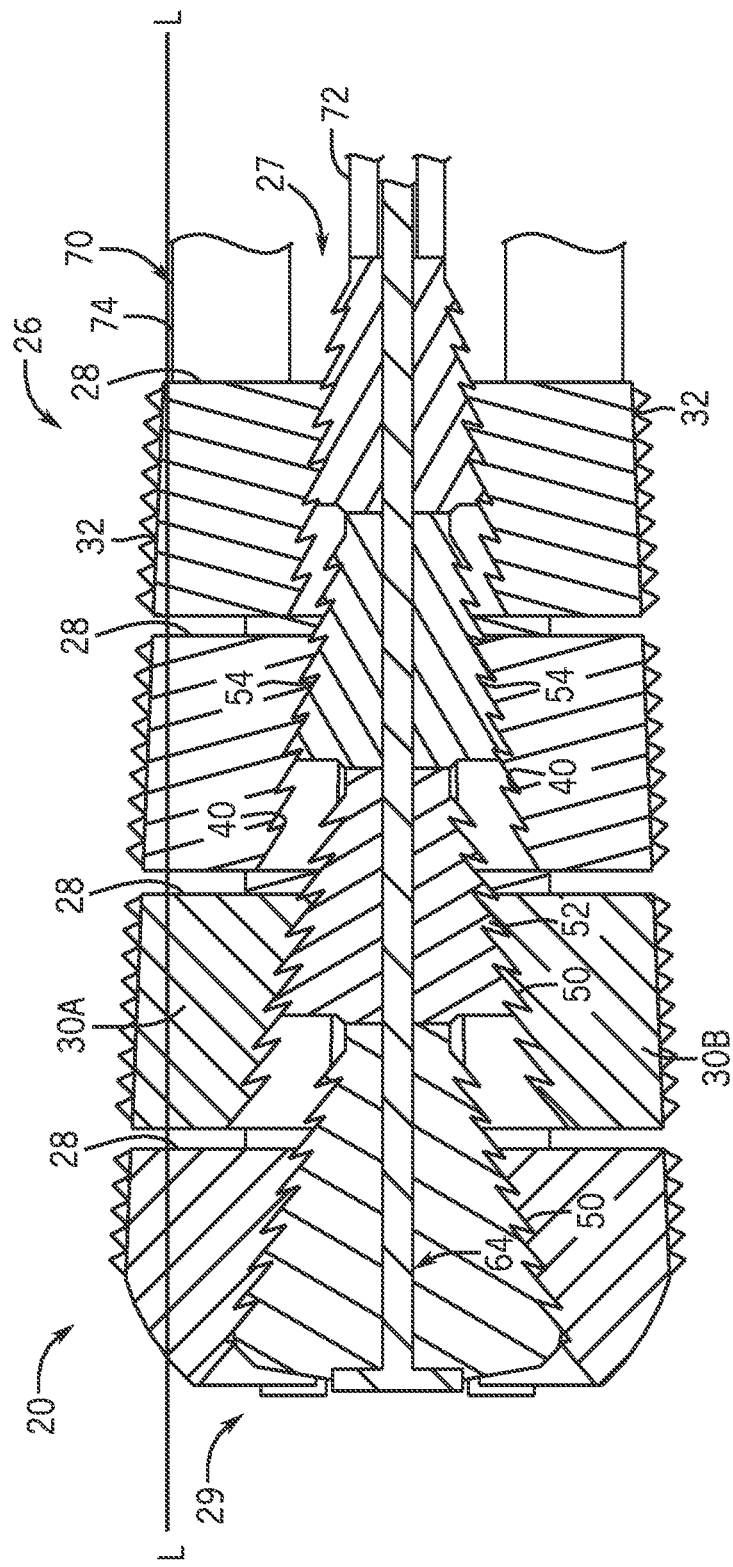
FIG. 11 is a sectional side elevation view of the expandable intervertebral implant illustrated in FIG. 10, but showing the implant in a vertically expanded position.

Referring now to FIG. 11, when the inner core 50 is moved longitudinally forward relative to the outer sleeve 30 to move the implant from the initial position to the expanded position in the manner described above, the links 28 expand at different rates. In particular, a given link 28 expands at a faster rate than forwardly disposed links, and at a rate slower than rearwardly disposed links. As a result, when the intervertebral implant 20 is in the expanded position illustrated in FIG. 11, the opposing outer sleeve portions 30A and 30B of each link 28 have expanded a distance that is greater than those of forwardly disposed links, and less than those of rearwardly disposed links. Thus, the implant 20 defines vertebral engagement surfaces 32 that are sloped transversely outward with respect to the longitudinal axis L-L in a direction from the front end 27 toward the rear end 29. Moreover, the vertebral engagement surfaces 32 of each outer sleeve portion 30A and 30B are in line with the vertebral engagement surfaces 32 of the other links 28 of the linkage 26, thereby creating reliable engagement surfaces with the vertebrae 24.

Figure 12:
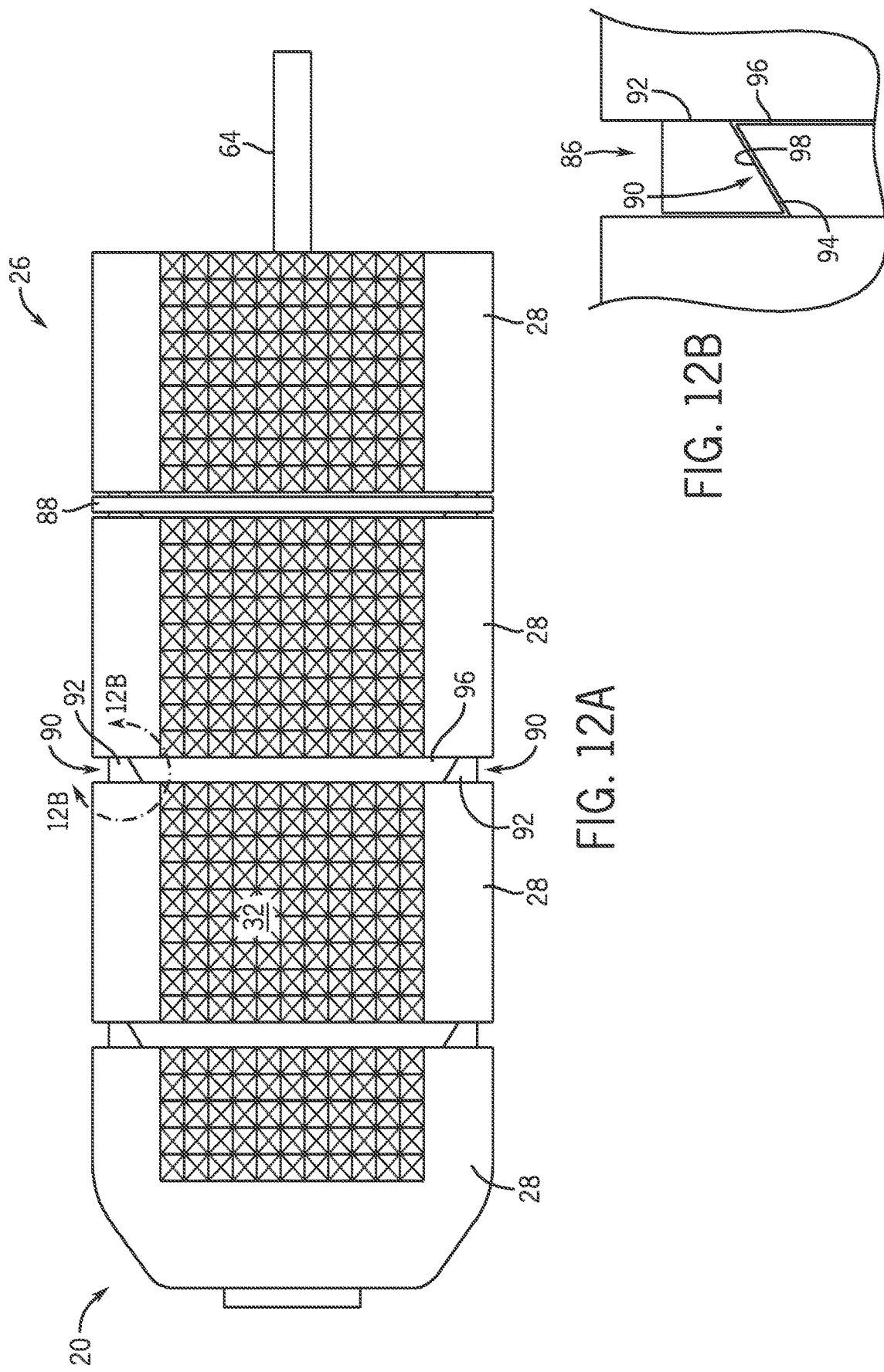
FIG. 12A is a top plan view of the expandable intervertebral implant illustrated in FIG. 10.
FIG. 12B is an enlarged side elevation view of a portion of the expandable intervertebral implant illustrated in FIG. 12A.

Referring to FIGS. 12A-B, it should be appreciated that the links 28 can be coupled so as to permit relative vertical motion between adjacent links. Accordingly, the adjacent links 28 can be coupled by a joint, such as a tongue-and-groove joint 90. The joint 90 includes a pair of first laterally opposing engagement members 92 attached to one of the adjacent links 28. The engagement members 92 extend vertically, and each includes a beveled surface 94 that slopes laterally inward along a direction longitudinally away from the link 28. The other of the adjacent links 28 includes a second laterally elongate engagement member 96 that extends laterally between the opposing engagement members 92. The engagement member extends vertically, and includes laterally opposing beveled surfaces 98 that slopes laterally outward along a direction longitudinally away from the link 28. The beveled surfaces 94 and 98 engage each other to interlock the adjacent links with respect to longitudinal separation, while allowing for relative vertical motion along the beveled surfaces 94 and 98, and thus relative vertical motion between the adjacent links 28. A retainer member, such as band 88, can further be inserted into one or more of the grooves 86 that separate the adjacent links 28 so as to further maintain the structural integrity of the linkage 26 during use in the manner described above.

Figure 13:
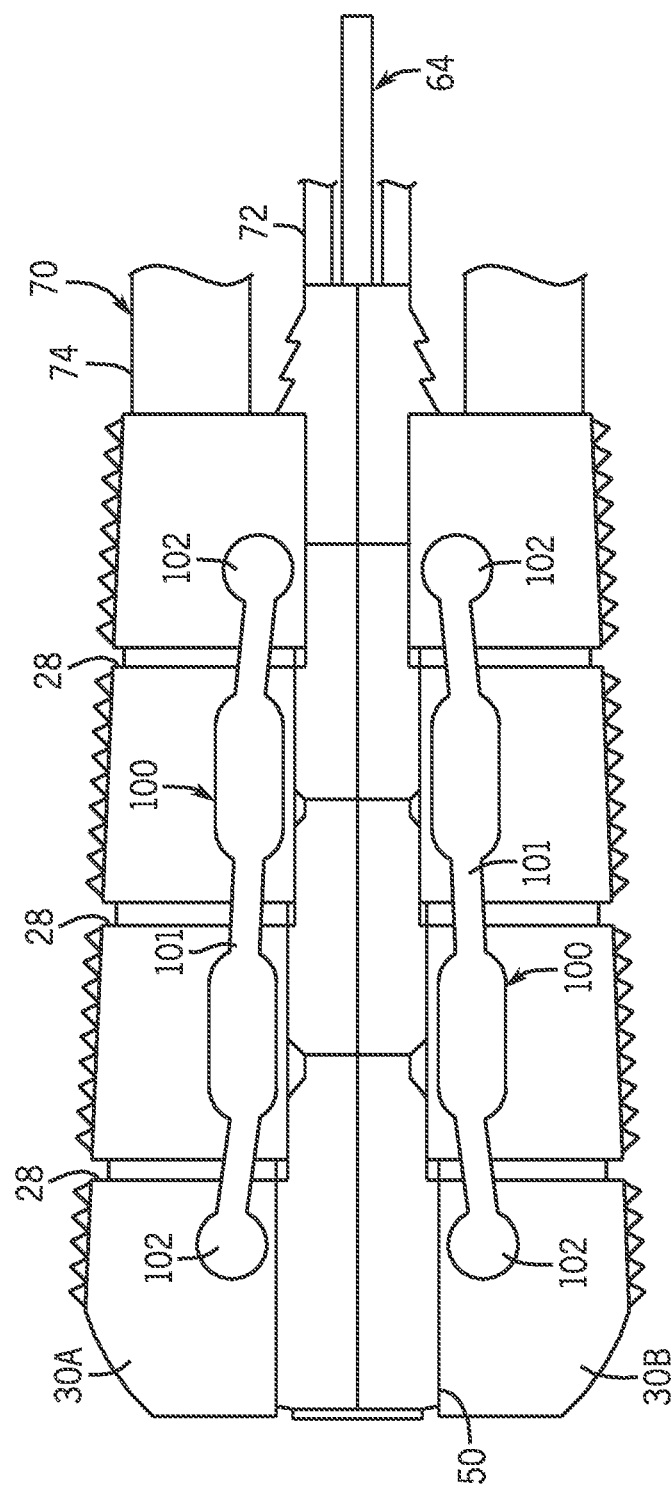
FIG. 13 is a side elevation view of an expandable intervertebral implant including a second retainer constructed in accordance with an alternative embodiment.
Figure 14:
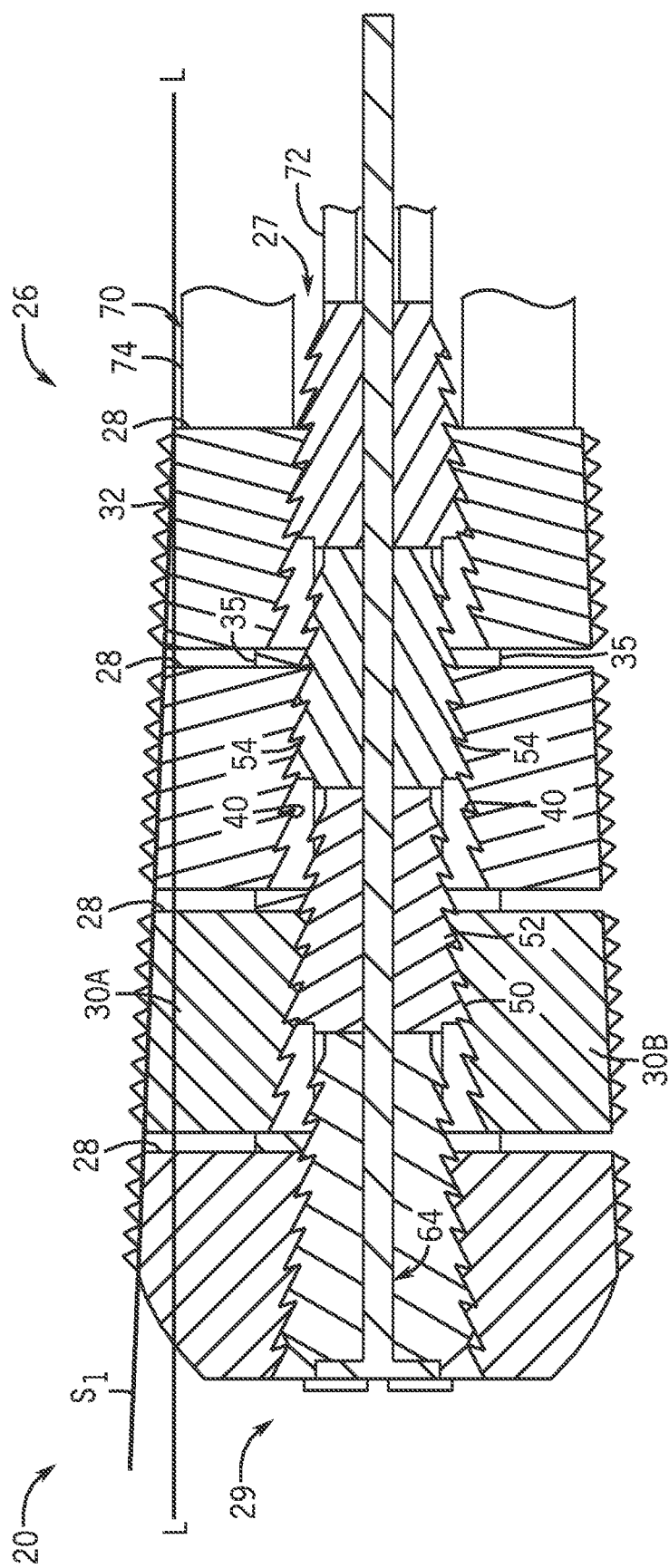
FIG. 14 is a sectional side elevation view of an expandable intervertebral implant similar to FIG. 10, but configured to define a lordotic outer profile when expanded, in accordance with an alternative embodiment.

Alternatively or additionally, the expandable intervertebral implant 20 can include an auxiliary retainer such as a flexible band 100 as illustrated in FIG. 13. The band 100 defines a body 101 that extends generally in the longitudinal direction, and defines a pair of opposing terminal ends 102 that each define connection locations that can be connected to an outer sleeve portion 30A or 30B of a different one of the plurality of links 28. The terminal ends 102 can define a hinged connection with respect to the outer sleeve portion, or can define a fixed connection such that the flexibility of the band 100 allows the terminal ends 102 and other connection locations to rotate relative to the body 101. The bands 100 can be fastened to the outer sleeve portions 30A and 30B using any suitable mechanical fastener.

In the illustrated embodiment, the terminal ends 102 of one band 100 are connected to the laterally outer surfaces of the upper sleeve portions 30A of the longitudinally outermost links 28. The terminal ends 102 of another band 100 are connected to the laterally outer surfaces of the lower sleeve portions 30B of the longitudinally outermost links 28. A pair of substantially identical bands can be connected to the opposing outer lateral surfaces of the upper and lower sleeve portions 30A and 30B. Thus, the bands 100 provide a longitudinal compressive force to all links 28 disposed between the terminal band ends 102. Alternatively, the bands 100 can be connected to one or more, up to all, links 28 that are disposed between the terminal ends 102 of the bands 100.

It should be appreciated that FIGS. 10-13 illustrate the intervertebral implant 20 configured to produce a lordotic profile in accordance with one embodiment, and that alternative embodiments can be provided to create a lordotic profile. For instance, referring to FIG. 13, the vertebral engagement surfaces 32 of each outer sleeve portions 30A and 30B are aligned with the vertebral engagement surfaces 32 of the corresponding outer sleeve portions 30A and 30B of the adjacent links. Thus, the vertebral engagement surfaces 32 of each outer sleeve portion 30A are aligned and parallel to each other, and the vertebral engagement surfaces 32 of each outer sleeve portion 30b are aligned and parallel to each other. Moreover, the engagement surfaces 32 of each outer sleeve portion 30A and 30B can be sloped with respect to the longitudinal axis L-L. In the illustrated embodiment, the engagement surfaces 32 define a slope $S_1$ that is angled transversely out from the longitudinal axis L-L in a direction from the front end 27 of the linkage 26 toward the rear end of the linkage. It should be appreciated, however, that the engagement surfaces 32 could alternatively slope transversely in from the longitudinal axis L-L in a direction from the front end 27 of the linkage 26 toward the rear end of the linkage.

Furthermore, the engagement surfaces 40 and 50 of each outer sleeve portion 30A are aligned with and extend parallel to the engagement surfaces 40 and 50 of the outer sleeve portions 30A of the other links 28. Likewise, the engagement surfaces 40 and 50 of each outer sleeve portion 30B are aligned with and extend parallel to the engagement surfaces 40 and 50 of the outer sleeve portions 30B of the other links 28. Accordingly, as the implant is expanded to the expanded position illustrated in FIG. 13, each link 28 is displaced transversely outward at the same displacement rate of the other links, and the vertebral engaging surfaces 32 maintain the lordotic profile described above.

Thus, the expandable intervertebral implant 20 is configured to expand along the transverse direction and can be further configured such that the vertebral engaging surfaces 32 can define a lordotic profile when engaged with the vertebrae. Alternatively or additionally, the intervertebral implant 20 can be configured such that the vertebral engaging surfaces 32 of the links 28 combine to define a nonlinear shape, such as a curved convex shape having outer longitudinal ends that are disposed transversely inward with respect to a longitudinal middle portion.

Referring to FIG. 15A, the opposing axially inner surfaces of the legs 33 of each outer sleeve portion 30A and 30B can define laterally opposing, and vertically extending, engagement surfaces 110 that can be longitudinally elongate, and sloped laterally with respect to the longitudinal axis L-L at any desired angle as described above with respect to the transverse angle formed between inner engagement surface 40 and the longitudinal axis. Accordingly, that the engagement surface 110 of each sleeve portion slopes laterally out from the longitudinal axis along a direction from the front end 27 toward the rear end 29 of the linkage 26. In this regard, it should be appreciated that the laterally sloped engagement surface 110 can be constructed as described above with respect to the transversely sloped engagement surface 40. However, the cross beam 31 of each outer annular sleeve is discontinuous along the lateral direction, such that each leg of the outer sleeve portions 30A and 30B is free to move relative to the other leg of the same outer sleeve portion in the lateral direction. Each leg of a given outer sleeve portion is free to move in the transverse direction with respect to the legs of the opposing outer sleeve portion in the manner described above.

The engagement surfaces 110 of the upper sleeve portions 30A can define an angle greater or less than that of the other, and can further define an angle greater or less than that of the engagement surfaces 110 of the lower sleeve portions 30B, thereby causing one lateral side of the outer sleeve 30 to expand laterally at a higher or lower expansion rate, respectively, relative to the other lateral side of the outer sleeve 30. In this regard, it should be appreciated that the angle of one or both of the of the inner engagement surfaces 110 relative to the longitudinal axis L-L could be zero, while the angle of the other engagement surface 110 relative to the longitudinal axis L-L is non-zero, thereby causing only one lateral side of the outer sleeve to expand laterally during operation.

The engagement surfaces 110 of each link 28 can be aligned with, and extend parallel to, the engagement surfaces 110 of the other links 28 of the linkage 26. Thus, the outer sleeve 30 of each link 28 can extend laterally at its front end a greater amount than at its rear end. Each link 28 can further include an engagement member in the form of reverse angled teeth 114 that project laterally inward from the engagement surface 110. The lateral teeth 114 can be constructed in the manner described above with reference to the transverse teeth 44.

The inner core body 52 defines laterally outer engagement surfaces 124 that are configured to engage the engagement surfaces 110 of the upper and lower sleeves 30A and 30B. The inner core body 52 can extend vertically a sufficient distance such that each engagement surface 124 can engage with the pair of complementary engagement surfaces 110 on each lateral side of the sleeve 30. The engagement surfaces 124 can be laterally sloped with respect to the longitudinal axis L-L, and can thus extend parallel to the corresponding engagement surfaces 110. The lateral engagement surfaces 124 can be constructed as described above with respect to the transverse engagement surfaces 54. The inner core 50 can further include an engagement member in the form of reverse angled teeth 126 that project laterally out from the engagement surfaces 124. The teeth 126 can be sized and shaped substantially identical with respect to teeth 114, so as to mate with teeth 114. The teeth 126 can be constructed in the manner described above with respect to teeth 56.

Figure 15B:
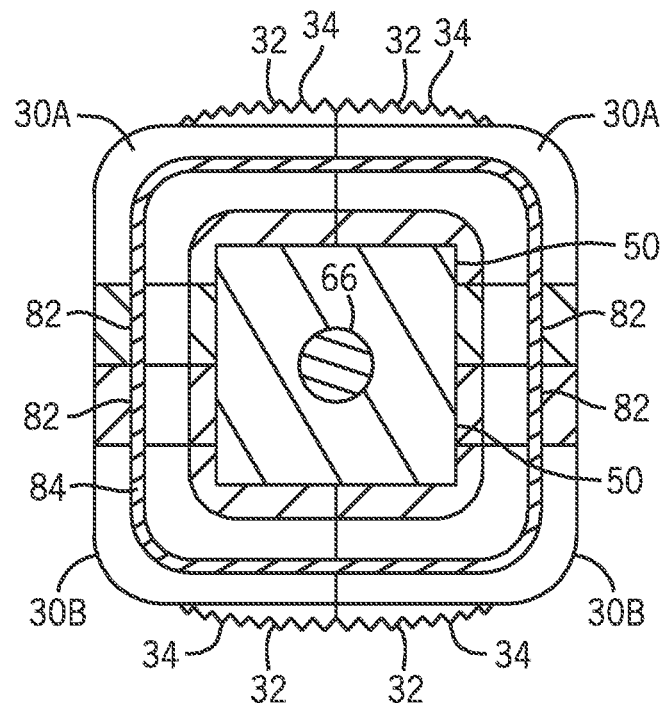
FIG. 15B is a sectional end view of the expandable intervertebral implant illustrated in FIG. 15A including a retainer constructed in accordance with one embodiment.

As illustrated in FIG. 15B, the outer sleeve portions 30A and 30B can be retained by a retainer such as a plurality of bands 84 in the manner described above. Slots 82 can extend vertically through both pairs of opposing laterally outer legs 33, and the band 84 can be inserted into the slots 82 and placed in the groove 86 in the manner described above to apply compressive retention forces onto the linkage, thereby assisting in securing the structural integrity of the expandable intervertebral implant 20. Alternatively, as illustrated in FIG. 15D, the retainer may be provided as an elasticized band 88 that is placed in the groove 86 in the manner described above to apply laterally and transverse compressive securing forces.

Figure 15C:
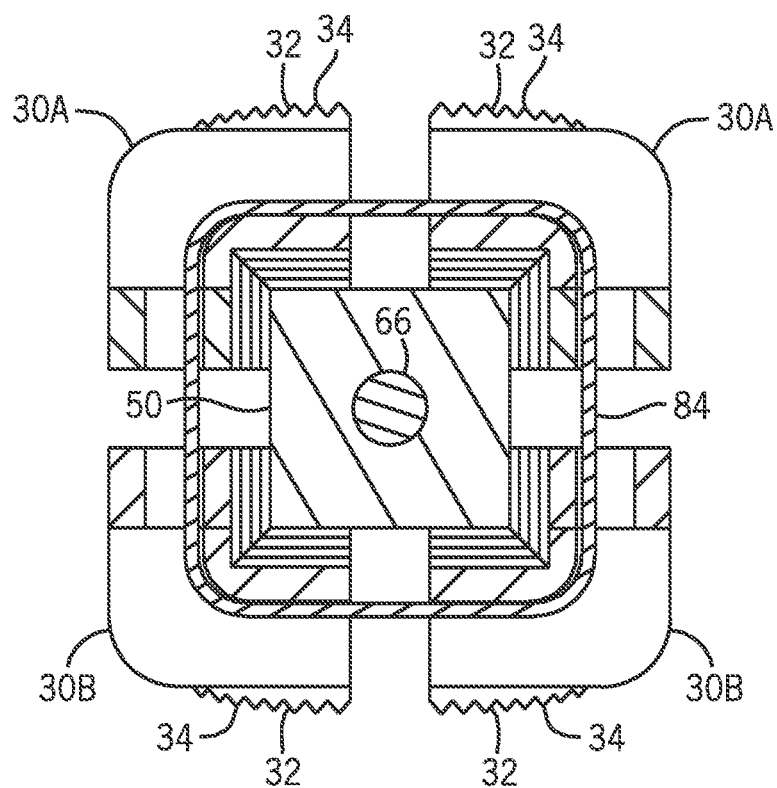
FIG. 15C is a sectional end view of the expandable intervertebral implant similar to FIG. 15B, but showing the expandable intervertebral implant in a vertically and laterally expanded position.
Figure 15D:
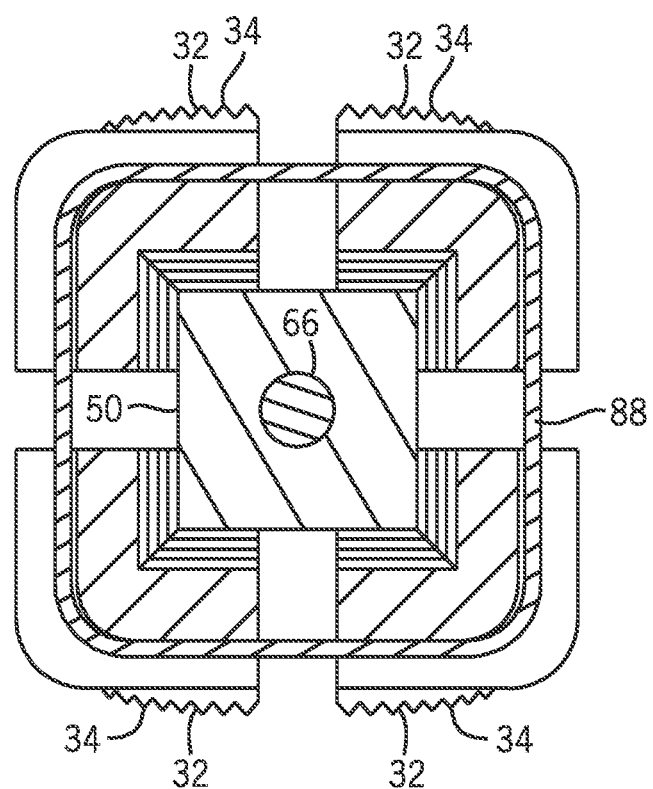
FIG. 15D is a sectional end view of the expandable intervertebral implant similar to FIG. 15C, but including a retainer constructed in accordance with an alternative embodiment.

Referring now to FIGS. 15A and 15C, as the inner core 50 moves in the forward direction with respect to the outer sleeve 30, the engagement surfaces 40 ride along the complementary engagement surfaces 54, and the teeth 44 and 56 cam over each other, thereby causing the outer sleeve portions 30A and 30B to incrementally deflect vertically away from each other in the manner described above. Furthermore, the engagement surfaces 110 ride along the complementary engagement surfaces 124, and the teeth 114 and 126 cam over each other, thereby causing the laterally outer portions of the outer sleeve 30 to incrementally deflect laterally away from each other from a first laterally contracted position to a second laterally expanded position. It should be appreciated that the engagement surfaces 110 and 124 can have a slope that is greater than or less than the slope of engagement surfaces 40 and 54, such that the implant 20 can expand vertically at a greater rate or a lesser rate than the implant 20 expands laterally.

It should be appreciated that a kit can be provided that includes all or a portion of the expandable intervertebral implant 20 constructed in accordance with any of the embodiments described herein. For example, the kit can include one or more of the components of the expandable intervertebral implant, such as the upper and lower outer sleeve portions 30A and 30B, the inner core 50, bands 84 and 88, and a plurality of links 28. The one or more components included in various kits can have one or more varying characteristic such as size and/or shape. For instance, a first kit can be provided having one or more components, for instance outer sleeve portions 30A and 30B, the inner core 50, bands 84 and 88, and a plurality of links 28, that have a different size or shape to accommodate different expansion rates, different longitudinal and/or lateral lengths, and different directions of expansion, for instance transverse expansion alone or coupled with lateral expansion. Some components in a given kit may permit the implant 20 to produce a lordotic profile in the manner described above, while other components in the kit may permit the implant to produce a horizontal upper and lower vertebrae-engaging surface. The kit can further include components of the insertion tool 70 as will now be described.

Figure 16A:
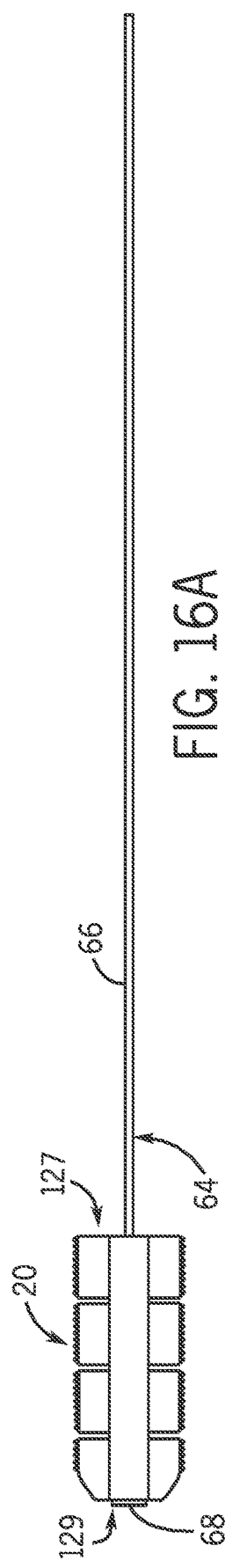
FIG. 16A is a side elevation view of an expandable intervertebral implant coupled to a biasing member of an insertion device in accordance with one embodiment.
Figure 16B:
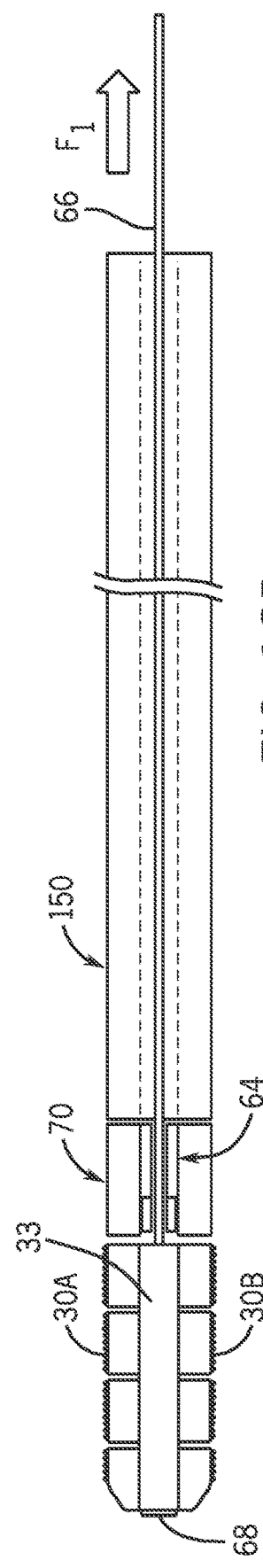
FIG. 16B is a side elevation view of the expandable intervertebral implant illustrated in FIG. 16A, but with the biasing member coupled to additional components of the insertion device, wherein the insertion device is illustrated in a disengaged position.
Figure 16C:
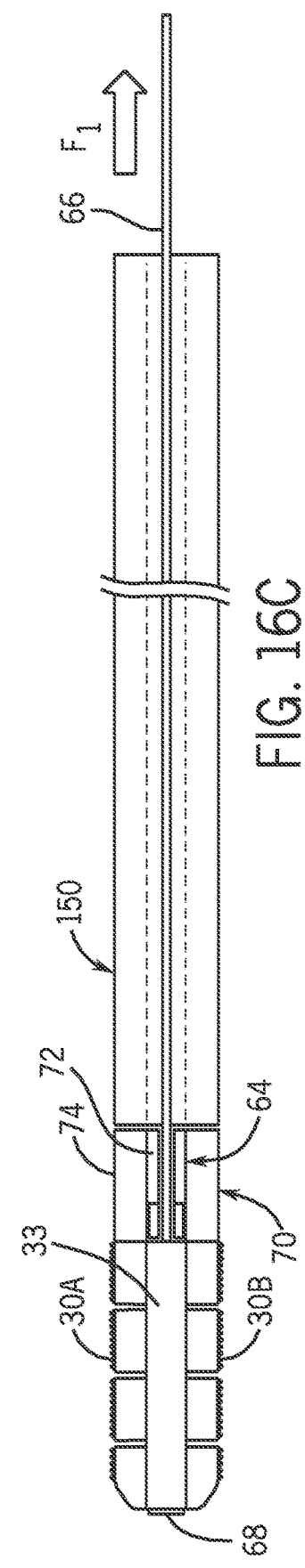
FIG. 16C is a side elevation view of the expandable intervertebral implant as illustrated in FIG. 16B, but showing the insertion device in an engaged position.

In particular, referring now to FIGS. 16A-C, the insertion tool 70 can be configured to engage the intervertebral implant 20 such that the implant 20 may be inserted into the intervertebral space 22 and subsequently expanded in the manner described above. Once the intervertebral implant is disposed in the intervertebral space, the insertion tool can include biasing members that apply a biasing force to the implant, thereby causing the implant to expand in any manner as described above. Once the implant 20 has reached the desired expansion position, the insertion tool 70 may be disengaged from the implant 20.

The insertion tool 70 can include the inner annular holding sleeve 72, the biasing member 64 that extends inside the inner annular holding sleeve 72, and the outer annular holding sleeve 74 that receives the inner annular holding sleeve 72. Once the holding member 70 is moved to position such that the inner annular holding sleeve 72 abuts the inner core 50 and the outer annular holding sleeve 74 abuts the outer sleeve 30, a force F1 can be applied to the wire 66 that causes the implant to expand in the manner described above.

Figure 17A:
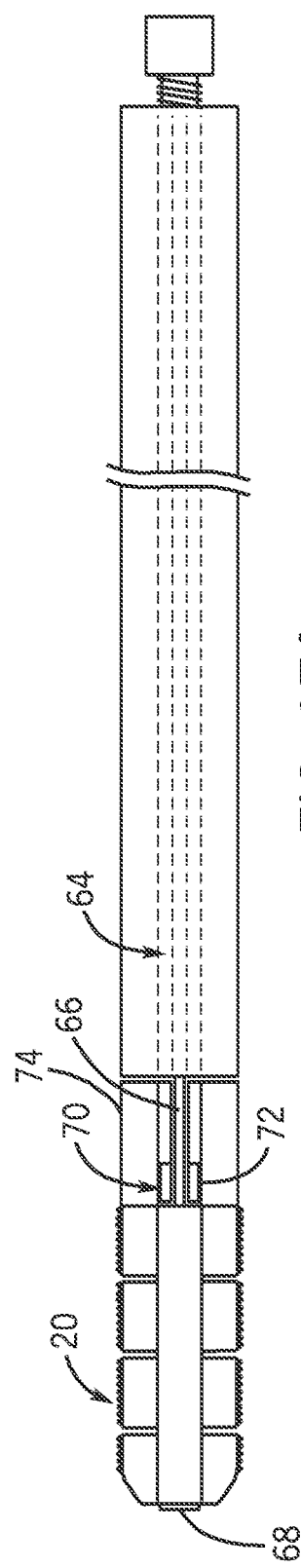
FIG. 17A is a side elevation view of the expandable intervertebral implant as illustrated in FIG. 16C, but showing the insertion device including a central sleeve having a coupling member that locks the insertion device in the engaged configuration.
Figure 17B:
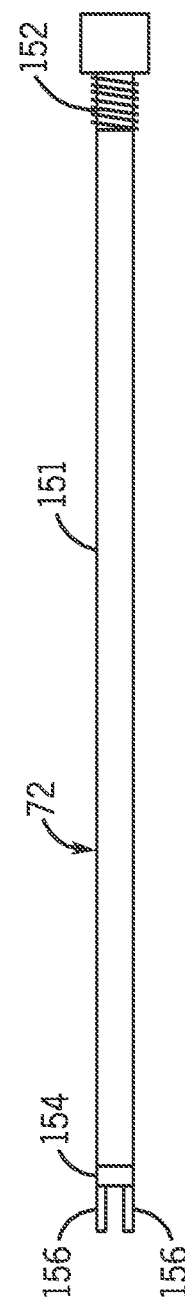
FIG. 17B is a side elevation view of the central sleeve illustrated in FIG. 17A.
Figure 17C:
FIG. 17C is a top plan view of the central sleeve illustrated in FIG. 17B.

Referring to FIGS. 17A-C, the inner annular holding sleeve 72 can include a longitudinally elongate body 151 having a threaded engagement surface 152 at a distal end that is configured to be threadedly received in the outer annular holding sleeve 74. The inner annular holding sleeve 72 can include a proximal end having a forked abutment member 154. The forked abutment member 154 can include a pair of spaced prongs 156 that are configured to abut the inner core 50 in the manner described above. The wire 62 can thus extend through the inner core 50 of each link 28, between the prongs 156 and through the inner annular holding sleeve 72. The free end of the wire that extends through the inner annular holding sleeve can be coupled to any suitable tensioning device configured to apply a biasing force sufficient to cause the intervertebral implant 20 to expand.

Referring now to FIGS. 18A-B, the insertion tool 70 can further include an angulated member 158 that is connected between the forward end 127 of the linkage 26, and the proximal ends of the inner and outer holding sleeves 72 and 74. The angulated member 158 can include a rectangular block 159, a cylindrical body 160 rigidly attached to the block 159, and a bore 162 extending through the body 160 sized to receive the wire 66. The wire 66 can thus extend through the linkage 56, the cylindrical body 160, and the inner sleeve 72. The outer sleeve 73 can define a bore 164 extending longitudinally therethrough, and a directional rod 166 extending through the bore 164. The directional rod 166 defines a proximal end that is pivotally coupled to the block 159 at a connection location 158 that is laterally offset with respect to the lateral center of the cylindrical body 160.

During operation, the rectangular block 159 abuts the inner core 50, and the directional rod 166 can be moved longitudinally forward and rearward, thereby causing the cylindrical body 160 to rotate relative to the proximal ends of the inner and outer sleeves 72 and 74. As the cylindrical body 160 rotates, the rectangular block 159 causes the intervertebral implant to change its angular orientation in the horizontal plane defined by the lateral and longitudinal directions. As illustrated, movement of the rod 166 in a forward direction causes the intervertebral implant 20 to pivot in a clockwise direction, while movement of the rod 166 in a rearward direction causes the implant to pivot in a counterclockwise direction. It should be appreciated, of course, that the rod 166 could alternatively be connected to the rectangular block 159 at a location that causes the intervertebral implant 20 to pivot in the clockwise direction when the rod is moved rearward, and counterclockwise when the rod is moved forward.

During operation, the longitudinal position of the rod 166 can be determined prior to inserting the intervertebral implant 20 into the disc space 22 so as to define an angular orientation of the implant 20 relative to the inner and outer sleeves 72 and 74. The angular orientation of the implant 20 allows the implant to be inserted into the body cavity along an anteroposterior directional approach or a posterior-anterior directional approach, while at the same time orienting the implant such that the longitudinal axis L defines a desired angle with respect to the anterior and posterior directions when the implant is inserted into the disc space 22. Once the intervertebral implant 20 has been inserted into the disc space 22, the wire 66 can be moved longitudinally forward to cause the implant 20 to expand in the transverse direction T alone, or in the transverse direction T and simultaneously the lateral direction A. Moreover, as the implant 20 expands in either the transverse direction T alone or in the transverse direction T simultaneously with the lateral direction A, the opposing transverse vertebral-engaging surfaces 32 can remain flat and parallel with each other, or can define an angular orientation configured to restore lordosis to the vertebrae 24 in the manner described above.

Figure 19A:
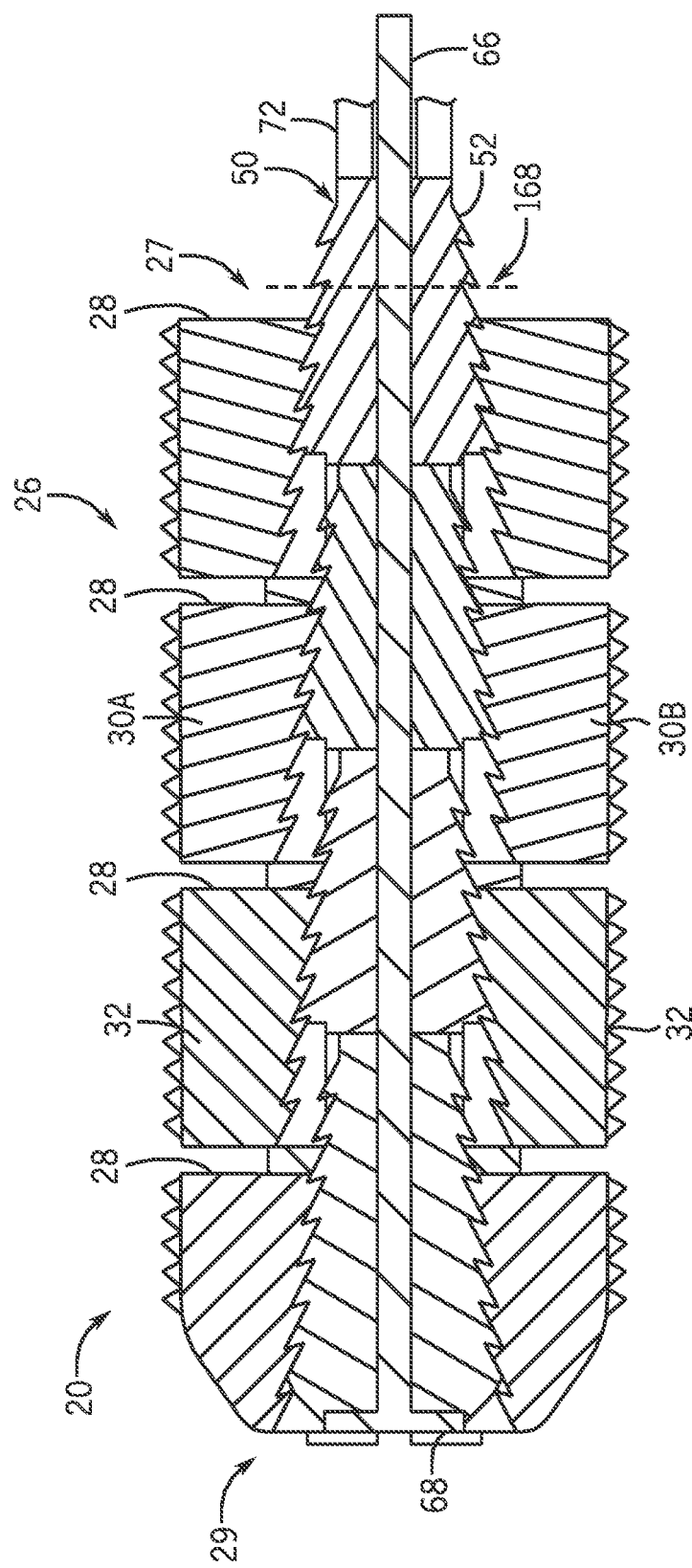
FIG. 19A is a sectional side elevation view of an expandable intervertebral implant shown in an expanded position.
Figure 19B:
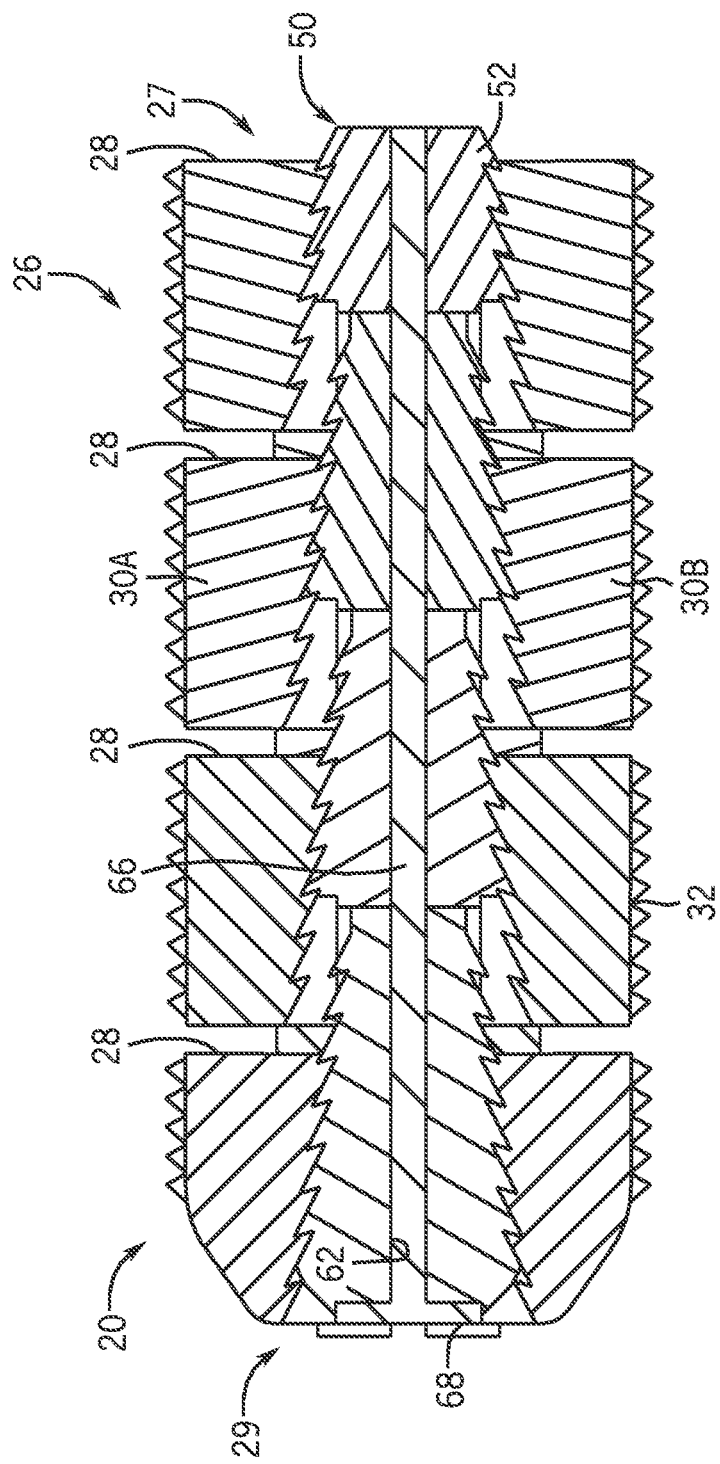
FIG. 19B is a sectional side elevation view of the expandable intervertebral implant illustrated in FIG. 19A, but showing projecting portions removed after the implant has achieved the final expanded position.

Finally, referring to FIGS. 19A and 19B, once the implant 20 has been positioned in the intervertebral space 22 and expanded to the desired expanded position, the outer sleeve 72 can be removed out of engagement with the intervertebral implant, and the remaining portions of the tool 70 can be removed by cutting the portion of the intervertebral body 50 that protrudes from the front end 127 of the linkage 26 along a cut line 168 along the lateral-transverse plane LT. The cut can be made in from opposing directions, for instance using reciprocal blades at opposing locations, such that the blades can cut through the inner core body 52 and the wire 66 and cause the body 50 to crimp around the wire 66. Alternatively, the inner core body 52 can be cut in any desired manner, and a separate crimping tool can be used to crimp the body 50 around the wire 66 after the body 50 and wire 66 have been cut, thereby securing the wire and preventing the wire 66 from being inadvertently removed after the surgical procedure has been completed.

The embodiments described in connection with the illustrated embodiments have been presented by way of illustration, and the present invention is therefore not intended to be limited to the disclosed embodiments. Furthermore, the structure and features of each the embodiments described above can be applied to the other embodiments described herein. Accordingly, those skilled in the art will realize that the invention is intended to encompass all modifications and alternative arrangements included within the spirit and scope of the invention, as set forth by the appended claims.

What is claimed:

1. An intervertebral implant comprising:
   an upper portion having an upwardly-facing vertebral engagement surface;
   a lower portion having a downwardly-facing vertebral engagement surface;
   first and second sloped engagement surfaces longitudinally offset from each other in their respective entireties, one of the first and second sloped engagement surfaces configured to engage an engagement surface of the upper portion;
   third and fourth sloped engagement surfaces longitudinally offset from each other in their respective entireties, one of the third and fourth sloped engagement surfaces configured to engage an engagement surface of the lower portion; and
   an actuation member that is configured to cause 1) the one of the first and second sloped engagement surfaces to engage the engagement surface of the upper portion so as to urge the upper portion away from the lower portion, and 2) the one of the third and fourth sloped engagement surfaces to engage the engagement surface of the lower portion so as to urge the lower portion away from the upper portion, thereby expanding the intervertebral implant from an initial position to an expanded position whereby a distance between the upwardly-facing vertebral engagement surface and the downwardly-facing vertebral engagement surfaces is increased,
   wherein the first and second sloped engagement surfaces are sloped in the same direction, and the third and fourth sloped engagement surfaces are sloped in the same direction, and
   wherein the implant is configured to remain in the expanded position under compressive forces while 1) the one of the first and second sloped engagement surfaces is engaged with the engagement surface of the upper portion, and 2) the one of the third and fourth sloped engagement surfaces is engaged with the engagement surface of the lower portion.

2. The intervertebral implant of claim 1, wherein the first and second sloped engagement surfaces are parallel to each other.

3. The intervertebral implant of claim 1, wherein the third and fourth sloped engagement surfaces are parallel to each other.

4. The intervertebral implant of claim 1, wherein a width of at least one of the upwardly-facing vertebral engagement surface and the downwardly-facing vertebral engagement surface defines a width of the intervertebral implant.

5. The intervertebral implant of claim 2, wherein the first, second, third, and fourth sloped engagement surfaces are received between the upper portion and the lower portion.

6. The intervertebral implant of claim 3, wherein the actuation member comprises a biasing member that is configured to move so as to cause translational movement of the first, second, third, and fourth sloped engagement surfaces.

7. The intervertebral implant of claim 1, wherein the first and second sloped engagement surfaces are configured to engage respective engagement surfaces of the upper portion, and the third and fourth sloped engagement surfaces are configured to engage respective engagement surfaces of the lower portion.

8. The intervertebral implant of claim 1, wherein the upper portion defines a first opening, and the lower portion defines a second opening.

9. The intervertebral implant of claim 1, wherein the one of first and second sloped engagement surfaces remains engaged with the engagement surface of the upper portion when the implant is in a fully expanded position, and the one of third and fourth sloped engagement surfaces remains engaged with the engagement surface of the upper portion when the implant is in a fully expanded position.

10. The intervertebral implant of claim 1, wherein the upper and lower portions define a relative orientation with respect to each other prior to expanding the implant, and the relative orientation remains constant before, during, and after expanding the implant.

11. The intervertebral implant of claim 1, wherein the implant defines a height from the upwardly-facing vertebral engagement surface to the downwardly-facing vertebral engagement surface, and the intervertebral implant is designed such that when the intervertebral implant is in the initial position, the height is a minimum height such that the implant is unable to achieve a height less than the minimum height via movement of the first, second, third, and fourth engagement surfaces relative to the upper and lower portions.

12. The intervertebral implant of claim 1, wherein when the expandable intervertebral implant is in the expanded position, the upper and lower portions are prevented from moving toward each other in a direction from the expanded position to the initial position while (a) the one of the first and second engagement surfaces in engagement with the engagement surface of the upper portion and (b) the one of the third and fourth engagement surfaces is in engagement with the engagement surface of the lower portion.

13. The intervertebral implant of claim 1, wherein the first and second engagement surfaces are longitudinally aligned with each other, and the third and fourth engagement surfaces are longitudinally aligned with each other.

14. The intervertebral implant of claim 1, wherein the upwardly-facing vertebral engagement surface and the downwardly-facing vertebral engagement surface define a lordotic profile when the implant is in the expanded position.

15. The intervertebral implant of claim 14, wherein a first end of the upwardly-facing vertebral engagement surface is configured to move away from the lower portion at a first rate as the implant expands from the initial position to the expanded position, and a second end of the upwardly-facing vertebral engagement surface is configured to move away from the lower portion at a second rate greater than the first rate as the implant expands from the initial position to the expanded position.

16. The intervertebral implant of claim 15, wherein a first end of the downwardly-facing vertebral engagement surface is configured to move away from the upper portion at a first rate as the implant expands from the initial position to the expanded position, and a second end of the downwardly-facing vertebral engagement surface is configured to move away from the upper portion at a second rate greater than the first rate of the first end of the downwardly-facing vertebral engagement surface as the implant expands from the initial position to the expanded position.

17. The intervertebral implant of claim 16, wherein the first ends of the upwardly-facing vertebral engagement surface and the downwardly-facing vertebral engagement surface, respectively, are aligned with each other, and the second ends of the upwardly-facing vertebral engagement surface and the downwardly-facing vertebral engagement surface, respectively, are aligned with each other.

* * * * *